(12) United States Patent
Ge

(10) Patent No.: US 9,090,594 B2
(45) Date of Patent: Jul. 28, 2015

(54) PIM KINASE INHIBITORS AND PREPARATION METHODS AND USE IN MEDICINAL MANUFACTURE THEREOF

(71) Applicant: Yu Ge, Shanghai (CN)

(72) Inventor: Yu Ge, Shanghai (CN)

(73) Assignee: JIKAI BIOSCIENCES, INC., Shanghai (CN)

(*) Notice: Subject to any disclaimer, the term of this patent is extended or adjusted under 35 U.S.C. 154(b) by 0 days.

(21) Appl. No.: 14/177,156

(22) Filed: Feb. 10, 2014

(65) Prior Publication Data
US 2014/0162999 A1    Jun. 12, 2014

Related U.S. Application Data

(63) Continuation of application No. PCT/CN2012/001060, filed on Aug. 8, 2012.

(30) Foreign Application Priority Data

Aug. 11, 2011 (CN) .......................... 2011 1 0229731
Aug. 1, 2012 (CN) .......................... 2012 1 0271738

(51) Int. Cl.
| | |
|---|---|
| C07D 403/14 | (2006.01) |
| C07D 417/12 | (2006.01) |
| C07D 417/14 | (2006.01) |
| A61K 31/4439 | (2006.01) |
| A61K 31/4545 | (2006.01) |
| C07D 471/08 | (2006.01) |
| C07D 405/14 | (2006.01) |
| C07D 451/02 | (2006.01) |
| C07D 453/02 | (2006.01) |
| C07D 401/14 | (2006.01) |
| C07D 413/14 | (2006.01) |
| C07D 451/06 | (2006.01) |
| C07D 487/08 | (2006.01) |
| A61K 31/549 | (2006.01) |
| A61K 31/5395 | (2006.01) |
| C07D 403/02 | (2006.01) |
| A61K 31/541 | (2006.01) |
| A61K 31/5355 | (2006.01) |
| C07D 413/12 | (2006.01) |

(52) U.S. Cl.
CPC .......... *C07D 403/14* (2013.01); *A61K 31/4439* (2013.01); *A61K 31/4545* (2013.01); *C07D 401/14* (2013.01); *C07D 405/14* (2013.01); *C07D 413/14* (2013.01); *C07D 417/12* (2013.01); *C07D 417/14* (2013.01); *C07D 451/02* (2013.01); *C07D 451/06* (2013.01); *C07D 453/02* (2013.01); *C07D 471/08* (2013.01); *C07D 487/08* (2013.01); *A61K 31/5355* (2013.01); *A61K 31/5395* (2013.01); *A61K 31/541* (2013.01); *A61K 31/549* (2013.01); *C07D 403/02* (2013.01); *C07D 413/12* (2013.01)

(58) Field of Classification Search
CPC . A61K 31/506; A61K 31/541; A61K 31/549; A61K 31/5355; A61K 31/5395; C07D 239/34; C07D 238/38; C07D 417/12; C07D 413/12; C07D 403/12
USPC .......................... 544/319, 295, 296; 514/269
See application file for complete search history.

(56) References Cited

U.S. PATENT DOCUMENTS

| | | |
|---|---|---|
| 4,332,809 A | 6/1982 | Honma et al. |
| 4,879,295 A | 11/1989 | Yoshinaga et al. |
| 2011/0044940 A1 | 2/2011 | Shipps, Jr. et al. |

FOREIGN PATENT DOCUMENTS

| | | |
|---|---|---|
| WO | WO 2008/106692 A1 | 9/2008 |
| WO | WO 2008141976 A1 * | 11/2008 |
| WO | WO 2010/078408 A1 | 7/2010 |

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
Marius Vantler et al., "Systematic Evaluation of Anti-Apoptotic Growth Factor Signaling in Vascular Smooth Muscle Cells," The Journal of Biological Chemistry, vol. 280, No. 14, pp. 14168-14176 (Issue of Apr. 8, 2005).
Peter S. Hammerman et al., "Pim and Akt oncogenes are independent regulators of hemotopoietic cell growth and survival," Blood, vol. 105, No. 11, pp. 4477-4483 (Jun. 1, 2005).
Casey J. Fox et al., "The Pim kinases control rapamycin-resistant T cell survival and activation," The Journal of Experimental Medicine, vol. 201, No. 2, pp. 259-266 (Jan. 17, 2005).

(Continued)

*Primary Examiner* — Alexander R Pagano
(74) *Attorney, Agent, or Firm* — Manni Li; Mei & Mark LLP

(57) ABSTRACT

PIM kinase inhibitor compound having a structure as represented by Formula I, and isomers, diastereomers, enantiomers, tautomers, and pharmaceutically acceptable salts of the compounds as represented by Formula I. The compounds significantly inhibit the Pim kinase activity and are used to prepare drugs to treat PIM kinase mediated diseases, such as cancers, autoimmune diseases, allergic reactions, or organ transplant rejection. Also provided are methods for preparing the compounds represented by Formula I.

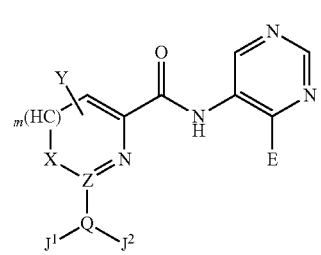

11 Claims, No Drawings

(56) References Cited

OTHER PUBLICATIONS

D.A. Fruman, "Towards an understanding of isoform specificity in phosphoinositide 3-kinase signalling in lymphocytes," Biochem. Soc. Trans. vol. 32, pp. 315-319 (2004).

Copending U.S. Appl. No. 14/177,131, Ge, Yu, filed Feb. 10, 2014.

H. Theo Cuypers et al., "Murine leukemia virus-induced T-cell lymphomagenesis: integration of proviruses in a distrinct chromosomal region," Cell, vol. 37, pp. 141-150 (May 1984).

Beth Levine et al., "Autophagy in cell death: an innocent convict?" The Journal of Clinical Investigation, vol. 115, No. 10, pp. 2679-2688 (Oct. 2005).

Nathalie M. T. Van Der Lugt et al., "Proviral tagging in Eμ-*myc* transgenic mice lacking the *Pim-1* proto-oncogene leads to compensatory activation of *Pim-2*," The EMBO Journal, vol. 14, No. 11, pp. 2536-2544 (1995).

Hans-Guido Wendel et al., "Survival signalling by Akt and eIF4E in oncogenesis and cancer therapy," Nature, 428, pp. 332-337 (Mar. 18, 2004).

Maarten Van Lohuizen et al., "Predisposition to lymphomagenesis in *pim*-1 transgenic mice: Cooperation with *c-myc* and N-*myc* in murine leukemia virus-induced tumors," Cell 56, Issue 4, pp. 673-682 (Feb. 24, 1989).

Robert Amson et al., "The human protooncogene product p33pim is expressed during fetal hematopoiesis and in diverse leukemias," Proc. Natl. Acad. Sci. USA, vol. 86, pp. 8857-8861 (Nov. 1989).

T.L. Cibull et al., "Overexpression of Pim-1 during progression of prostatic adenocarcinoma," J. Clin. Pathol., vol. 59, pp. 285-288 (2006).

Amos M. Cohen et al., "Increased Expression of the hPim-2 gene in human chronic lymphocytic leukemia and non-Hodgkin lymphoma," Leuk. Lymph., 45, pp. 951-955 (2004).

Chifumi Fuji! Etal., "Aberrant expression of serine/threonine kinase Pim-3 in hepatocellular carcinoma development and its role in the proliferation of human hepatoma cell lines," Int. J. Cancer, vol. 114, pp. 209-218 (2005).

Ying-Yi Li et al., "Pim-3, a proto-oncogene with serine/threonine kinase activity, is aberrantly expressed in human pancreatic cancer and phosphorylates bad to block bad-mediated apoptosis in human pancreatic cancer cell lines," Cancer Res., vol. 66, pp. 6741-6747 (Jul. 1, 2006).

Teija L.T. Aho et al., "Pim-1 kinase promotes inactivation of the pro-apoptotic bad protein by phosphorylating it on the $Ser^{112}$ gatekeeper site," FEBS Letters, vol. 571, pp. 43-49 (2004).

Zeping Wang et al., "Phosphorylation of the cell cycle inhibitor $p21^{Cip1/WAF1}$ by Pim-1 kinase," Biochem. Biophys. Acta, vol. 1593, pp. 45-55 (2002).

Malte Bachmann et al., "The oncogenic serine/threonine kinase Pim-1 phosphorylates and inhibits the activity of Cdc25C-associated kinase 1 (C-TAK1)," The Journal of Biological Chemistry, vol. 279, No. 46, pp. 48319-48328 (Issue of Nov. 12, 2004).

Teija L. T. Aho et al., "Expression of human *pim* family genes is selectively up-regulated by cytokines promoting T helper type 1, but not T helper type 2, cell differentiation," Immunology, vol. 116, pp. 82-88 (2005).

* cited by examiner

PIM KINASE INHIBITORS AND PREPARATION METHODS AND USE IN MEDICINAL MANUFACTURE THEREOF

CROSS-REFERENCE AND RELATED APPLICATIONS

The subject application is a continuation of PCT international application PCT/CN2012/001060 filed on Aug. 8, 2012, which in turn claims priority on Chinese patent applications CN 201110229731.X filed on Aug. 11, 2011 and CN 201210271738.2 filed on Aug. 1, 2012. The contents and subject matter of the PCT and Chinese priority applications are incorporated herein by reference.

TECHNICAL FIELD

The present invention relates to medicinal chemistry, particularly PIM kinase inhibitors, methods of preparation, and their pharmaceutical application in treating diseases.

BACKGROUND

PIM kinase family consists of three homologous serine/threonine kinases, Pim-1, Pim-2, and Pim-3, which belong to calmodulin-dependent protein kinase-related family (CAMK). Researches have shown that PIM kinases are widely expressed in hematopoietic tissues (J. Biol. Chem., 280, 14168-14176, 2005; Blood, 105, 4477-4483, 2005) and play important roles in cell survival and proliferation. Since PIM kinases are overexpressed in a variety of malignancies and inflammations (J. Exp. Med., 201, 259-266, 2005; Biochem. Soc. Trans., 32, 315-319, 2004), they are more and more being targeted for treating cancers and immune dysfunctions. PIM-1 (Provirus Integration of Maloney 1) was originally identified in a series of insertional mutagenesis studies of retroviruses, as a frequent proviral integration site in Moloney murine leukemia virus-induced T-cell lymphomas, and PIM-1 was named based on that finding (Cell, 37, 141-150, 1984). It was found later that the genes encoding PIM-2 (Provirus Integration of Maloney 2) have the same defect (J. Clin. Invest., 115, 2679-2688, 2005). Pim-2 has similar effects as and compensatory to Pim-1 (J EMBO, 14, 2536, 1995). PIM-3 was initially named as KID-1 (Kinase Induced by Depolarization 1), but renamed to Pim-3 because of its high sequence similarity to Pim-1 (Nature, 428, 332-337, 2005; Cell, 56, 673-682, 1989). PIM-1, 2, 3 are overly expressed in many hematopoietic malignancies (PNAS USA, 86, 8857-8861, 1989). PIM-1 was found to be overexpressed in the development of prostate cancer (J. Clin. Pathol., 59, 285-288, 2006). PIM-2 expression is elevated in human chronic lymphocytic leukemia and non-Hodgkin's lymphoma leukemia (Leuk. Lymph., 45, 951-955, 2004), the aberrant expression of PIM-3 is believed to have played an important role in the development and proliferation of live fibroma (Int. J. Cancer, 114, 209-218, 2005) and pancreatic cancer (Cancer Res., 66, 6741-6747, 2006).

PIM-1, 2, 3 have effects on the survival and proliferation of hematopoietic cells in response to growth factors stimulation. PIM-1, 2, 3 triple knockout mice are viable and fertile while displaying reduced body size and impairment of proliferation of hematopoietic cells in response to growth factors. Knocking out one of 3 kinases does not have obvious effect on mice, indicating some overlapping functions among PIM kinases (Cell, 56, 673-682, 1989). The substrates of PIM kinases include Bcl-2 family members such as pro-apoptotic BAD protein (FEBS Letters, 571, 43-49, 2004), cell cycle regulating p21 (Biochem. Biophys. Acta, 1593, 45-55, 2002), CDC25A, C-TA (J. Biol. Chem., 279, 48319-48328, 2004), protein synthesis related 4EBP1 (Blood, 105, 4477-4483, 2005). These functions of PIM kinases indicate that PIM kinases can prevent apoptosis and promote cell growth and proliferation. Their overexpression in cancer cells promotes the survival and proliferation of the cancer cells. Therefore, inhibiting the PIM kinase activities in cancer cell is a new effective way of treating cancers. Besides cancer, PIM inhibitors can also be used to treat autoimmune diseases, allergic reactions, and organ transplant rejection (Immunology, 116, 82-88, 2005).

SUMMARY OF THE INVENTION

The present invention provides chemical compounds having certain biological activities that include, but not limited to, inhibiting cell proliferation, promoting apoptosis, and modulating protein kinase activities. The present invention provides compounds that inhibit the activities of PIM-1, PIM-2 and PIM-3 kinases. The present invention also provides methods for preparing novel chemical compounds, and analogs thereof, and methods of using these compounds to treat cancers, autoimmune diseases, allergic reactions, and organ transplant rejection.

The PIM kinase inhibitors of the present invention have the following general structural Formula I, and their isomers, diastereomers, enantiomers, tautomers, and pharmaceutically acceptable salts,

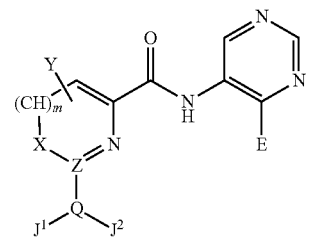

I

Wherein,
E, $J^1$, $J^2$, Q, X, Y, Z, m of Formula I are:
When m is 0, X is S, O, N or CH;
When m is 1, X is CH or N;
Z is CH or N;
Y is H or $N(R^1R^2)$, each of $R^1$, $R^2$ is independently selected from H or optionally substituted $C_1$-$C_8$ hydrocarbon group; or Y is H or $N(R^1C(=O)R^2)$, each of $R^1$, $R^2$ is independently selected from H or optionally substituted $C_1$-$C_8$ hydrocarbon group;
E is $OR^{22}$, $SR^{22}$, $SO_2R^{22}$; $R^{22}$ is optionally substituted $C_1$-$C_8$ hydrocarbon group or the group described in the following formula:

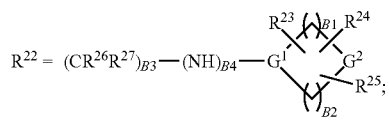

Wherein,
Each of $R^{23}$, $R^{24}$, $R^{25}$ is independently selected from H, halo, $OR^{15}$, $NR^{16}R^{17}$, $C(=O)NR^{18}R^{19}$ or optionally substituted $C_1$-$C_8$ hydrocarbon group; or $R^{23}$, $R^{24}$ and $R^{25}$, together with the atoms to which they are attached, may be joined together to form a chain so that the ring to which they are attached is a substituted $C_6$-$C_{14}$ membered spiral ring, bicyclic ring or fused ring group;

$G^1$ is CH or N;

$G^2$ is $NR^{28}$, $CHR^{29}$ or O;

B1 and B2 each independently represents 0, 1, 2 or 3;

B3 is 0, 1 or 2;

B4 is 0, 1;

Each of $R^{26}$ and $R^{27}$ is independently selected from H or optionally substituted $C_1$-$C_8$ hydrocarbon group;

$R^{28}$ is H, optionally substituted hydrocarbon group, optionally substituted cyclic hydrocarbon group, optionally substituted heterocyclic hydrocarbon group, $C(=O)R^{30}$, $C(=O)OR^{30}$ or $C(=O)NHR^{30}$;

$R^{29}$ is OH, $NHR^{30}$, $C(=O)OR^{30}$ or $C(=O)NHR^{30}$;

$R^{30}$ is H or optionally substituted $C_1$-$C_8$ hydrocarbon group;

Q is C, CH or N;

$J^1$, $J^2$ is independently selected from H or optionally substituted $C_1$-$C_8$ hydrocarbon group, $OR^{31}$, $NHR^{31}$ or $C(=O)R^{31}$; or $J^1$, $J^2$ together with CH they are attached, are joined together to form a $C_3$-$C_8$ membered cycloalkyl; or $J^1$, $J^2$ together with the atoms to which they are attached and at least one hetero atom to form $C_4$-$C_7$ membered heterocycloalkyl; on such $C_3$-$C_8$ membered cycloalkyl and $C_4$-$C_7$ membered heterocycloalkyl, one or more position can be optionally substituted with halo, $OR^{32}$, $NHR^{33}$ or optionally substituted $C_1$-$C_8$ hydrocarbon group, or such substituents are joined together to form a chain so that the ring to which they are attached is a substituted $C_6$-$C_{14}$ membered spiral ring, bicyclic ring or fused ring group; or $J^1$, $J^2$ together with C atom they are attached, are joined together to form aromatic rings, such as benzene ring and naphthlene, or $J^1$, $J^2$ together with C they are attached and at least one heteroatom, are joined together to form $C_5$-$C_6$ membered aromatic heterocycles, such as pyridine, pyrimidine, pyrazine, imidazole, thiazole, isoxazole, oxazole or pyrrole, on the aromatic rings and hetero aromatic rings, one or more position can be optionally substituted with halo, CN, $OR^{32}$, $NHR^{33}$ or optionally substituted $C_1$-$C_8$ hydrocarbon group, or such substituents are joined together to form a chain so that the ring to which they are attached is an optionally substituted $C_6$-$C_{14}$ membered aromatic spiral ring, bicyclic ring or fused ring group; or $J^1$, $J^2$ together with N atom they are attached, are joined together to form $C_4$-$C_7$ membered heterocycloalkyl group, or $J^1$, $J^2$ together with N atom they are attached, and at least one hetero atom, are joined together to form $C_4$-$C_7$ membered heterocycloalkyl group; on these $C_4$-$C_7$ membered heterocycloalkyl group, one or more position can be optionally substituted with halo, CN, $OR^{32}$, $NHR^{33}$ or optionally substituted $C_1$-$C_8$ hydrocarbon group, or such substituents are joined together to form a chain so that the ring to which they are attached is an optionally substituted $C_6$-$C_{14}$ membered aromatic spiral ring, bicyclic ring or fused ring group;

$R^{31}$ is H or optionally substituted $C_1$-$C_8$ hydrocarbon group;

Each of $R^{32}$, $R^{33}$ is independently selected from H or optionally substituted $C_1$-$C_8$ hydrocarbon group, optionally substituted $C_3$-$C_8$ cyclic hydrocarbon group, optionally substituted $C_4$-$C_7$ membered heterocyclic hydrocarbon group, $C(=O)R^{34}$, $C(=O)OR^{34}$ or $C(=O)NHR^{34}$;

$R^{34}$ is H or optionally substituted $C_1$-$C_8$ hydrocarbon group.

DETAILED DESCRIPTION OF THE INVENTION

As used herein, the term 'substituent' refers to atom or atomic group that replaces the hydrogen atoms of the molecule. As used herein, 'optionally substituted' substituent refers to substituents that each of the replaceable hydrogen atoms on the substituents may be substituted by other atom or atomic group.

As used herein, the term 'hydrocarbon group' refers to alkyl group (saturated aliphatic group), alkenyl group (having at least one carbon-carbon double bond), alkynyl group (having at least one carbon-carbon triple bond); The 'hydrocarbon group' may be linear, branced or cyclic; the 'hydrocarbon group' may be aliphatic or aromatic.

As used herein, the term 'cyclic hydrocarbon group' refers to cycloalkyl group or cycloalkenyl group (having at least one carbon-carbon double bond), aromatic group; 'cyclic hydrocarbon group' may be monocyclic, bicyclic or multi-cyclic group; 'cyclic hydrocarbon group' may be spiral or fused ring.

As used herein, the term 'hetero cyclic hydrocarbon group' refers to cycloalkyl group or cycloalkenyl group (having at least one carbon-carbon double bond), aromatic group with one or more ring atoms are hetero atoms such as N, O, S, or combination thereof; 'hetero cyclic hydrocarbon group' may be monocyclic, bicyclic or multi-cyclic group; 'hetero cyclic hydrocarbon group' may be spiral or fused ring.

As used herein, the term 'substituent' include but not limited to: halo (F, Cl, Br, I), $-OR^{26}$, $-OC(=O)R^{26}$, $-OC(=O)NR^{26}R^{27}$, $=O$, $-SR^{26}$, $-SOR^{26}$, $-SO_2R^{26}$, $-SO_2NR^{26}R^{27}$, $-C(=O)R^{26}$, $-C(=O)OR^{26}$, $-C(=O)NR^{26}R^{27}$, $-R^{26}CN$, $-NR^{26}R^{27}$, $-NHC(=O)R^{26}$, $-NHC(=O)NR^{26}R^{27}$, $-NHC(=S)NR^{26}R^{27}$, halogenated (F, Cl, Br, I) hydrocarbon;

Wherein;

Each of $R^{26}$ and $R^{27}$ is independently selected from H or optionally substituted $C_1$-$C_8$ hydrocarbon group.

The compounds described in the present invention that are acidic in nature can form pharmaceutically acceptable salts by reacting with physiologically compatible organic or inorganic bases, such as readily soluble alkali and alkaline earth salts, and salts formed from reacting with ammonia, N-methyl-glucamine, dimethyl-glucamine, ethyl-glucamine, lysine, ethanolamine, glucosamine, sarcosine, serine, tris(hydroxymethyl)aminomethane, 1-amino-2,3,4-butanetriol.

The compounds described in the present invention that are basic in nature can form pharmaceutically acceptable salts by reacting with physiologically compatible organic or inorganic acids, such as the salts formed by reacting with hydrochloric acid, hydrobromic acid, sulfuric acid, phosphoric acid, methanesulfonic acid, toluene-sulfonic acid, carbonic acid, succinic acid, citric acid, benzoic acid, oxalic acid, malonic acid, salicylic acid, malic acid, fumaric acid, maleic acid, acetic acid, ascorbic acid.

The compounds in the present invention may be pure chiral compounds, racemic mixtures, optically active compounds, pure diastereomers, or mixed diastereomers.

The present invention provides PIM kinase inhibitors which include the following compounds:

2-(2,6-difluorophenyl)-N-(4-(pyrrolidin-3-yloxy)pyrimidin-5-yl)thiazole-4-carboxamide (1)

N-(4-(azepan-4-yloxy)pyrimidin-5-yl)-2-(2,6-difluorophenyl)thiazole-4-carboxamide (2)

2-(2,6-difluorophenyl)-N-(4-(piperidin-4-yloxy)pyrimidin-5-yl)thiazole-4-carboxamide (3)

5-amino-2-(2,6-difluorophenyl)-N-(4-(piperidin-4-yloxy)pyrimidin-5-yl)thiazole-4-carboxamide (4)

2-(2,6-difluorophenyl)-N-(4-((4-hydroxycyclohexyl)oxy)pyrimidin-5-yl)thiazole-4-carboxamide (5)

2-(2,6-difluorophenyl)-N-(4-(oxetan-3-yloxy)pyrimidin-5-yl)thiazole-4-carboxamide (6)

2-(2,6-difluorophenyl)-N-(4-((3-hydroxycyclopentyl)oxy) pyrimidin-5-yl)thiazole-4-carboxamide (7)
2-(2,6-difluorophenyl)-N-(4-((2,2,6,6-tetramethylpiperidin-4-yl)oxy)pyrimidin-5-yl)thiazole-4-carboxamide (8)
2-(2,6-difluorophenyl)-N-(4-((3-methyloxetan-3-yl)methoxy)pyrimidin-5-yl)thiazole-4-carboxamide (9)
N-(4-(azetidin-3-ylmethoxy)pyrimidin-5-yl)-2-(2,6-difluorophenyl)thiazole-4-carboxamide (10)
6-(2,6-difluorophenyl)-N-(4-(piperidin-4-yloxy)pyrimidin-5-yl)picolinamide (11)
2-(2,6-difluorophenyl)-N-(4-((tetrahydrofuran-3-yl)methoxy)pyrimidin-5-yl)thiazole-4-carboxamide (12)
2-(2,6-difluorophenyl)-N-(4-((tetrahydro-2H-pyran-4-yl)methoxy)pyrimidin-5-yl)thiazole-4-carboxamide (13)
N-(4-(8-azabicyclo[3.2.1]octan-3-yloxy)pyrimidin-5-yl)-2-(2,6-difluorophenyl)thiazole-4-carboxamide (14)
2-(2,6-difluorophenyl)-N-(4-(piperidin-4-ylmethoxy)pyrimidin-5-yl)thiazole-4-carboxamide (15)
2-(2,6-difluorophenyl)-N-(4-((tetrahydro-2H-pyran-4-yl)oxy)pyrimidin-5-yl)thiazole-4-carboxamide (16)
N-(4-(3-azabicyclo[3.2.0]heptan-6-yloxy)pyrimidin-5-yl)-2-(2,6-difluorophenyl)thiazole-4-carboxamide (17)
2-(2,6-difluorophenyl)-N-(4-(pyrrolidin-3-ylmethoxy)pyrimidin-5-yl)thiazole-4-carboxamide (18)
2-(2,6-difluorophenyl)-N-(4-(quinuclidin-3-ylmethoxy)pyrimidin-5-yl)thiazole-4-carboxamide (19)
3-amino-6-(2,6-difluorophenyl)-N-(4-((3-methyloxetan-3-yl)methoxy)pyrimidin-5-yl)picolinamide (20)
N-(4-(azetidin-3-yloxy)pyrimidin-5-yl)-2-(2,6-difluorophenyl)thiazole-4-carboxamide (21)
2-(2,6-difluorophenyl)-N-(4-(piperidin-3-yloxy)pyrimidin-5-yl)thiazole-4-carboxamide (22)
5-(2,6-difluorophenyl)-N-(4-(piperidin-4-ylmethoxy)pyrimidin-5-yl)thiophene-2-carboxamide (23)
N-(4-((cis-4-aminocyclohexyl)oxy)pyrimidin-5-yl)-2-(2,6-difluorophenyl)thiazole-4-carboxamide (24)
5-amino-2-(2,6-difluorophenyl)-N-(4-((3-methyloxetan-3-yl)methoxy)pyrimidin-5-yl)thiazole-4-carboxamide (25)
5-amino-N-(4-(azepan-4-yloxy)pyrimidin-5-yl)-2-(2,6-difluorophenyl)thiazole-4-carboxamide (26)
5-amino-N-(4-((trans-4-aminocyclohexyl)oxy)pyrimidin-5-yl)-2-(2,6-difluorophenyl)thiazole-4-carboxamide (27)
5-amino-2-(2,6-difluorophenyl)-N-(4-(piperidin-4-ylmethoxy)pyrimidin-5-yl)thiazole-4-carboxamide (28)
5-amino-N-(4-(4-aminobutoxy)pyrimidin-5-yl)-2-(2,6-difluorophenyl)thiazole-4-carboxamide (29)
5-amino-2-(2,6-difluorophenyl)-N-(4-(4-hydroxybutoxy)pyrimidin-5-yl)thiazole-4-carboxamide (30)
2-(2,6-difluorophenyl)-N-(4-(((3S,4R)-3-fluoropiperidin-4-yl)oxy)pyrimidin-5-yl)thiazole-4-carboxamide (31)
3-amino-6-(2,6-difluorophenyl)-N-(4-(piperidin-4-yloxy)pyrimidin-5-yl)picolinamide (32)
2-isopropyl-N-(4-(piperidin-4-yloxy)pyrimidin-5-yl)thiazole-4-carboxamide (33)
5-amino-2-(2,6-difluorophenyl)-N-(4-(pyrrolidin-3-yloxy)pyrimidin-5-yl)thiazole-4-carboxamide (34)
5-amino-2-(2,6-difluorophenyl)-N-(4-((3-hydroxypropyl)thio)pyrimidin-5-yl)thiazole-4-carboxamide (35)
5-amino-2-(2,6-difluorophenyl)-N-(4-((2,2-dimethyl-1,3-dioxolan-4-yl)methoxy)pyrimidin-5-yl)thiazole-4-carboxamide (36)
2-(2,6-difluorophenyl)-N-(4-(((1S,3R)-3-hydroxycyclopentyl)oxy)pyrimidin-5-yl)thiazole-4-carboxamide (37)
5-amino-2-(2,6-difluorophenyl)-N-(4-(2-(2,2-dimethyl-1,3-dioxolan-4-yl)ethoxy)pyrimidin-5-yl)thiazole-4-carboxamide (38)
5-amino-2-(2,6-difluorophenyl)-N-(4-(3-hydroxy-3-methylbutoxy)pyrimidin-5-yl)thiazole-4-carboxamide (39)
2-(2,6-difluorophenyl)-N-(4-(3-hydroxy-3-methylbutoxy)pyrimidin-5-yl)thiazole-4-carboxamide (40)
5-amino-2-(2,6-difluorophenyl)-N-(4-(3-hydroxybutoxy)pyrimidin-5-yl)thiazole-4-carboxamide (41)
2-(2,6-difluorophenyl)-N-(4-(3-hydroxybutoxy)pyrimidin-5-yl)thiazole-4-carboxamide (42)
5-amino-N-(4-((4-carbamoylcyclohexyl)oxy)pyrimidin-5-yl)-2-(2,6-difluorophenyl)thiazole-4-carboxamide (43)
5-amino-2-(2,6-difluorophenyl)-N-(4-(2-hydroxyethoxy)pyrimidin-5-yl)thiazole-4-carboxamide (44)
5-amino-2-(2,6-difluorophenyl)-N-(4-((4-hydroxypentyl)oxy)pyrimidin-5-yl)thiazole-4-carboxamide (45)
2-(2,6-difluorophenyl)-N-(4-((4-hydroxypentyl)oxy)pyrimidin-5-yl)thiazole-4-carboxamide (46)
5-amino-2-(2,6-difluorophenyl)-N-(4-((4-hydroxy-4-methylpentyl)oxy)pyrimidin-5-yl)thiazole-4-carboxamide (47)
2-(2,6-difluorophenyl)-N-(4-((4-hydroxy-4-methylpentyl)oxy)pyrimidin-5-yl)thiazole-4-carboxamide (48)
5-amino-2-(2,6-difluorophenyl)-N-(4-(3,4-dihydroxybutoxy)pyrimidin-5-yl)thiazole-4-carboxamide (49)
2-(2,6-difluorophenyl)-N-(4-(3,4-dihydroxybutoxy)pyrimidin-5-yl)thiazole-4-carboxamide (50)
5-amino-2-(2,6-difluorophenyl)-N-(4-(2,3-dihydroxypropoxy)pyrimidin-5-yl)thiazole-4-carboxamide (51)
5-amino-2-(2,6-difluorophenyl)-N-(4-(4-(methylamino)butoxy)pyrimidin-5-yl)thiazole-4-carboxamide (52)
5-amino-2-(2,6-difluorophenyl)-N-(4-(piperidin-4-ylthio)pyrimidin-5-yl)thiazole-4-carboxamide (53)
2-(2,6-difluorophenyl)-N-(4-((4-hydroxy-4-methylpentyl)oxy)pyrimidin-5-yl)-5-(methylamino)thiazole-4-carboxamide (54)
2-(2,6-difluorophenyl)-5-formamido-N-(4-((4-hydroxy-4-methylpentyl)oxy)pyrimidin-5-yl)thiazole-4-carboxamide (55)
2-(2,6-difluorophenyl)-5-(methylamino)-N-(4-(piperidin-4-yloxy)pyrimidin-5-yl)thiazole-4-carboxamide (56)
2-(2,6-difluorophenyl)-N-(4-(piperidin-4-yloxy)pyrimidin-5-yl)oxazole-4-carboxamide (57)
N-(4-(piperidin-4-yloxy)pyrimidin-5-yl)-2-(pyridin-2-yl)thiazole-4-carboxamide (58)
2-(piperidin-4-yl)-N-(4-(piperidin-4-yloxy)pyrimidin-5-yl)thiazole-4-carboxamide (59)
2-morpholino-N-(4-(piperidin-4-yloxy)pyrimidin-5-yl)thiazole-4-carboxamide (60)
2-(piperidin-1-yl)-N-(4-(piperidin-4-yloxy)pyrimidin-5-yl)thiazole-4-carboxamide (61)
2-acetamido-N-(4-(piperidin-4-yloxy)pyrimidin-5-yl)thiazole-4-carboxamide (62)
5-amino-2-(2,6-difluorophenyl)-N-(4-((3-hydroxypropyl)sulfonyl)pyrimidin-5-yl)thiazole-4-carboxamide (63)

Preferred compounds:
2-(2,6-difluorophenyl)-N-(4-(pyrrolidin-3-yloxy)pyrimidin-5-yl)thiazole-4-carboxamide (1)
N-(4-(azepan-4-yloxy)pyrimidin-5-yl)-2-(2,6-difluorophenyl)thiazole-4-carboxamide (2)
2-(2,6-difluorophenyl)-N-(4-(piperidin-4-yloxy)pyrimidin-5-yl)thiazole-4-carboxamide (3)
5-amino-2-(2,6-difluorophenyl)-N-(4-(piperidin-4-yloxy)pyrimidin-5-yl)thiazole-4-carboxamide (4)
2-(2,6-difluorophenyl)-N-(4-((4-hydroxycyclohexyl)oxy)pyrimidin-5-yl)thiazole-4-carboxamide (5)
2-(2,6-difluorophenyl)-N-(4-(oxetan-3-yloxy)pyrimidin-5-yl)thiazole-4-carboxamide (6)
2-(2,6-difluorophenyl)-N-(4-((3-hydroxycyclopentyl)oxy)pyrimidin-5-yl)thiazole-4-carboxamide (7)

2-(2,6-difluorophenyl)-N-(4-((2,2,6,6-tetramethylpiperidin-4-yl)oxy)pyrimidin-5-yl)thiazole-4-carboxamide (8)
2-(2,6-difluorophenyl)-N-(4-((3-methyloxetan-3-yl)methoxy)pyrimidin-5-yl)thiazole-4-carboxamide (9)
N-(4-(azetidin-3-ylmethoxy)pyrimidin-5-yl)-2-(2,6-difluorophenyl)thiazole-4-carboxamide (10)
6-(2,6-difluorophenyl)-N-(4-(piperidin-4-yloxy)pyrimidin-5-yl)picolinamide (11)
2-(2,6-difluorophenyl)-N-(4-((tetrahydrofuran-3-yl)methoxy)pyrimidin-5-yl)thiazole-4-carboxamide (12)
2-(2,6-difluorophenyl)-N-(4-((tetrahydro-2H-pyran-4-yl)methoxy)pyrimidin-5-yl)thiazole-4-carboxamide (13)
N-(4-(8-azabicyclo[3.2.1]octan-3-yloxy)pyrimidin-5-yl)-2-(2,6-difluorophenyl)thiazole-4-carboxamide (14)
2-(2,6-difluorophenyl)-N-(4-(piperidin-4-ylmethoxy)pyrimidin-5-yl)thiazole-4-carboxamide (15)
2-(2,6-difluorophenyl)-N-(4-((tetrahydro-2H-pyran-4-yl)oxy)pyrimidin-5-yl)thiazole-4-carboxamide (16)
N-(4-(3-azabicyclo[3.2.0]heptan-6-yloxy)pyrimidin-5-yl)-2-(2,6-difluorophenyl)thiazole-4-carboxamide (17)
2-(2,6-difluorophenyl)-N-(4-(pyrrolidin-3-ylmethoxy)pyrimidin-5-yl)thiazole-4-carboxamide (18)
2-(2,6-difluorophenyl)-N-(4-(quinuclidin-3-ylmethoxy)pyrimidin-5-yl)thiazole-4-carboxamide (19)
3-amino-6-(2,6-difluorophenyl)-N-(4-((3-methyloxetan-3-yl)methoxy)pyrimidin-5-yl)picolinamide (20)
N-(4-(azetidin-3-yloxy)pyrimidin-5-yl)-2-(2,6-difluorophenyl)thiazole-4-carboxamide (21)
2-(2,6-difluorophenyl)-N-(4-(piperidin-3-yloxy)pyrimidin-5-yl)thiazole-4-carboxamide (22)
N-(4-((cis-4-aminocyclohexyl)oxy)pyrimidin-5-yl)-2-(2,6-difluorophenyl)thiazole-4-carboxamide (24)
5-amino-2-(2,6-difluorophenyl)-N-(4-((3-methyloxetan-3-yl)methoxy)pyrimidin-5-yl)thiazole-4-carboxamide (25)
5-amino-N-(4-(azepan-4-yloxy)pyrimidin-5-yl)-2-(2,6-difluorophenyl)thiazole-4-carboxamide (26)
5-amino-N-(4-((trans-4-aminocyclohexyl)oxy)pyrimidin-5-yl)-2-(2,6-difluorophenyl)thiazole-4-carboxamide (27)
5-amino-2-(2,6-difluorophenyl)-N-(4-(piperidin-4-ylmethoxy)pyrimidin-5-yl)thiazole-4-carboxamide (28)
5-amino-N-(4-(4-aminobutoxy)pyrimidin-5-yl)-2-(2,6-difluorophenyl)thiazole-4-carboxamide (29)
5-amino-2-(2,6-difluorophenyl)-N-(4-(4-hydroxybutoxy)pyrimidin-5-yl)thiazole-4-carboxamide (30)
2-(2,6-difluorophenyl)-N-(4-(((3S,4R)-3-fluoropiperidin-4-yl)oxy)pyrimidin-5-yl)thiazole-4-carboxamide (31)
3-amino-6-(2,6-difluorophenyl)-N-(4-(piperidin-4-yloxy)pyrimidin-5-yl)picolinamide (32)
5-amino-2-(2,6-difluorophenyl)-N-(4-(pyrrolidin-3-yloxy)pyrimidin-5-yl)thiazole-4-carboxamide (34)
2-(2,6-difluorophenyl)-N-(4-(((1S,3R)-3-hydroxycyclopentyl)oxy)pyrimidin-5-yl)thiazole-4-carboxamide (37)
5-amino-2-(2,6-difluorophenyl)-N-(4-(3-hydroxy-3-methylbutoxy)pyrimidin-5-yl)thiazole-4-carboxamide (39)
2-(2,6-difluorophenyl)-N-(4-(3-hydroxy-3-methylbutoxy)pyrimidin-5-yl)thiazole-4-carboxamide (40)
5-amino-2-(2,6-difluorophenyl)-N-(4-(3-hydroxybutoxy)pyrimidin-5-yl)thiazole-4-carboxamide (41)
2-(2,6-difluorophenyl)-N-(4-(3-hydroxybutoxy)pyrimidin-5-yl)thiazole-4-carboxamide (42)
5-amino-N-(4-((4-carbamoylcyclohexyl)oxy)pyrimidin-5-yl)-2-(2,6-difluorophenyl)thiazole-4-carboxamide (43)
5-amino-2-(2,6-difluorophenyl)-N-(4-((4-hydroxypentyl)oxy)pyrimidin-5-yl)thiazole-4-carboxamide (45)
2-(2,6-difluorophenyl)-N-(4-((4-hydroxypentyl)oxy)pyrimidin-5-yl)thiazole-4-carboxamide (46)
5-amino-2-(2,6-difluorophenyl)-N-(4-((4-hydroxy-4-methylpentyl)oxy)pyrimidin-5-yl)thiazole-4-carboxamide (47)
2-(2,6-difluorophenyl)-N-(4-((4-hydroxy-4-methylpentyl)oxy)pyrimidin-5-yl)thiazole-4-carboxamide (48)
5-amino-2-(2,6-difluorophenyl)-N-(4-(3,4-dihydroxybutoxy)pyrimidin-5-yl)thiazole-4-carboxamide (49)
2-(2,6-difluorophenyl)-N-(4-(3,4-dihydroxybutoxy)pyrimidin-5-yl)thiazole-4-carboxamide (50)
5-amino-2-(2,6-difluorophenyl)-N-(4-(2,3-dihydroxypropoxy)pyrimidin-5-yl)thiazole-4-carboxamide (51)
5-amino-2-(2,6-difluorophenyl)-N-(4-(4-(methylamino)butoxy)pyrimidin-5-yl)thiazole-4-carboxamide (52)
5-amino-2-(2,6-difluorophenyl)-N-(4-(piperidin-4-ylthio)pyrimidin-5-yl)thiazole-4-carboxamide (53)
N-(4-(piperidin-4-yloxy)pyrimidin-5-yl)-2-(pyridin-2-yl)thiazole-4-carboxamide (58)

More preferred compounds:
2-(2,6-difluorophenyl)-N-(4-(pyrrolidin-3-yloxy)pyrimidin-5-yl)thiazole-4-carboxamide (1)
N-(4-(azepan-4-yloxy)pyrimidin-5-yl)-2-(2,6-difluorophenyl)thiazole-4-carboxamide (2)
2-(2,6-difluorophenyl)-N-(4-(piperidin-4-yloxy)pyrimidin-5-yl)thiazole-4-carboxamide (3)
5-amino-2-(2,6-difluorophenyl)-N-(4-(piperidin-4-yloxy)pyrimidin-5-yl)thiazole-4-carboxamide (4)
2-(2,6-difluorophenyl)-N-(4-((4-hydroxycyclohexyl)oxy)pyrimidin-5-yl)thiazole-4-carboxamide (5)
2-(2,6-difluorophenyl)-N-(4-((3-methyloxetan-3-yl)methoxy)pyrimidin-5-yl)thiazole-4-carboxamide (9)
N-(4-(azetidin-3-ylmethoxy)pyrimidin-5-yl)-2-(2,6-difluorophenyl)thiazole-4-carboxamide (10)
2-(2,6-difluorophenyl)-N-(4-((tetrahydrofuran-3-yl)methoxy)pyrimidin-5-yl)thiazole-4-carboxamide (12)
2-(2,6-difluorophenyl)-N-(4-((tetrahydro-2H-pyran-4-yl)methoxy)pyrimidin-5-yl)thiazole-4-carboxamide (13)
2-(2,6-difluorophenyl)-N-(4-(piperidin-4-ylmethoxy)pyrimidin-5-yl)thiazole-4-carboxamide (15)
2-(2,6-difluorophenyl)-N-(4-((tetrahydro-2H-pyran-4-yl)oxy)pyrimidin-5-yl)thiazole-4-carboxamide (16)
2-(2,6-difluorophenyl)-N-(4-(pyrrolidin-3-ylmethoxy)pyrimidin-5-yl)thiazole-4-carboxamide (18)
N-(4-(azetidin-3-yloxy)pyrimidin-5-yl)-2-(2,6-difluorophenyl)thiazole-4-carboxamide (21)
2-(2,6-difluorophenyl)-N-(4-(piperidin-3-yloxy)pyrimidin-5-yl)thiazole-4-carboxamide (22)
N-(4-((cis-4-aminocyclohexyl)oxy)pyrimidin-5-yl)-2-(2,6-difluorophenyl)thiazole-4-carboxamide (24)
5-amino-2-(2,6-difluorophenyl)-N-(4-((3-methyloxetan-3-yl)methoxy)pyrimidin-5-yl)thiazole-4-carboxamide (25)
5-amino-N-(4-(azepan-4-yloxy)pyrimidin-5-yl)-2-(2,6-difluorophenyl)thiazole-4-carboxamide (26)
5-amino-N-(4-((trans-4-aminocyclohexyl)oxy)pyrimidin-5-yl)-2-(2,6-difluorophenyl)thiazole-4-carboxamide (27)
5-amino-2-(2,6-difluorophenyl)-N-(4-(piperidin-4-ylmethoxy)pyrimidin-5-yl)thiazole-4-carboxamide (28)
5-amino-N-(4-(4-aminobutoxy)pyrimidin-5-yl)-2-(2,6-difluorophenyl)thiazole-4-carboxamide (29)
5-amino-2-(2,6-difluorophenyl)-N-(4-(4-hydroxybutoxy)pyrimidin-5-yl)thiazole-4-carboxamide (30)
3-amino-6-(2,6-difluorophenyl)-N-(4-(piperidin-4-yloxy)pyrimidin-5-yl)picolinamide (32)
5-amino-2-(2,6-difluorophenyl)-N-(4-(pyrrolidin-3-yloxy)pyrimidin-5-yl)thiazole-4-carboxamide (34)
2-(2,6-difluorophenyl)-N-(4-(((1S,3R)-3-hydroxycyclopentyl)oxy)pyrimidin-5-yl)thiazole-4-carboxamide (37)
5-amino-2-(2,6-difluorophenyl)-N-(4-(3-hydroxy-3-methylbutoxy)pyrimidin-5-yl)thiazole-4-carboxamide (39)

2-(2,6-difluorophenyl)-N-(4-(3-hydroxy-3-methylbutoxy) pyrimidin-5-yl)thiazole-4-carboxamide (40)

5-amino-2-(2,6-difluorophenyl)-N-(4-(3-hydroxybutoxy) pyrimidin-5-yl)thiazole-4-carboxamide (41)

2-(2,6-difluorophenyl)-N-(4-(3-hydroxybutoxy)pyrimidin-5-yl)thiazole-4-carboxamide (42)

5-amino-2-(2,6-difluorophenyl)-N-(4-((4-hydroxypentyl) oxy)pyrimidin-5-yl)thiazole-4-carboxamide (45)

2-(2,6-difluorophenyl)-N-(4-((4-hydroxypentyl)oxy)pyrimidin-5-yl)thiazole-4-carboxamide (46)

5-amino-2-(2,6-difluorophenyl)-N-(4-((4-hydroxy-4-methylpentyl)oxy)pyrimidin-5-yl)thiazole-4-carboxamide (47)

2-(2,6-difluorophenyl)-N-(4-((4-hydroxy-4-methylpentyl) oxy)pyrimidin-5-yl)thiazole-4-carboxamide (48)

5-amino-2-(2,6-difluorophenyl)-N-(4-(3,4-dihydroxybutoxy)pyrimidin-5-yl)thiazole-4-carboxamide (49)

2-(2,6-difluorophenyl)-N-(4-(3,4-dihydroxybutoxy)pyrimidin-5-yl)thiazole-4-carboxamide (50)

5-amino-2-(2,6-difluorophenyl)-N-(4-(4-(methylamino)butoxy)pyrimidin-5-yl)thiazole-4-carboxamide (52)

5-amino-2-(2,6-difluorophenyl)-N-(4-(piperidin-4-ylthio) pyrimidin-5-yl)thiazole-4-carboxamide (53)

The present invention also provides the methods of synthesis of the above PIM kinase inhibitors.

The compounds in this invention are made from commercial available starting materials and reagents. This invention is illustrated in the following scheme:

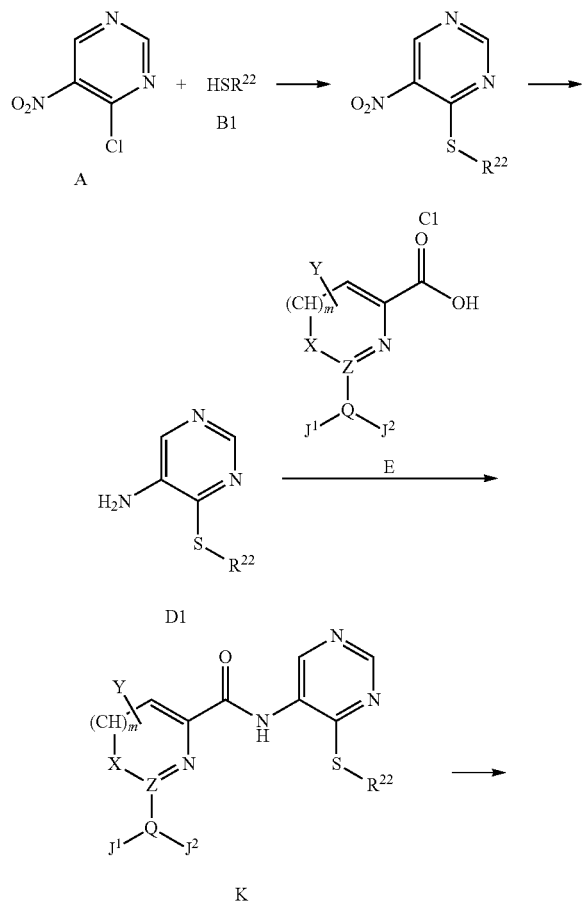

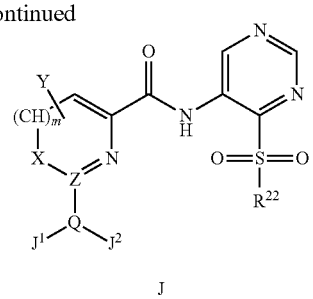

In the above scheme, X, Y, Z, $J^1$, $J^2$, Q, m and $R^{22}$ are the same as defined earlier (1) The general procedure for the synthesis of compounds when E of Formula I is sulfur or sulfone group:

Thiol compound B1 (1 eq.), protected or unprotected, reacts with 4-Chloro-3-nitropyrimidine (A) (1 eq.) in the presence of a base, for example DIEA (N,N-diisopropyethylamine) (3 eq.), in an appropriate solvent, for example dioxane, at 40° C. for 1-16 hours to form thioether C1. C1 (1 eq.) reacts with $Na_2S_2O_4$ (3 Eq.) in the presence of a base, for example saturated $NaHCO_3$ water solution (3 eq.), in an appropriate solvent, for example methanol, at 40° C. for 1-10 hours, and is reduced to aminopyrimidine D1. Protected or unprotected aromatic carboxylic acid E (1 eq.), in the presence of a coupling reagent, for example HATU (1-[bis(dimethylamino) methylene]-1H-1,2,3-triazolo[4,5-b]pyridinium 3-oxid hexafluorophosphate) (1-1.5 eq.), a base, for example DIEA (3 eq.), in a solvent, for example DMF (N,N-dimethyl formaldehyde), at heated conditions, for example 40° C., reacts with amine D1 (1 eq.) for 0.5-8 hours to form thioether K. If there is no protecting group in K, then K is final thioether product of Formula I where E is sulfur group. If K is protected by protecting group, for example BOC (tert-butyloxycarbonyl) or trimethylsilyl group, it's deprotected by treating with mixture of TFA (trifluoroacetic acid) (10-100 eq.) with equal volume of dichloromethane at room temperature (25° C.) for 1-16 hours. The final thioether product K of Formula I is obtained after removing the solvent in vacuo at room temperature (25° C.).

Thioether K (1 eq.) is oxidized by m-CPBA (m-chloroperoxybenzoic acid) (2.2 eq.) in a solvent, for example $CH_2Cl_2$ at room temperature to form sulfone product J. If there is no protecting group in J, then J is final sulfone product of Formula I where E is sulfone group. If J is protected by protecting group, for example BOC or trimethylsilyl group, it's deprotected by treating with mixture of TFA (10-100 eq.) with equal volume of dichloromethane at room temperature (25° C.) for 1-16 hours. The final sulfone product J of Formula I is obtained after removing the solvent in vacuo at room temperature (25° C.).

(2) The general procedure for the synthesis of compounds when E of Formula I is ether group:

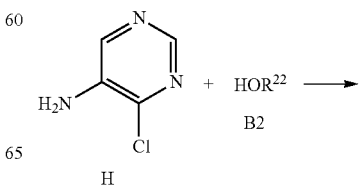

-continued

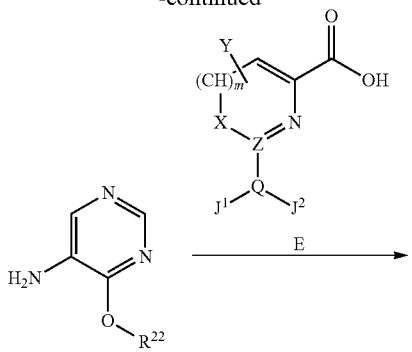

D3

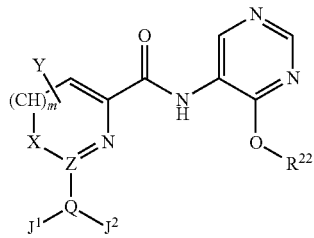

K2

Alcohol B2 (1.1 eq.), protected or unprotected, reacted with a base, for example NaH (1.1 eq.), in a solvent, for example THF, at room temperature (25° C.) for 1 hour, then reacted with 5-amino-4-chloropyrimidine H (1 eq.) at heated conditions, for example 100° C. for 1-10 hours to form aminopyrimidine ether D3. Protected or unprotected aromatic carboxylic acid E (1 eq.), in the presence of a coupling reagent, for example HATU (1-1.5 eq.), a base, for example DIEA (3 eq.), in a solvent, for example DMF, at heated conditions, for example 40° C., reacts with amine D3 (1 eq.) for 0.5-8 hours to form ether K2. If there is no protecting group in K2, then K2 is final ether product of Formula I where E is ether group. If K2 is protected by protecting group, for example BOC or trimethylsilyl group, it's deprotected by treating with mixture of TFA (10-100 eq.) with equal volume of dichloromethane at room temperature (25° C.) for 1-16 hours. The final ether product K2 of Formula I is obtained after removing the solvent in vacuo at room temperature (25° C.).

The present invention also provides the pharmaceutical application of the above PIM kinase inhibitors.

The PIM kinase assays showed that all compounds in all the examples can significantly inhibit the PIM-1 activity. At 3 µM concentration, most compounds showed over 50% inhibition of PIM-1 kinase activity, some as high as 100%. The compounds in the examples also show excellent inhibitory activities against PIM-2 and PIM-3 kinase. At 3 µM concentration, they can inhibit PIM-2 and PIM-3 by as much as 100%. Therefore, the PIM kinase inhibitors in the present invention can be used for pharmaceuticals.

The present invention provides the use of the above PIM kinase inhibitors as drugs to treat or prevent cancers.

The present invention provides the use of the above PIM kinase inhibitors as drugs to treat or prevent autoimmune diseases.

The present invention provides the use of the above PIM kinase inhibitors as drugs to treat or prevent allergic reactions.

The present invention provides the use of the above PIM kinase inhibitors as drugs to treat or prevent atherosclerosis.

The present invention provides the use of the above PIM kinase inhibitors as drugs to treat or prevent organ transplant rejection.

The drugs in present invention use PIM kinase inhibitors as active ingredients along with pharmaceutical carriers and adjuvants.

The present invention provides the new application of PIM kinase inhibitors and has significant clinical value.

EXAMPLES

The following examples are set forth for illustration only to help understand the invention described herein and not to be construed as limiting the present invention in any manner.

Example 1

Synthesis of 2-(2,6-difluorophenyl)-N-(4-(pyrrolidin-3-yloxy)pyrimidin-5-yl)thiazole-4-carboxamide (1)

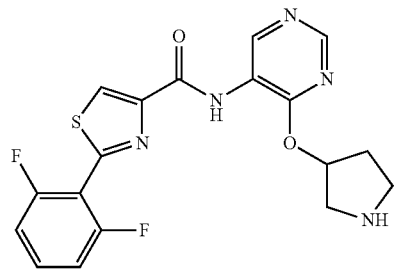 [SMILES: O=C(Nc1cncnc1OC1CCNC1)c1csc(-c2c(F)cccc2F)n1]

(1) Synthesis of tert-butyl 3-((5-aminopyrimidin-4-yl)oxy)pyrrolidine-1-carboxylate (1D3)

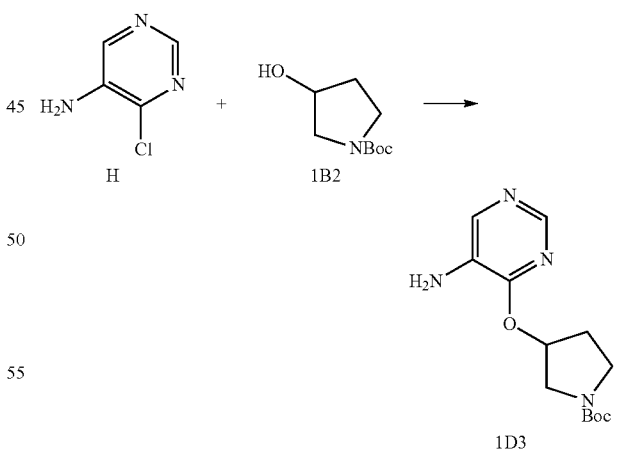

At room temperature, NaH (71 mg, 2.94 mmol) was added to a solution of tert-butyl-3-hydroxypyrrolidine-1-carboxylate (1B2) (500 mg, 2.67 mmol) in THF (tetrahydrofuran) (10 mL) and stirred for 1 hour. 4-chloropyrimidin-5-amine (H) (348 mg, 2.67 mmol) was then added. The reaction mixture was then heated to 100° C. under nitrogen and stirred for 4 hours, cooled to room temperature (20-30° C.) and concentrated in vacuo. The residue was purified with flash column (eluent: 10-30% ethyl acetate/petroleum ether) to obtain the product 1D3 (336 mg, 1.2 mmol).

(2) Synthesis of tert-butyl 3-((5-(2-(2,6-difluorophenyl)thiazole-4-carboxamido)pyrimidin-4-yl)oxy)pyrrolidine-1-carboxylate (1A)

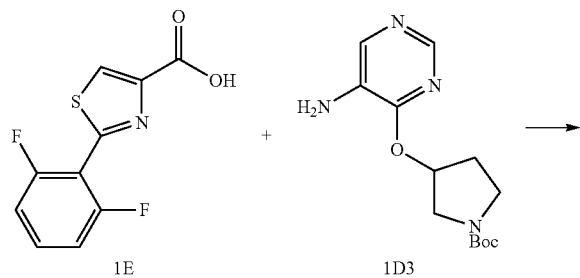

1E    1D3

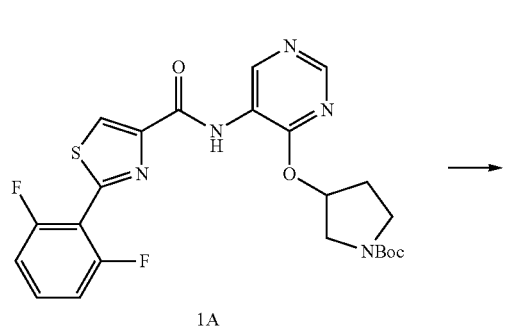

1A

Compound (1D3) (47 mg, 0.169 mmol), 2-(2,6-difluorophenyl)thiazole-4-carboxylic acid (1E) (40 mg, 0.169 mmol, HATU (77 mg, 0.203 mmol) and DIEA (93 μL, 0.507 mmol) are mixed in DMF (5 mL) and stirred at 50° C. for 1 hour. The reaction mixture was cooled to room temperature and diluted with ethyl acetate (50 mL), washed with brine, dried over Na₂SO₄ and concentrated in vacuo. The residue was purified with flash column (eluent: 10-30% ethyl acetate/petroleum ether) to obtain the product 1A (30 mg, 0.0596 mmol)

(3) Synthesis of 2-(2,6-difluorophenyl)-N-(4-(pyrrolidin-3-yloxy)pyrimidin-5-yl)thiazole-4-carboxamide (1)

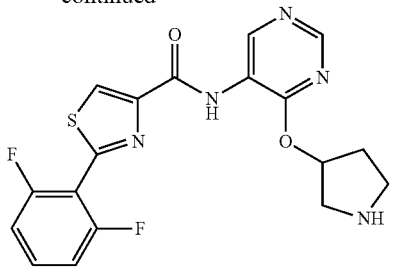

1

At room temperature, TFA (trifluoroacetic acid) (0.5 mL) was added to a solution of Compound 1A (20 mg, 0.0394 mmol) in CH₂Cl₂ (1 mL) and stirred for 10 min. The mixture was the concentrated in vacuo. The residue was dissolved in CH₂Cl₂ (10 mL) and washed with NaOH (5 mL) and brine (5 mL), dried over Na₂SO₄ and concentrated in vacuo to obtain the title compound 1 (12 mg, 0.0298 mmol)

Example 2

Synthesis of N-(4-(azepan-4-yloxy)pyrimidin-5-yl)-2-(2,6-difluorophenyl)thiazole-4-carboxamide (2)

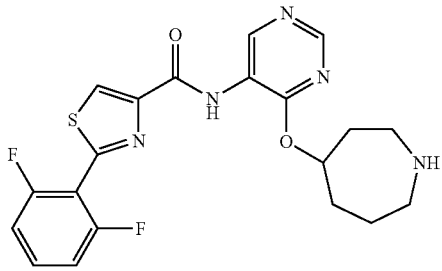 [SMILES: O=C(Nc1cncnc1OC1CCCNCC1)c1csc(-c2c(F)cccc2F)n1]

Following the procedure described in Example 1, and substituting compound 1B2 in Step (1) with tert-butyl 4-hydroxyazepane-1-carboxylate (2B2), the title compound 2 (17 mg, 0.039 mmol) was obtained.

Example 3

Synthesis of 2-(2,6-difluorophenyl)-N-(4-(piperidin-4-yloxy)pyrimidin-5-yl)thiazole-4-carboxamide (3)

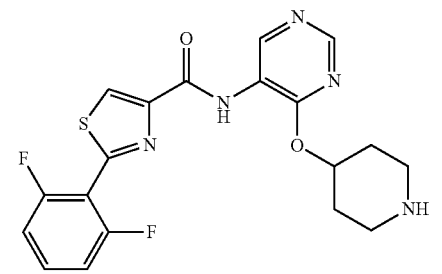 [SMILES: O=C(Nc1cncnc1OC1CCNCC1)c1csc(-c2c(F)cccc2F)n1]

Following the procedure described in Example 1, and substituting compound 1B2 in Step (1) with tert-butyl 4-hydroxypiperidine-1-carboxylate (3B2) (250 mg, 1.276 mmol), the title compound 3 (22 mg, 0.0526 mmol) was obtained.

Example 4

Synthesis of 5-amino-2-(2,6-difluorophenyl)-N-(4-(piperidin-4-yloxy)pyrimidin-5-yl)thiazole-4-carboxamide (4)

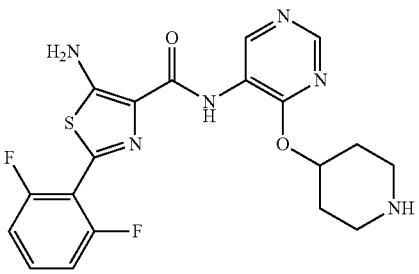 [SMILES: Nc1sc(-c2c(F)cccc2F)nc1C(=O)Nc1cncnc1OC1CCNCC1]

Following the procedure described in Example 3, and substituting Compound 1E in Step (2) with 5-amino-2-(2,6-difluorophenyl)thiazole-4-carboxylic acid (2E) (40 mg, 0.156 mmol), the title compound 4 (18 mg, 0.0431 mmol) was obtained

Example 5

Synthesis of 2-(2,6-difluorophenyl)-N-(4-((4-hydroxycyclohexyl)oxy)pyrimidin-5-yl)thiazole-4-carboxamide (5)

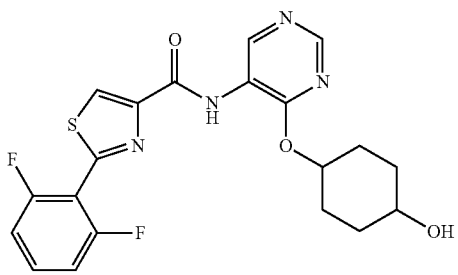 [SMILES: O=C(Nc1cncnc1OC1CCC(O)CC1)c1csc(-c2c(F)cccc2F)n1]

Following the procedure described in Step (1) and Step (2) of Example 1, and substituting the Compound 1B2 in Step (1) with cyclohexane-1,4-diol (5B2) (250 mg, 1.47 mmol), the title compound 5 (16 mg, 0.0370 mmol) was obtained

Example 6

Synthesis of 2-(2,6-difluorophenyl)-N-(4-(oxetan-3-yloxy)pyrimidin-5-yl)thiazole-4-carboxamide (6)

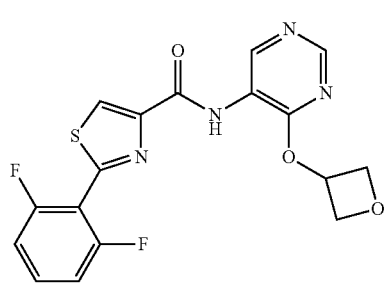 [SMILES: O=C(Nc1cncnc1OC1COC1)c1csc(-c2c(F)cccc2F)n1]

Following the procedure described in Example 5, and substituting Compound 1B2 in Step (1) with oxetan-3-ol (6B2) (125 mg, 1.69 mmol), the title compound 6 (23 mg, 0.0588 mmol) was obtained

Example 7

Synthesis of 2-(2,6-difluorophenyl)-N-(4-((3-hydroxycyclopentyl)oxy)pyrimidin-5-yl)thiazole-4-carboxamide (7)

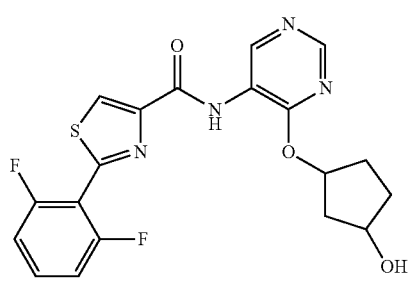 [SMILES: O=C(Nc1cncnc1OC1CCC(O)C1)c1csc(-c2c(F)cccc2F)n1]

Following the procedure described in Example 5, and substituting Compound 5B2 in Step (1) with cyclopentane-1,3-diol (7B2) (125 mg, 1.23 mmol), the title compound 7 (17 mg, 0.0406 mmol) was obtained.

Example 8

Synthesis of 2-(2,6-difluorophenyl)-N-(4-((2,2,6,6-tetramethylpiperidin-4-yl)oxy)pyrimidin-5-yl)thiazole-4-carboxamide (8)

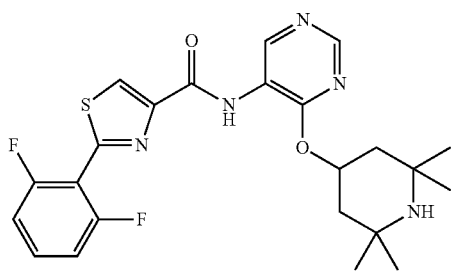 [SMILES: CC1(C)CC(Oc2ncncc2NC(=O)c2csc(-c3c(F)cccc3F)n2)CC(C)(C)N1]

Following the procedure described in Example 1, and substituting Compound 1B2 in Step (1) with tert-butyl 4-hydroxy-2,2,6,6-tetramethylpiperidine-1-carboxylate (8B2) (250 mg, 1.09 mmol), the title compound 8 (24 mg, 0.0507 mmol) was obtained.

Example 9

Synthesis of 2-(2,6-difluorophenyl)-N-(4-((3-methyloxetan-3-yl)methoxy)pyrimidin-5-yl)thiazole-4-carboxamide (9)

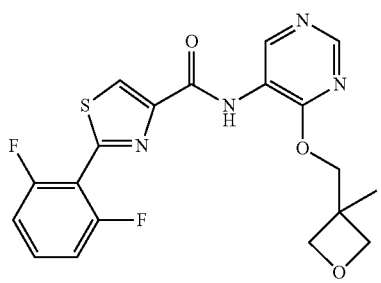 [SMILES: CC1(COc2ncncc2NC(=O)c2csc(-c3c(F)cccc3F)n2)COC1]

Following the procedure described in Example 5, and substituting Compound 5B2 in Step (1) with (3-methyloxetan-3-yl)methanol (9B2) (125 mg, 1.23 mmol), the title compound 9 (25 mg, 0.0571 mmol) was obtained.

Example 10

Synthesis of N-(4-(azetidin-3-ylmethoxy)pyrimidin-5-yl)-2-(2,6-difluorophenyl)thiazole-4-carboxamide (10)

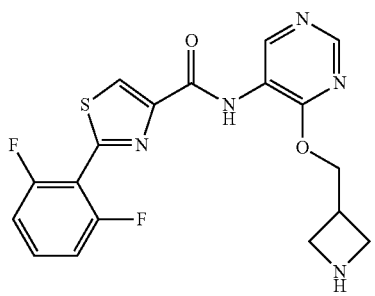 [SMILES: O=C(Nc1cncnc1OCC1CNC1)c1csc(-c2c(F)cccc2F)n1]

Following the procedure described in Example 1, and substituting Compound 1B2 in Step (1) with tert-butyl 3-(hydroxymethyl)azetidine-1-carboxylate (10B2) (250 mg, 1.30 mmol), the title compound 10 (14 mg, 0.0347 mmol) was obtained.

Example 11

Synthesis of 6-(2,6-difluorophenyl)-N-(4-(piperidin-4-yloxy)pyrimidin-5-yl)picolinamide (11)

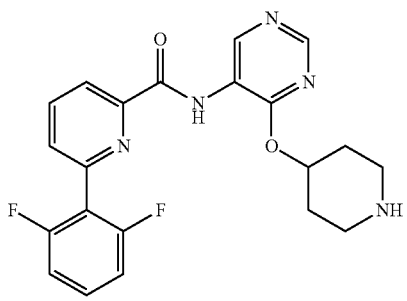 [SMILES: O=C(Nc1cncnc1OC1CCNCC1)c1cccc(-c2c(F)cccc2F)n1]

Following the procedure described in Example 3, and substituting Compound 1E in Step (2) with 6-(2,6-difluorophenyl)picolinic acid (11E) (40 mg, 0.170 mmol), the title compound 11 (19 mg, 0.0462 mmol) was obtained Example 12

Synthesis of 2-(2,6-difluorophenyl)-N-(4-((tetrahydrofuran-3-yl)methoxy)pyrimidin-5-yl)thiazole-4-carboxamide (12)

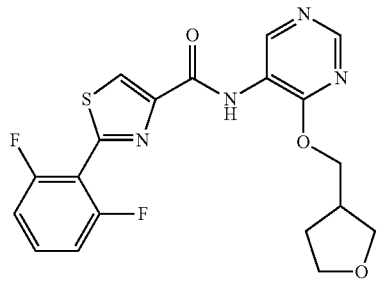 [SMILES: O=C(Nc1cncnc1OCC1CCOC1)c1csc(-c2c(F)cccc2F)n1]

Following the procedure described in Example 5, and substituting Compound 5B2 in Step (1) with (tetrahydrofuran-3-yl)methanol (12B2) (30 mg, 0.294 mmol), the title compound 12 (12 mg, 0.0286 mmol) was obtained.

Example 13

Synthesis of 2-(2,6-difluorophenyl)-N-(4-((tetrahydro-2H-pyran-4-yl)methoxy)pyrimidin-5-yl)thiazole-4-carboxamide (13)

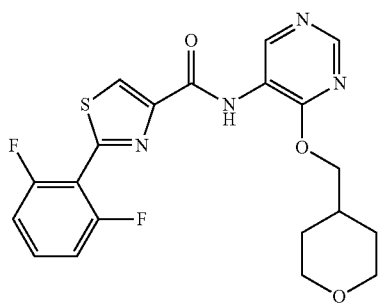 [SMILES: O=C(Nc1cncnc1OCC1CCOCC1)c1csc(-c2c(F)cccc2F)n1]

Following the procedure described in Example 5, and substituting Compound 5B2 in Step (1) with (tetrahydro-2H-pyran-4-yl)methanol (13B2) (30 mg, 0.259 mmol), the title compound 13 (12 mg, 0.0286 mmol) was obtained Example 14

Synthesis of N-(4-(8-azabicyclo[3.2.1]octan-3-yloxy)pyrimidin-5-yl)-2-(2,6-difluorophenyl)thiazole-4-carboxamide (14)

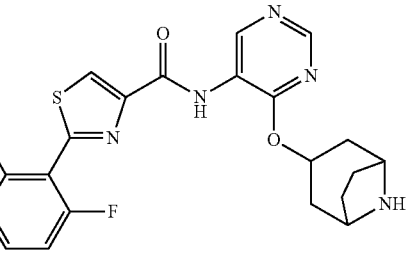

Following the procedure described in Example 1, and substituting Compound 1B2 in Step (1) with tert-butyl 3-hydroxy-8-azabicyclo[3.2.1]octane-8-carboxylate (14B2) (250 mg, 1.10 mmol), the title compound 14 (14 mg, 0.0347 mmol) was obtained

Example 15

Synthesis of 2-(2,6-difluorophenyl)-N-(4-(piperidin-4-ylmethoxy)pyrimidin-5-yl)thiazole-4-carboxamide (15)

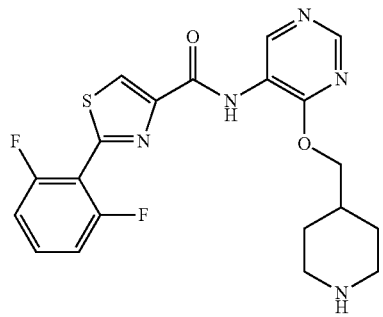 [SMILES: O=C(Nc1cncnc1OCC1CCNCC1)c1csc(-c2c(F)cccc2F)n1]

Following the procedure described in Example 1, and substituting Compound 1B2 in Step (1) with tert-butyl 4-(hydroxymethyl)piperidine-1-carboxylate (15B2) (250 mg, 1.16 mmol), the title compound 15 (12 mg, 0.0278 mmol) was obtained.

Example 16

Synthesis of 2-(2,6-difluorophenyl)-N-(4-((tetrahydro-2H-pyran-4-yl)oxy)pyrimidin-5-yl)thiazole-4-carboxamide (16)

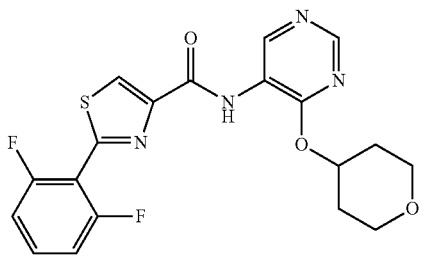 [SMILES: O=C(Nc1cncnc1OC1CCOCC1)c1csc(-c2c(F)cccc2F)n1]

Following the procedure described in Example 5, and substituting Compound 5B2 in Step (1) with tetrahydro-2H-pyran-4-ol (16B2) (30 mg, 0.290 mmol), the title compound 16 (17 mg, 0.0406 mmol) was obtained.

Example 17

Synthesis of N-(4-(3-azabicyclo[3.2.0]heptan-6-yloxy)pyrimidin-5-yl)-2-(2,6-difluorophenyl)thiazole-4-carboxamide (17)

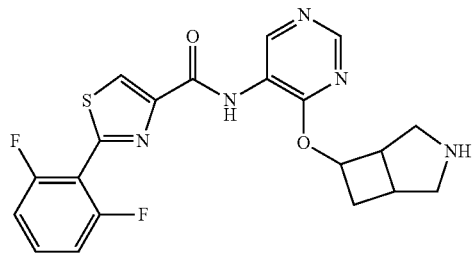 [SMILES: O=C(Nc1cncnc1OC1CC2CNCC21)c1csc(-c2c(F)cccc2F)n1]

Following the procedure described in Example 1, and substituting Compound 1B2 in Step (1) with tert-butyl 6-hydroxy-3-azabicyclo[3.2.0]heptane-3-carboxylate (17B2) (250 mg, 1.17 mmol), the title compound 17 (16 mg, 0.0372 mmol) was obtained

Example 18

Synthesis of 2-(2,6-difluorophenyl)-N-(4-(pyrrolidin-3-ylmethoxy)pyrimidin-5-yl)thiazole-4-carboxamide (18)

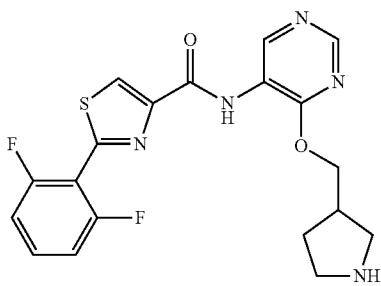 [SMILES: O=C(Nc1cncnc1OCC1CCNC1)c1csc(-c2c(F)cccc2F)n1]

Following the procedure described in Example 1, and substituting Compound 1B2 in Step (1) with tert-butyl 3-(hydroxymethyl)pyrrolidine-1-carboxylate (18B2) (250 mg, 1.24 mmol), the title compound 18 (22 mg, 0.0526 mmol) was obtained.

Example 19

Synthesis of 2-(2,6-difluorophenyl)-N-(4-(quinuclidin-3-ylmethoxy)pyrimidin-5-yl)thiazole-4-carboxamide (19)

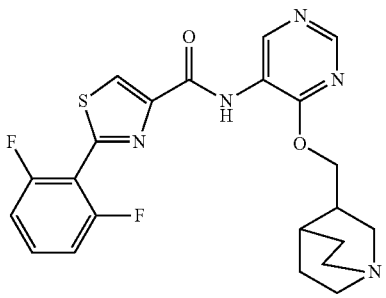 [SMILES: O=C(Nc1cncnc1OCC1CN2CCC1CC2)c1csc(-c2c(F)cccc2F)n1]

Following the procedure described in Example 5, and substituting Compound 5B2 in Step (1) with quinuclidin-3-ylmethanol (19B2) (30 mg, 0.214 mmol), the title compound 19 (15 mg, 0.0328 mmol) was obtained

Example 20

Synthesis of 3-amino-6-(2,6-difluorophenyl)-N-(4-((3-methyloxetan-3-yl)methoxy)pyrimidin-5-yl)picolinamide (20)

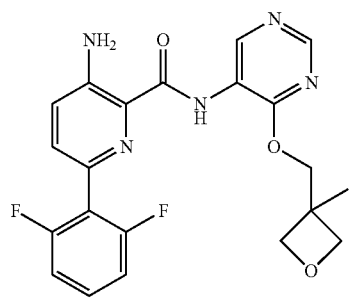 [SMILES: CC1(COc2ncncc2NC(=O)c2nc(-c3c(F)cccc3F)ccc2N)COC1]

Following the procedure described in Example 9, and substituting Compound 1E in Step (2) with 3-amino-6-(2,6-difluorophenyl)picolinic acid (20E) (40 mg, 0.160 mmol), the title compound 20 (20 mg, 0.0467 mmol) was obtained.

Example 21

Synthesis of N-(4-(azetidin-3-yloxy)pyrimidin-5-yl)-2-(2,6-difluorophenyl)thiazole-4-carboxamide (21)

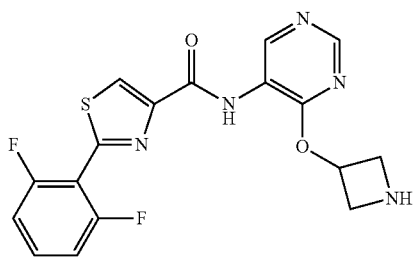 [SMILES: O=C(Nc1cncnc1OC1CNC1)c1csc(-c2c(F)cccc2F)n1]

Following the procedure described in Example 1, and substituting Compound 1B2 in Step (1) with tert-butyl 3-hydroxyazetidine-1-carboxylate (21B2) (250 mg, 1.45 mmol), the title compound 21 (10 mg, 0.0256 mmol) was obtained.

Example 22

Synthesis of 2-(2,6-difluorophenyl)-N-(4-(piperidin-3-yloxy)pyrimidin-5-yl)thiazole-4-carboxamide (22)

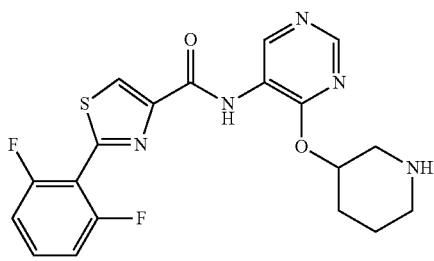 [SMILES: O=C(Nc1cncnc1OC1CCCNC1)c1csc(-c2c(F)cccc2F)n1]

Following the procedure described in Example 1, and substituting Compound 1B2 in Step (1) with tert-butyl 3-hydroxypiperidine-1-carboxylate (22B2) (250 mg, 1.24 mmol), the title compound 22 (13 mg, 0.0311 mmol) was obtained.

Example 23

Synthesis of 5-(2,6-difluorophenyl)-N-(4-(piperidin-4-ylmethoxy)pyrimidin-5-yl)thiophene-2-carboxamide (23)

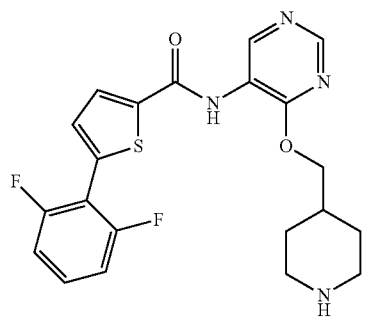 [SMILES: O=C(Nc1cncnc1OCC1CCNCC1)c1ccc(-c2c(F)cccc2F)s1]

Following the procedure described in Example 15, and substituting Compound 1E in Step (2) with 5-(2,6-difluorophenyl)thiophene-2-carboxylic acid (23E) (40 mg, 0.170 mmol), the title compound 23 (40 mg, 0.170 mmol) was obtained.

Example 24

Synthesis of N-(4-((cis-4-aminocyclohexyl)oxy)pyrimidin-5-yl)-2-(2,6-difluorophenyl)thiazole-4-carboxamide (24)

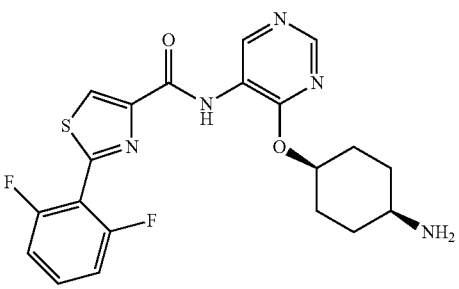

Following the procedure described in Example 1, and substituting Compound 1B2 in Step (1) with tert-butyl(cis-4-hydroxycyclohexyl)carbamate (24B2) (250 mg, 1.16 mmol), the title compound 24 (13 mg, 0.0311 mmol) was obtained.

Example 25

Synthesis of 5-amino-2-(2,6-difluorophenyl)-N-(4-((3-methyloxetan-3-yl)methoxy)pyrimidin-5-yl)thiazole-4-carboxamide (25)

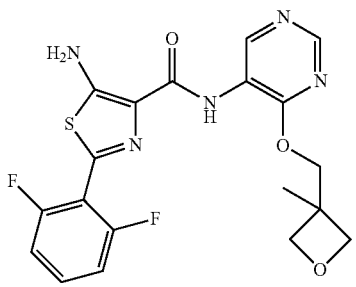 [SMILES: CC1(COc2ncncc2NC(=O)c2nc(-c3c(F)cccc3F)sc2N)COC1]

Following the procedure described in Example 9, and substituting Compound 1E in Step (2) with 5-amino-2-(2,6-difluorophenyl)thiazole-4-carboxylic acid (2E) (40 mg, 0.156 mmol), the title compound 25 (27 mg, 0.0644 mmol) was obtained.

Example 26

Synthesis of 5-amino-N-(4-(azepan-4-yloxy)pyrimidin-5-yl)-2-(2,6-difluorophenyl)thiazole-4-carboxamide (26)

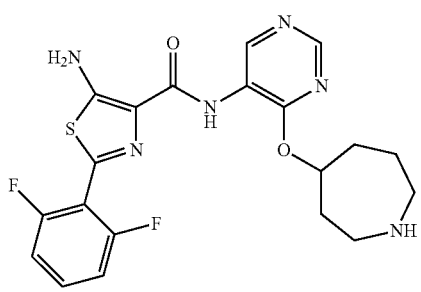 [SMILES: Nc1sc(-c2c(F)cccc2F)nc1C(=O)Nc1cncnc1OC1CCCNCC1]

Following the procedure described in Example 2, and substituting Compound 1E in Step (2) with 5-amino-2-(2,6-difluorophenyl)thiazole-4-carboxylic acid (2E) (40 mg, 0.156 mmol), the title compound 26 (17 mg, 0.0380 mmol) was obtained.

Example 27

Synthesis of 5-amino-N-(4-((trans-4-aminocyclohexyl)oxy)pyrimidin-5-yl)-2-(2,6-difluorophenyl)thiazole-4-carboxamide (27)

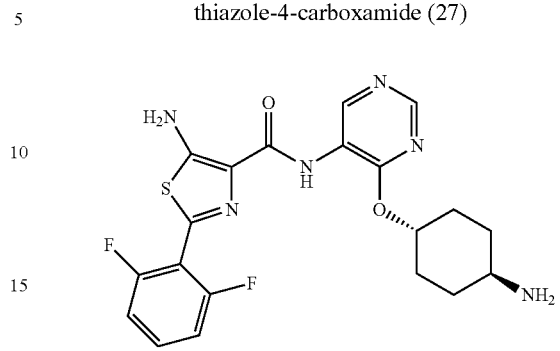

Following the procedure described in Example 4, and substituting Compound 3B2 in Step (1) with tert-butyl(trans-4-hydroxycyclohexyl)carbamate (27B2) (250 mg, 1.16 mmol), the title compound 27 (16 mg, 0.0358 mmol) was obtained.

Example 28

Synthesis of 5-amino-2-(2,6-difluorophenyl)-N-(4-(piperidin-4-ylmethoxy)pyrimidin-5-yl)thiazole-4-carboxamide (28)

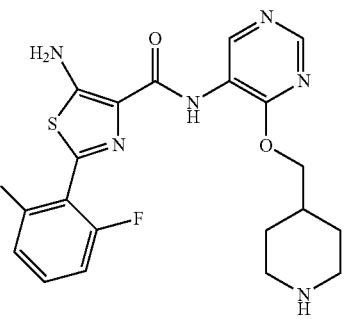

Following the procedure described in Example 15, and substituting Compound 1E in Step (2) with 5-amino-2-(2,6-difluorophenyl)thiazole-4-carboxylic acid (2E) (40 mg, 0.156 mmol), the title compound 28 (21 mg, 0.0470 mmol) was obtained.

Example 29

Synthesis of 5-amino-N-(4-(4-aminobutoxy)pyrimidin-5-yl)-2-(2,6-difluorophenyl)thiazole-4-carboxamide (29)

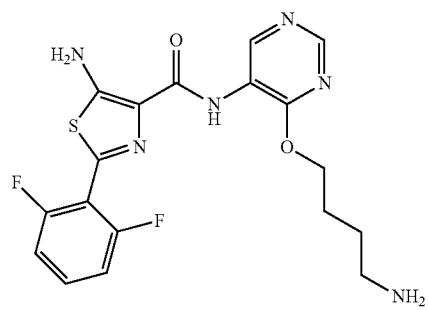

Following the procedure described in Example 4, and substituting Compound 3B2 in Step (1) with tert-butyl (4-hydroxybutyl)carbamate (29B2) (100 mg, 0.529 mmol), the title compound 29 (30 mg, 0.0713 mmol) was obtained.

Example 30

Synthesis of 5-amino-2-(2,6-difluorophenyl)-N-(4-(4-hydroxybutoxy)pyrimidin-5-yl)thiazole-4-carboxamide (30)

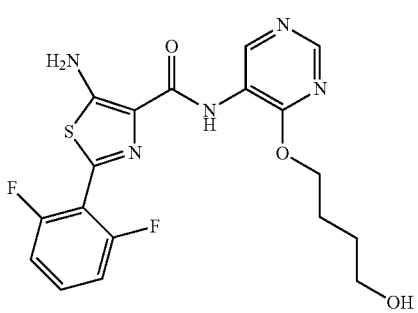 [SMILES: Nc1sc(-c2c(F)cccc2F)nc1C(=O)Nc1cncnc1OCCCCO]

Following the procedure described in Example 1, and substituting Compound 4 in Step (1) with 4-(((trimethylsilyl)oxy)butan-1-ol (30B2) (100 mg, 0.617 mmol), the title compound 30 (32 mg, 0.0760 mmol) was obtained.

Example 31

Synthesis of 2-(2,6-difluorophenyl)-N-(4-(((3S,4R)-3-fluoropiperidin-4-yl)oxy)pyrimidin-5-yl)thiazole-4-carboxamide (31)

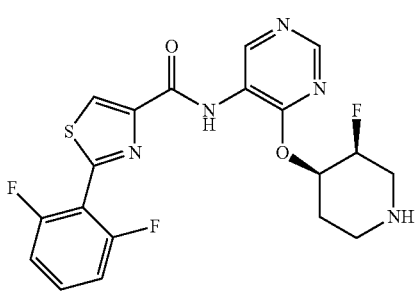

Following the procedure described in Example 1, and substituting Compound 1B2 in Step (1) with (3S,4R)-tert-butyl 3-fluoro-4-hydroxypiperidine-1-carboxylate (31B2) (250 mg, 1.14 mmol), the title compound 31 (16 mg, 0.0367 mmol) was obtained.

Example 32

Synthesis of 3-amino-6-(2,6-difluorophenyl)-N-(4-(piperidin-4-yloxy)pyrimidin-5-yl)picolinamide (32)

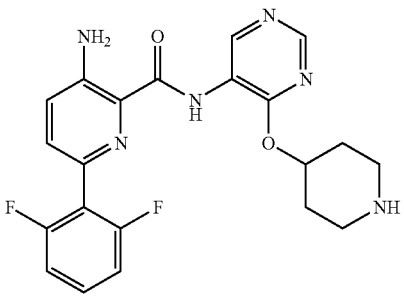 [SMILES: Nc1ccc(-c2c(F)cccc2F)nc1C(=O)Nc1cncnc1OC1CCNCC1]

Following the procedure described in Example 3, and substituting Compound 1E in Step (2) with 3-amino-6-(2,6-difluorophenyl)picolinic acid (20E) (40 mg, 0.156 mmol), the title compound 32 (23 mg, 0.0539 mmol) was obtained.

Example 33

Synthesis of 2-isopropyl-N-(4-(piperidin-4-yloxy)pyrimidin-5-yl)thiazole-4-carboxamide (33)

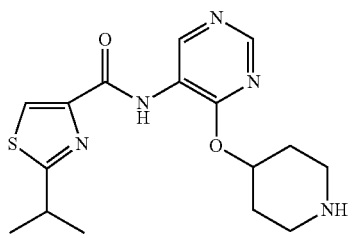 [SMILES: CC(C)c1nc(C(=O)Nc2cncnc2OC2CCNCC2)cs1]

Following the procedure described in Example 3, and substituting Compound 1E in Step (2) with 2-isopropylthiazole-4-carboxylic acid (33E) (40 mg, 0.234 mmol), the title compound 33 (27 mg, 0.0776 mmol) was obtained.

Example 34

Synthesis of 5-amino-2-(2,6-difluorophenyl)-N-(4-(pyrrolidin-3-yloxy)pyrimidin-5-yl)thiazole-4-carboxamide (34)

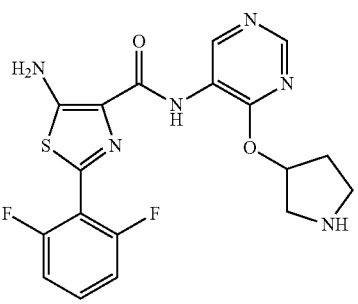 [SMILES: Nc1sc(-c2c(F)cccc2F)nc1C(=O)Nc1cncnc1OC1CCNC1]

Following the procedure described in Example 1, and substituting Compound 1E in Step (2) with 5-amino-2-(2,6-difluorophenyl)thiazole-4-carboxylic acid (2E) (40 mg, 0.156 mmol), the title compound 34 (18 mg, 0.0430 mmol) was obtained.

Example 35

Synthesis of 5-amino-2-(2,6-difluorophenyl)-N-(4-((3-hydroxypropyl)thio)pyrimidin-5-yl)thiazole-4-carboxamide (35)

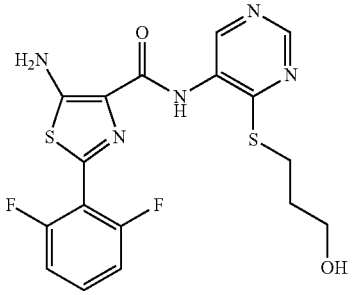 [SMILES: Nc1sc(-c2c(F)cccc2F)nc1C(=O)Nc1cncnc1SCCCO]

(1) Synthesis of 3-((5-aminopyrimidin-4-yl)thio)propan-1-ol (35C1)

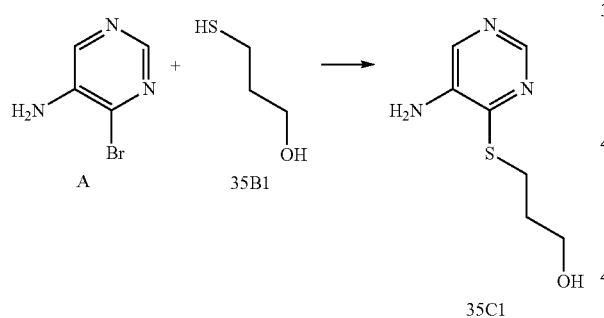

DIEA (1.11 g, 8.61 mmol) was added to a solution of 4-bromopyrimidin-5-amine (A) (1.0 g, 5.74 mmol) and 3-mercaptopropan-1-ol (35B1) (0.53 g, 5.74 mmol) in dioxane (5 mL). The reaction mixture was heated to 50° C. under nitrogen and stirred for 30 min. The LC/MS spectrum showed that the reaction had completed. Water (50 mL) was added and a solid precipitated. The off white solid product (35C1) (913 mg, 4.93 mmol) was obtained after filtration and air drying at 25° C.

(2) Synthesis of 5-amino-2-(2,6-difluorophenyl)-N-(4-((3-hydroxypropyl)thio)pyrimidin-5-yl)thiazole-4-carboxamide (35)

Following the procedure described in Example 1, and substituting Compound 1D3 in Step (2) with 3-((5-aminopyrimidin-4-yl)thio)propan-1-ol (35C1) (29 mg, 0.156 mmol), the title compound 35 (23 mg, 0.0545 mmol) was obtained.

Example 36

Synthesis of 5-amino-2-(2,6-difluorophenyl)-N-(4-((2,2-dimethyl-1,3-dioxolan-4-yl)methoxy)pyrimidin-5-yl)thiazole-4-carboxamide (36)

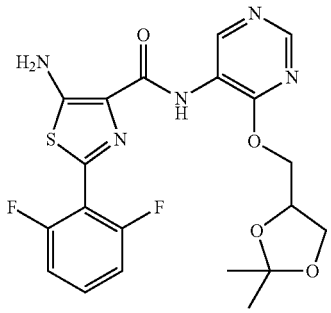 [SMILES: CC1(C)OCC(COc2ncncc2NC(=O)c2nc(-c3c(F)cccc3F)sc2N)O1]

Following the procedure described in Example 25, and substituting Compound 9B2 in Step (1) with (2,2-dimethyl-1,3-dioxolan-4-yl)methanol (36B2) (100 mg, 0.758 mmol), the title compound 36 (27 mg, 0.0646 mmol) was obtained.

Example 37

Synthesis of 2-(2,6-difluorophenyl)-N-(4-(((1S,3R)-3-hydroxycyclopentyl)oxy)pyrimidin-5-yl)thiazole-4-carboxamide (37)

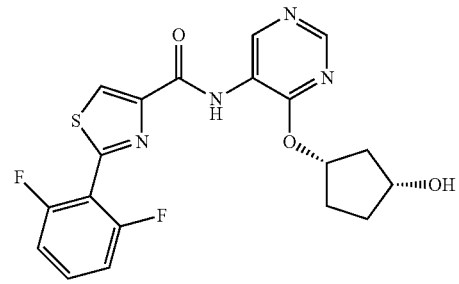 [SMILES: O=C(Nc1cncnc1O[C@H]1CC[C@@H](O)C1)c1csc(-c2c(F)cccc2F)n1]

Following the procedure described in Example 5, and substituting Compound 5B2 in Step (1) with (1R,3S)-cyclopentane-1,3-diol (37B2) (100 mg, 0.980 mmol), the title compound 37 (14 mg, 0.0335 mmol) was obtained.

Example 38

Synthesis of 5-amino-2-(2,6-difluorophenyl)-N-(4-(2-(2,2-dimethyl-1,3-dioxolan-4-yl)ethoxy)pyrimidin-5-yl)thiazole-4-carboxamide (38)

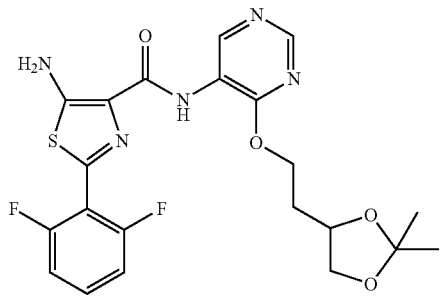 [SMILES: CC1(C)OCC(CCOc2ncncc2NC(=O)c2nc(-c3c(F)cccc3F)sc2N)O1]

Following the procedure described in Example 25, and substituting Compound 9B2 in Step (1) with 2-(2,2-dimethyl-1,3-dioxolan-4-yl)ethanol (38B2) (100 mg, 0.684 mmol), the title compound 38 (21 mg, 0.0440 mmol) was obtained.

Example 39

Synthesis of 5-amino-2-(2,6-difluorophenyl)-N-(4-(3-hydroxy-3-methylbutoxy)pyrimidin-5-yl)thiazole-4-carboxamide (39)

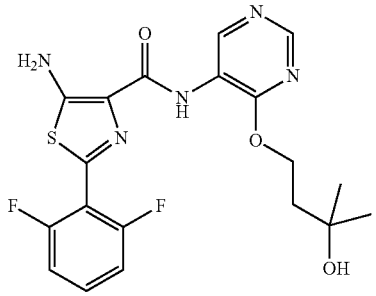 [SMILES: CC(C)(O)CCOc1ncncc1NC(=O)c1nc(-c2c(F)cccc2F)sc1N]

Following the procedure described in Example 25, and substituting Compound 9B2 in Step (1) with 3-methylbutane-1,3-diol (39B2) (100 mg, 0.960 mmol), the title compound 39 (18 mg, 0.0414 mmol) was obtained.

Example 40

Synthesis of 2-(2,6-difluorophenyl)-N-(4-(3-hydroxy-3-methylbutoxy)pyrimidin-5-yl)thiazole-4-carboxamide (40)

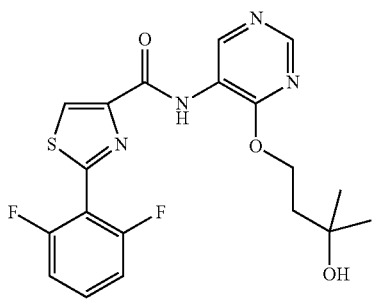 [SMILES: CC(C)(O)CCOc1ncncc1NC(=O)c1csc(-c2c(F)cccc2F)n1]

Following the procedure described in Example 5, and substituting Compound 5B2 in Step (1) with 3-methylbutane-1,3-diol (39B2) (100 mg, 0.960 mmol), the title compound 40 (24 mg, 0.0571 mmol) was obtained.

Example 41

Synthesis of 5-amino-2-(2,6-difluorophenyl)-N-(4-(3-hydroxybutoxy)pyrimidin-5-yl)thiazole-4-carboxamide (41)

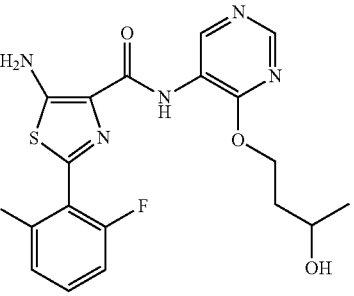

Following the procedure described in Example 25, and substituting Compound 9B2 in Step (1) with butane-1,3-diol (41B2) (100 mg, 1.11 mmol), the title compound 41 (11 mg, 0.0261 mmol) was obtained.

Example 42

Synthesis of 2-(2,6-difluorophenyl)-N-(4-(3-hydroxybutoxy)pyrimidin-5-yl)thiazole-4-carboxamide (42)

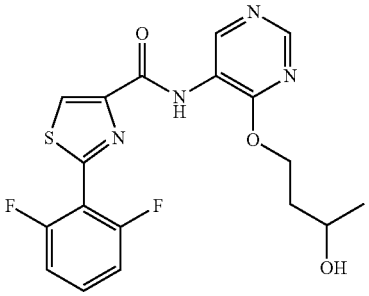 [SMILES: CC(O)CCOc1ncncc1NC(=O)c1csc(-c2c(F)cccc2F)n1]

Following the procedure described in Example 5, and substituting Compound 5B2 in Step (1) with butane-1,3-diol (41B2) (100 mg, 1.11 mmol), the title compound 42 (24 mg, 0.0571 mmol) was obtained.

Example 43

Synthesis of 5-amino-N-(4-((4-carbamoylcyclohexyl)oxy)pyrimidin-5-yl)-2-(2,6-difluorophenyl)thiazole-4-carboxamide (43)

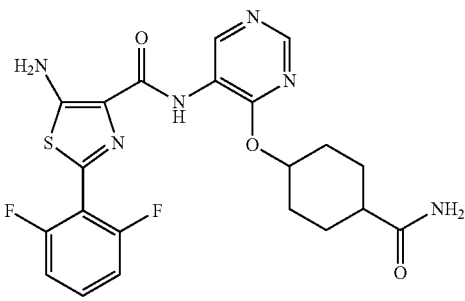 [SMILES: NC(=O)C1CCC(Oc2ncncc2NC(=O)c2nc(-c3c(F)cccc3F)sc2N)CC1]

Following the procedure described in Example 25, and substituting Compound 9B2 in Step (1) with 4-hydroxycyclohexanecarboxamide (43B2) (100 mg, 0.699 mmol), the title compound 43 (12 mg, 0.0253 mmol) was obtained.

Example 44

Synthesis of 5-amino-2-(2,6-difluorophenyl)-N-(4-(2-hydroxyethoxy)pyrimidin-5-yl)thiazole-4-carboxamide (44)

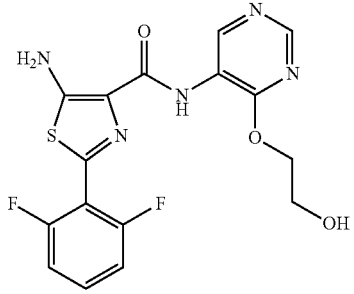 [SMILES: Nc1sc(-c2c(F)cccc2F)nc1C(=O)Nc1cncnc1OCCO]

Following the procedure described in Example 4, and substituting Compound 3B2 in Step (1) with 2-((trimethylsilyl)oxy)ethanol (44B2) (100 mg, 0.746 mmol), the title compound 44 (29 mg, 0.0738 mmol) was obtained.

Example 45

Synthesis of 5-amino-2-(2,6-difluorophenyl)-N-(4-((4-hydroxypentyl)oxy)pyrimidin-5-yl)thiazole-4-carboxamide (45)

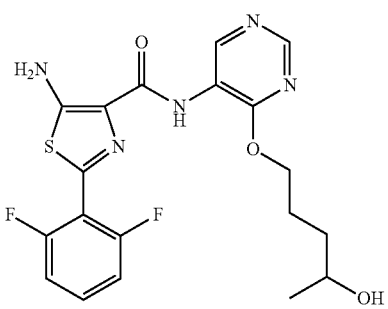 [SMILES: CC(O)CCCOc1ncncc1NC(=O)c1nc(-c2c(F)cccc2F)sc1N]

Following the procedure described in Example 25, and substituting Compound 9B2 in Step (1) with pentane-1,4-diol (45B2) (100 mg, 0.960 mmol), the title compound 45 (22 mg, 0.0506 mmol) was obtained.

Example 46

Synthesis of 2-(2,6-difluorophenyl)-N-(4-((4-hydroxypentyl)oxy)pyrimidin-5-yl)thiazole-4-carboxamide (46)

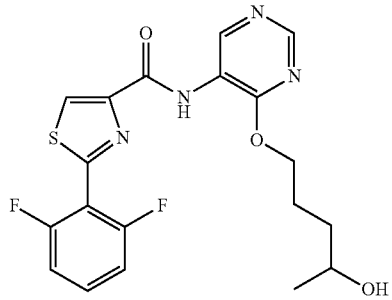 [SMILES: CC(O)CCCOc1ncncc1NC(=O)c1csc(-c2c(F)cccc2F)n1]

Following the procedure described in Example 5, and substituting Compound 5B2 in Step (1) with pentane-1,4-diol (45B2) (100 mg, 0.960 mmol), the title compound 46 (26 mg, 0.0619 mmol) was obtained.

Example 47

Synthesis of 5-amino-2-(2,6-difluorophenyl)-N-(4-((4-hydroxy-4-methylpentyl)oxy)pyrimidin-5-yl)thiazole-4-carboxamide (47)

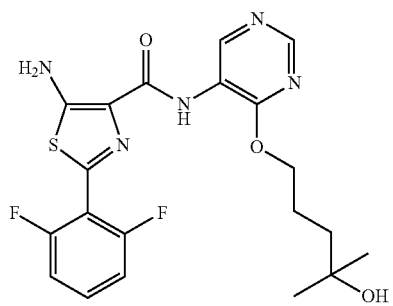 [SMILES: CC(C)(O)CCCOc1ncncc1NC(=O)c1nc(-c2c(F)cccc2F)sc1N]

Following the procedure described in Example 25, and substituting Compound 9B2 in Step (1) with 4-methylpentane-1,4-diol (47B2) (100 mg, 0.848 mmol), the title compound 47 (23 mg, 0.0512 mmol) was obtained.

Example 48

Synthesis of 2-(2,6-difluorophenyl)-N-(4-((4-hydroxy-4-methylpentyl)oxy)pyrimidin-5-yl)thiazole-4-carboxamide (48)

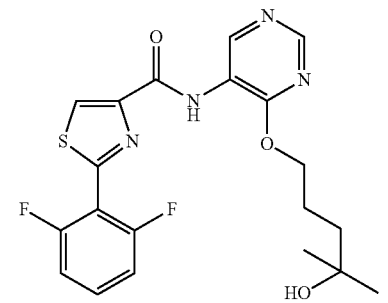 [SMILES: CC(C)(O)CCCOc1ncncc1NC(=O)c1csc(-c2c(F)cccc2F)n1]

Following the procedure described in Example 5, and substituting Compound 5B2 in Step (1) with 4-methylpentane-1,4-diol (48B2) (100 mg, 0.848 mmol), the title compound 48 (25 mg, 0.0576 mmol) was obtained.

Example 49

Synthesis of 5-amino-2-(2,6-difluorophenyl)-N-(4-(3,4-dihydroxybutoxy)pyrimidin-5-yl)thiazole-4-carboxamide (49)

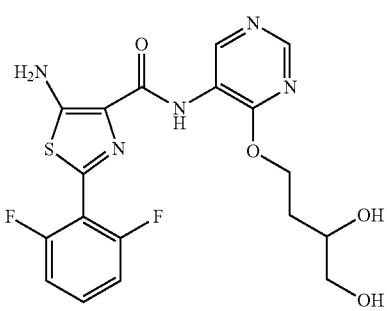

38

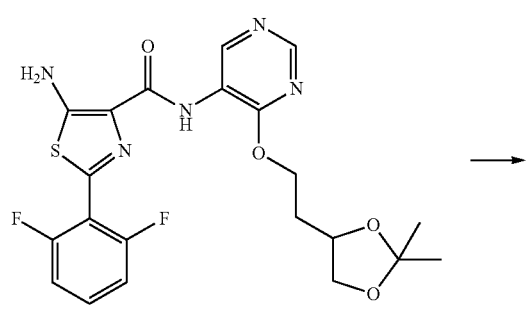

49

At room temperature (25° C.), to a solution of 5-amino-2-(2,6-difluorophenyl)-N-(4-(2-(2,2-dimethyl-1,3-dioxolan-4-yl)ethoxy)pyrimidin-5-yl)thiazole-4-carboxamide (38) (20 mg, 0.0419 mmol) in methanol (2 mL) was added concentrated HCl (0.5 mL) and the solution was stirred for 4 hours. 10% $Na_2CO_3$ solution was added to neutralize the solution to pH=7, the water (20 mL) was added and a precipitate was formed. An off white solid product 49 (11 mg, 0.0252 mmol) was obtained after filtration and air drying at 25° C.

Example 50

Synthesis of 2-(2,6-difluorophenyl)-N-(4-(3,4-dihydroxybutoxy)pyrimidin-5-yl)thiazole-4-carboxamide (50)

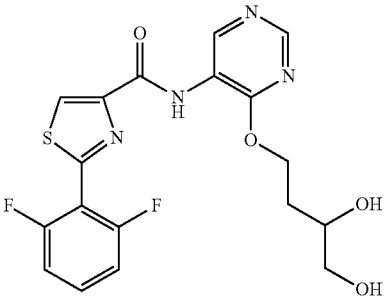 [SMILES: O=C(Nc1cncnc1OCCC(O)CO)c1csc(-c2c(F)cccc2F)n1]

Following the procedure described in Example 38 and 49, and substituting Compound 2E in Step (1) of Example 38 with 2-(2,6-difluorophenyl)thiazole-4-carboxylic acid (1E) (40 mg, 0.166 mmol), the title compound 50 (15 mg, 0.0355 mmol) was obtained.

Example 51

Synthesis of 5-amino-2-(2,6-difluorophenyl)-N-(4-(2,3-dihydroxypropoxy)pyrimidin-5-yl)thiazole-4-carboxamide (51)

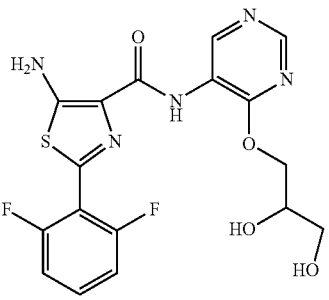 [SMILES: Nc1sc(-c2c(F)cccc2F)nc1C(=O)Nc1cncnc1OCC(O)CO]

Following the procedure described in Example 48, and substituting Compound 38 in Step (1) with 5-amino-2-(2,6-difluorophenyl)-N-(4-((2,2-dimethyl-1,3-dioxolan-4-yl)methoxy)pyrimidin-5-yl)thiazole-4-carboxamide (36) (20 mg, 0.0432 mmol), the title compound 51 (9 mg, 0.0213 mmol) was obtained.

Example 52

Synthesis of 5-amino-2-(2,6-difluorophenyl)-N-(4-(4-(methylamino)butoxy)pyrimidin-5-yl)thiazole-4-carboxamide (52)

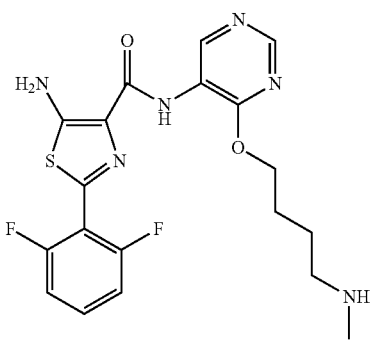 [SMILES: CNCCCCOc1ncncc1NC(=O)c1nc(-c2c(F)cccc2F)sc1N]

Following the procedure described in Example 29, and substituting Compound 29B2 in Step (1) with tert-butyl (4-hydroxybutyl)(methyl)carbamate (52B2) (50 mg, 0.246 mmol), the title compound 52 (13 mg, 0.0299 mmol) was obtained.

Example 53

Synthesis of 5-amino-2-(2,6-difluorophenyl)-N-(4-(piperidin-4-ylthio)pyrimidin-5-yl)thiazole-4-carboxamide (53)

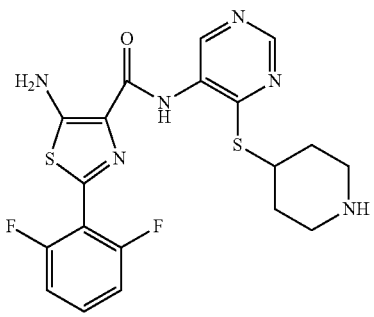 [SMILES: Nc1sc(-c2c(F)cccc2F)nc1C(=O)Nc1cncnc1SC1CCNCC1]

Following the procedure described in Example 35 and Step (3) of Example 1, and substituting Compound 35B1 in Step (1) of Example 35 with tert-butyl 4-mercaptopiperidine-1-carboxylate (53B1) (250 mg, 1.15 mmol), the title compound 53 (16 mg, 0.0356 mmol) was obtained.

Example 54

Synthesis of 2-(2,6-difluorophenyl)-N-(4-((4-hydroxy-4-methylpentyl)oxy)pyrimidin-5-yl)-5-(methylamino)thiazole-4-carboxamide (54)

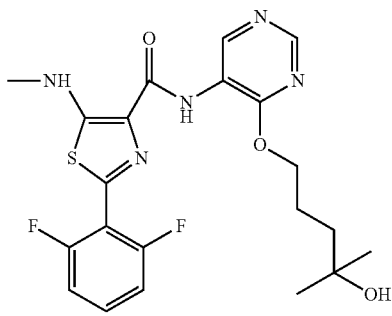 [SMILES: CNc1sc(-c2c(F)cccc2F)nc1C(=O)Nc1cncnc1OCCCC(C)(C)O]

Following the procedure described in Example 47, and substituting Compound 2E in Step (2) with 2-(2,6-difluorophenyl)-5-(methylamino)thiazole-4-carboxylic acid (54E) (40 mg, 0.148 mmol), the title compound 54 (24 mg, 0.0518 mmol) was obtained.

Example 55

Synthesis of 2-(2,6-difluorophenyl)-5-formamido-N-(4-((4-hydroxy-4-methylpentyl)oxy)pyrimidin-5-yl)thiazole-4-carboxamide (55)

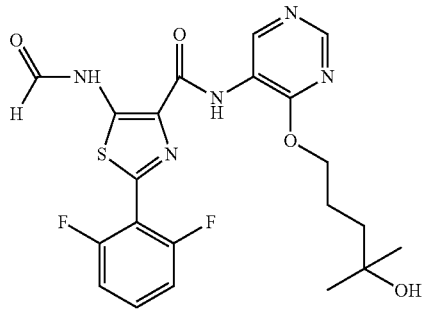 [SMILES: CC(C)(O)CCCOc1ncncc1NC(=O)c1nc(-c2c(F)cccc2F)sc1NC=O]

Following the procedure described in Example 47, and substituting Compound 2E in Step (2) with 2-(2,6-difluorophenyl)-5-formamidothiazole-4-carboxylic acid (55E) (40 mg, 0.141 mmol), the title compound 55 (24 mg, 0.0518 mmol) was obtained.

Example 56

Synthesis of 2-(2,6-difluorophenyl)-5-(methylamino)-N-(4-(piperidin-4-yloxy)pyrimidin-5-yl)thiazole-4-carboxamide (56)

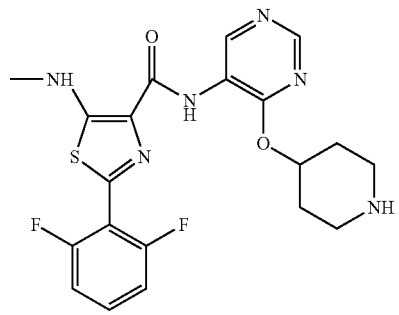 [SMILES: CNc1sc(-c2c(F)cccc2F)nc1C(=O)Nc1cncnc1OC1CCNCC1]

Following the procedure described in Example 3, and substituting Compound 1E in Step (2) with 2-(2,6-difluorophenyl)-5-(methylamino)thiazole-4-carboxylic acid (54E) (40 mg, 0.148 mmol), the title compound 56 (19 mg, 0.0425 mmol) was obtained.

Example 57

Synthesis of 2-(2,6-difluorophenyl)-N-(4-(piperidin-4-yloxy)pyrimidin-5-yl)oxazole-4-carboxamide (57)

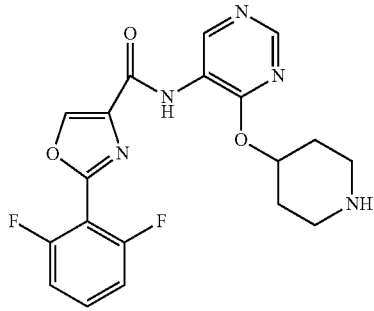 [SMILES: O=C(Nc1cncnc1OC1CCNCC1)c1coc(-c2c(F)cccc2F)n1]

Following the procedure described in Example 3, and substituting Compound 1E in Step (2) with 2-(2,6-difluorophenyl)oxazole-4-carboxylic acid (57E) (40 mg, 0.180 mmol), the title compound 57 (19 mg, 0.0473 mmol) was obtained.

Example 58

Synthesis of N-(4-(piperidin-4-yloxy)pyrimidin-5-yl)-2-(pyridin-2-yl)thiazole-4-carboxamide (58)

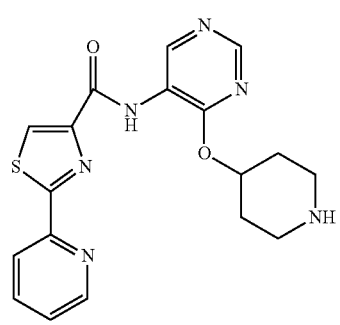 [SMILES: O=C(Nc1cncnc1OC1CCNCC1)c1csc(-c2ccccn2)n1]

Following the procedure described in Example 3, and substituting Compound 1E in Step (2) with 2-(pyridin-2-yl)thiazole-4-carboxylic acid (58E) (40 mg, 0.194 mmol), the title compound was 58 (15 mg, 0.0392 mmol) obtained.

Example 59

Synthesis of 2-(piperidin-4-yl)-N-(4-(piperidin-4-yloxy)pyrimidin-5-yl)thiazole-4-carboxamide (59)

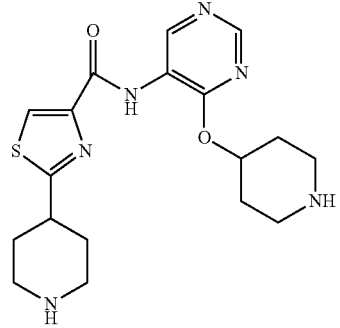 [SMILES: O=C(Nc1cncnc1OC1CCNCC1)c1csc(C2CCNCC2)n1]

Following the procedure described in Example 3, and substituting Compound 1E in Step (2) with 2-(1-(tert-butoxycarbonyl)piperidin-4-yl)thiazole-4-carboxylic acid (59E) (40 mg, 0.157 mmol), the title compound 59 (8 mg, 0.0206 mmol) was obtained.

Example 60

Synthesis of 2-morpholino-N-(4-(piperidin-4-yloxy)pyrimidin-5-yl)thiazole-4-carboxamide (60)

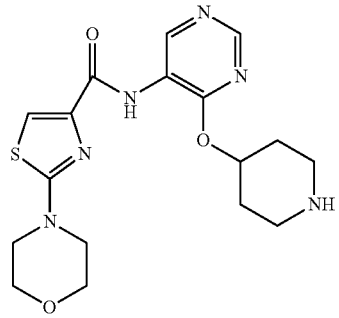 [SMILES: O=C(Nc1cncnc1OC1CCNCC1)c1csc(N2CCOCC2)n1]

Following the procedure described in Example 3, and substituting Compound 1E in Step (2) with 2-morpholinothiazole-4-carboxylic acid (60E) (40 mg, 0.187 mmol), the title compound was 60 (14 mg, 0.0358 mmol) obtained.

Example 61

Synthesis of 2-(piperidin-1-yl)-N-(4-(piperidin-4-yloxy)pyrimidin-5-yl)thiazole-4-carboxamide (61)

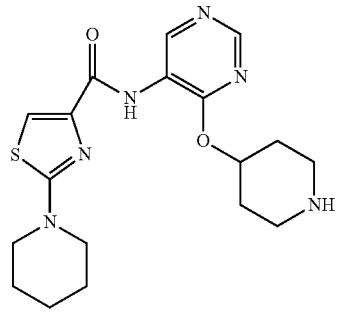 [SMILES: O=C(Nc1cncnc1OC1CCNCC1)c1csc(N2CCCCC2)n1]

Following the procedure described in Example 3, and substituting Compound 1E in Step (2) with 2-(piperidin-1-yl)thiazole-4-carboxylic acid (61E)(40 mg, 0.189 mmol), the title compound 61 (18 mg, 0.0463 mmol) was obtained.

Example 62

Synthesis of 2-acetamido-N-(4-(piperidin-4-yloxy)pyrimidin-5-yl)thiazole-4-carboxamide (62)

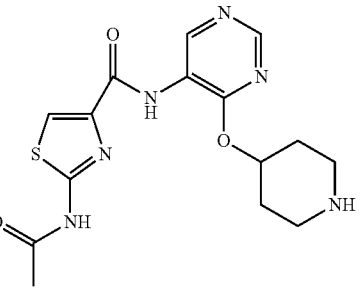

Following the procedure described in Example 3, and substituting Compound 1E in Step (2) with 2-acetamidothiazole-4-carboxylic acid (62E) (40 mg, 0.215 mmol), the title compound 62 (13 mg, 0.0358 mmol) was obtained.

Example 63

Synthesis of 5-amino-2-(2,6-difluorophenyl)-N-(4-((3-hydroxypropyl)sulfonyl)pyrimidin-5-yl)thiazole-4-carboxamide (63)

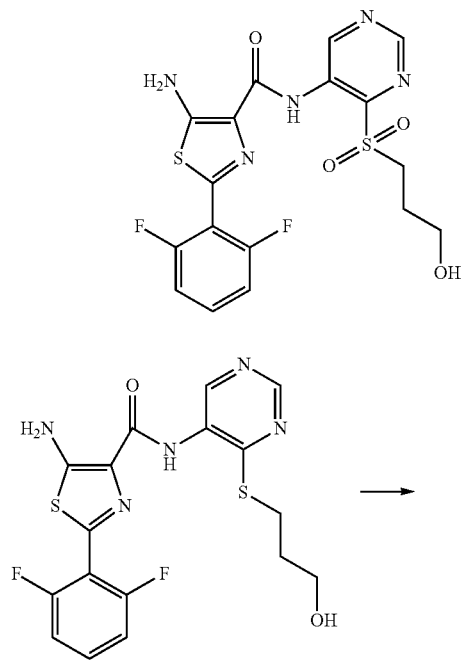

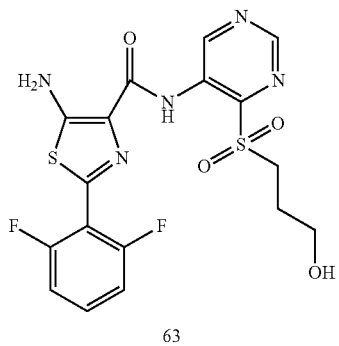

To a solution of 5-amino-2-(2,6-difluorophenyl)-N-(4-((3-hydroxypropyl)thio)pyrimidin-5-yl)thiazole-4-carboxamide (35) (60 mg, 0.142 mmol) in THF (2 mL) at room temperature (25° C.) was added imidazole (20 mg, 0.284 mmol) and trimethylsilyl chloride (17 mg, 0.156 mmol) and stirred for 30 min, then water (20 mL) was added. A solid was obtained after filtration and then directly dissolved in $CH_2CH_2$ (1 mL). Then m-CPBA (54 mg, 0.312 mmol) was added. The solution was stirred over night. TLC showed the reaction had completed. The solution was washed with 1 mL each of 10% $Na_2SO_3$ solution, 1N HCl, saturated solution, and dried over anhydrous $Na_2SO_4$. The solution was the concentration in vacuo at room temperature (25° C.). The residue was then purified with flash column (eluent: 10-40% ethyl acetate/petroleum ether) to obtained the title compound 63 (22 mg, 0.0482 mmol).

Analytical data of the compound described in the examples of the present invention:

| | Structure | $^1$HNMR | MS |
|---|---|---|---|
| 1 | 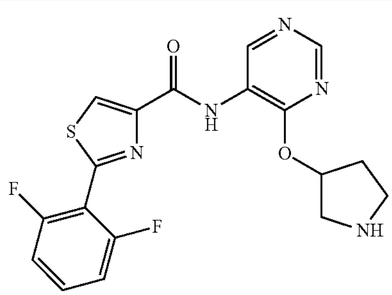 [SMILES: O=C(Nc1cncnc1OC1CCNC1)c1csc(-c2c(F)cccc2F)n1] | $^1$H NMR (400 MHz, $CDCl_3$) δ 2.10-2.22 (m, 1H), 2.28-2.31 (m, 1H), 3.00-3.02 (m, 1H), 3.28-3.31 (m, 1H), 3.30-3.34 (m, 2H), 5.71 (m, 1H), 7.11-7.15 (m, 2H), 7.45-7.49 (m, 1H), 8.40 (s, 1H), 8.56 (s, 1H), 9.63 (s, 1H), 9.75 (s, 1H), | M + 1: 404 |
| 2 | 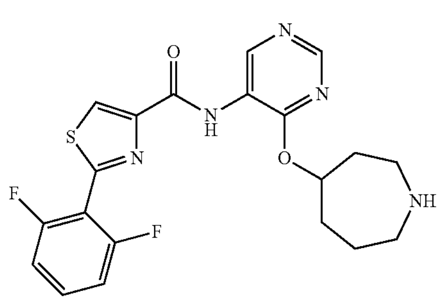 [SMILES: O=C(Nc1cncnc1OC1CCCNCC1)c1csc(-c2c(F)cccc2F)n1] | $^1$H NMR (400 MHz, $CDCl_3$) δ 1.68 (m, 1H), 2.06-2.08 (m, 2H), 2.07-2.15 (m, 3H), 2.90-3.00 (m, 4H), 5.53 (m, 1H), 7.07-7.09 (m, 2H), 7.42 (m, 1H), 8.37 (s, 1H), 8.51 (s, 1H), 9.61 (s, 1H), 9.75 (s, 1H), | M + 1: 432 |

-continued
| | Structure | ¹HNMR | MS |
|---|---|---|---|
| 3 | 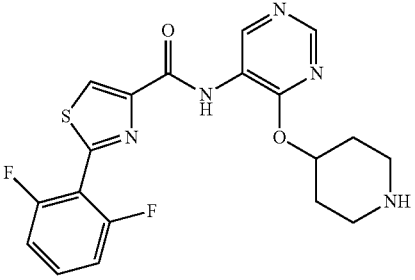 [SMILES: O=C(Nc1cncnc1OC1CCNCC1)c1csc(-c2c(F)cccc2F)n1] | ¹H NMR (400 MHz, CDCl₃) δ 1.86 (d, J = 8.84, 2H), 2.14 (t, J = 10.23, 2H), 2.85 (t, J = 10.23, 2H), 3.22 (t, J = 10.23, 2H), 5.22-5.52 (m, 1H), 7.14 (bs, 2H), 7.37-7.60 (m, 1H), 8.43 (s, 1H), 8.51-8.61 (m, 1H), 9.52-9.70 (m, 1H), 9.72-9.95 (m, 1H) | M + 1: 418 |
| 4 | 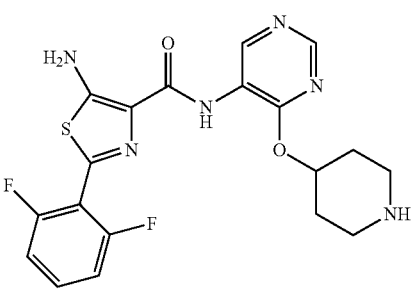 [SMILES: Nc1sc(-c2c(F)cccc2F)nc1C(=O)Nc1cncnc1OC1CCNCC1] | ¹H NMR (400 MHz, CD₃OD) δ 2.27-2.35 (m, 4H), 3.35-3.37 (m, 2H), 3.44-3.51 (m, 2H), 5.57-5.60 (m, 1H), 7.16-7.21 (m, 2H), 7.46-7.50 (m, 1H), 8.52 (s, 1H), 9.53 (s, 1H) | M + 1: 433 |
| 5 | 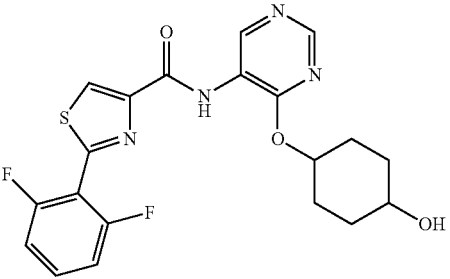 [SMILES: O=C(Nc1cncnc1OC1CCC(O)CC1)c1csc(-c2c(F)cccc2F)n1] | ¹H NMR (400 MHz, CDCl₃) δ 1.44-1.54 (m, 2H), 1.69-1.86 (m, 2H), 1.99-2.11 (m, 2H), 2.15-2.30 (m, 2H), 3.86-3.94 (m, 1H), 4.50-4.67 (m, 1H), 5.29 (s, 1H), 7.06-7.14 (m, 2H), 7.37-7.50 (m, 1H), 8.38 (s, 1H), 8.46 (s, 1H), 9.66 (s, 1H), 9.81 (bs, 1H) | M + 1: 433 |
| 6 | 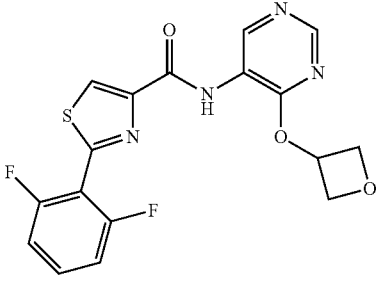 [SMILES: O=C(Nc1cncnc1OC1COC1)c1csc(-c2c(F)cccc2F)n1] | ¹H NMR (400 MHz, CDCl₃) δ 4.76-4.90 (m, 2H), 5.02-5.12 (m, 2H), 5.76 (quin, J = 5.56 Hz, 1H), 7.02-7.13 (m, 2H), 7.35-7.51 (m, 1H), 8.39 (s, 1H), 8.45 (s, 1H), 9.60 (s, 1H), 9.80 (bs, 1H) | M + 1: 391 |
| 7 | 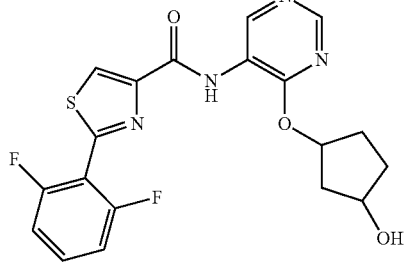 | ¹H NMR (400 MHz, DMSO-d6) δ 1.22-1.23 (m, 1H), 1.55-1.62 (m, 1H), 1.77-1.83 (m, 2H), 1.92-2.08 (m, 2H), 2.19-2.29 (m, 1H), 4.34 (bs, 1H), 5.62 (bs, 1H), 7.39 (t, J = 8.72 Hz, 2H), 7.65-7.72 (m, 1H), 8.57 (s, 1H), 8.79 (s, 1H), 9.31 (s, 1H), 9.71 (s, 1H), | M + 1: 419 |

-continued
| | Structure | ¹HNMR | MS |
|---|---|---|---|
| 8 | 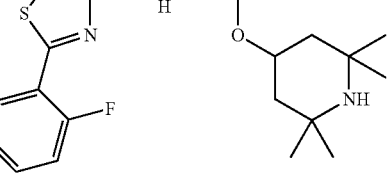 | ¹H NMR (400 MHz, DMSO-d6) δ 1.45 (s, 6H), 1.49 (s, 6H), 1.80 (s, 2H), 2.32-2.36 (m, 2H), 5.58-5.64 (m, 1H), 7.38 (t, J = 8.72 Hz, 2H), 7.67-7.74 (m, 1H), 8.63 (s, 1H), 8.81 (s, 1H), 9.28 (s, 1H), 9.81 (s, 1H) | M + 1: 474 |
| 9 | 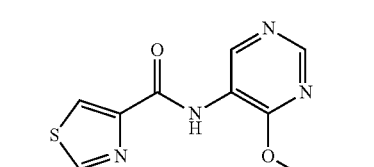 | ¹H NMR (400 MHz, CD₃OD) δ 1.37 (s, 3H), 4.39-3.40 (m, 2H), 4.53-4.54 (m, 2H), 4.56 (s, 2H), 7.05-7.15 (m, 2H), 7.38-7.49 (m, 1H), 8.52 (s, 1H), 9.63 (bs, 1H), 9.69 (bs, 1H) | M + 1: 418 |
| 10 | 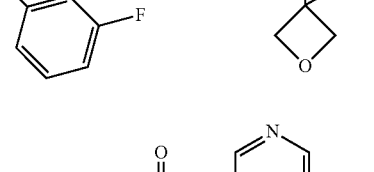 | ¹H NMR (400 MHz, DMSO-d6) δ 2.99-3.13 (m, 1H), 3.35 (d, J = 7.78 Hz, 2H), 3.59 (t, J = 7.53 Hz, 2H), 4.39 (d, J = 6.27 Hz, 2H), 7.05-7.15 (m, 2H), 7.38-7.49 (m, 1H), 8.38 (s, 1H), 8.52 (s, 1H), 9.63 (bs, 1H), 9.69 (bs, 1H) | M + 1: 404 |
| 11 | 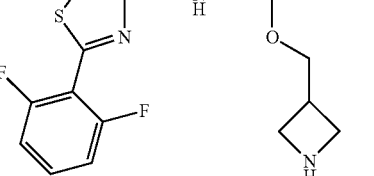 | ¹H NMR (400 MHz, DMSO-d6) δ 2.14 (t, J = 10.23, 2H),, 2.85 (t, J = 10.23, 2H), 3.22 (t, J = 10.23, 4H), 5.22-5.52 (m, 1H), 7.37-7.40 (m, 2H), 7.70 (s, 1H), 8.00-8.01 (m, 1H), 8.26-8.29 (m, 2H), 8.45 (m, 1H), 8.60 (s, 1H), 9.39 (s, 1H), 10.34 (s, 1H) | M + 1: 412 |
| 12 | 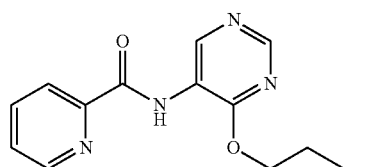 | ¹H NMR (400 MHz, CDCl₃) δ 1.79 (d, J = 6.32 Hz, 1H), 2.15 (dd, J = 12.63, 5.05 Hz, 1H), 2.83 (t, J = 6.69 Hz, 1H) 3.64-3.82 (m, 2H), 3.85-4.04 (m, 2H), 4.39 (d, J = 8.08 Hz, 1H), 4.48 (d, J = 3.79 Hz, 1H), 7.05-7.15 (m, 2H), 7.38-7.49 (m, 1H), 8.38 (s, 1H), 8.52 (s, 1H), 9.63 (bs, 1H), 9.69 (bs, 1H) | M + 1: 419 |

-continued
| | Structure | ¹HNMR | MS |
|---|---|---|---|
| 13 | 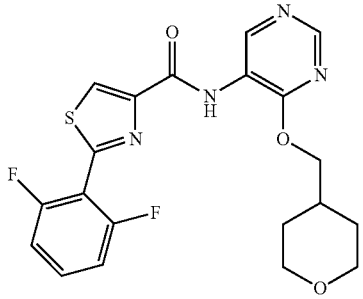 [SMILES: O=C(Nc1cncnc1OCC1CCOCC1)c1csc(-c2c(F)cccc2F)n1] | ¹H NMR (400 MHz, CDCl₃) δ 1.43-1.54 (m, 4H), 1.79-1.92 (m, 1H), 3.36-3.57 (m, 2H), 3.93-4.09 (m, 2H), 4.33 (d, J = 6.82 Hz, 2H), 7.01-7.17 (m, 2H), 7.41-7.58 (m, 1H), 8.41 (s, 1H), 8.54 (s, 1H), 9.67 (s, 1H), 9.79 (bs, 1H) | M + 1: 433 |
| 14 | 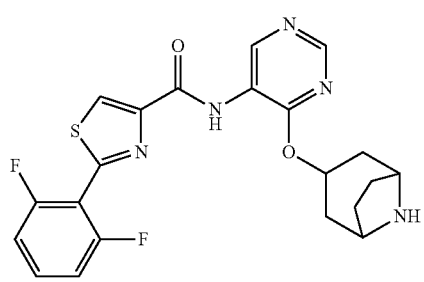 [SMILES: O=C(Nc1cncnc1OC1CC2CCC(C1)N2)c1csc(-c2c(F)cccc2F)n1] | ¹H NMR (400 MHz, CDCl₃) δ 1.20-1.32 (m, 1H), 1.78-1.98 (m, 6H), 2.17-2.35 (m, 2H), 3.67 (bs, 2H), 5.51 (s, 1H), 7.05-7.17 (m, 2H), 7.36-7.52 (m, 1H), 8.35 (s, 1H), 8.48 (s, 1H), 9.59 (s, 1, H) 9.65 (s, 1H) | M + 1: 444 |
| 15 | 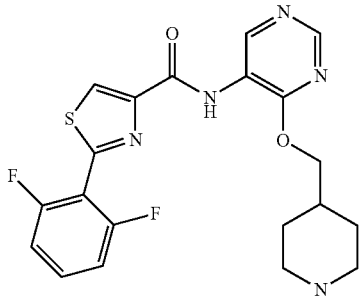 | ¹H NMR (MHz, CD₃OD) δ 1.25-1.35 (m, 2H), 1.99-2.01 (m, 2H), 2.02-2.08 (m, 1H), 2.60-2.67 (m, 2H), 3.07-3.09 (m, 2H), 4.30-4.31 (m, 2H), 7.18-7.23 (m, 2H), 7.54-7.61 (m, 1H), 8.45 (s, 1H), 8.55 (s, 1H), 9.44 (s, 1H) | M + 1: 432 |
| 16 | 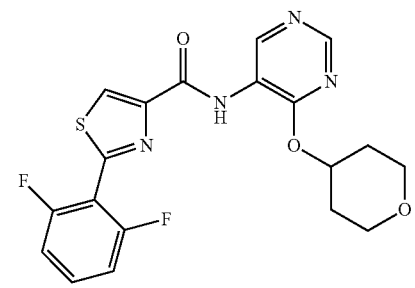 [SMILES: O=C(Nc1cncnc1OC1CCOCC1)c1csc(-c2c(F)cccc2F)n1] | ¹H NMR (400 MHz, DMSO-d6) δ 1.60-1.80 (m, 2H), 1.95-2.15 (m, 2H), 3.49-3.62 (m, 2H), 3.78-3.98 (m, 2H), 4.85-5.03 (m, 1H), 7.24-7.28 (m, 2H), 7.58-7.65 (m, 1H), 8.51 (s, 1H), 8.61 (s, 1H), 9.48 (s, 1H), 9.88 (s, 1H) | M + 1: 419 |
| 17 | 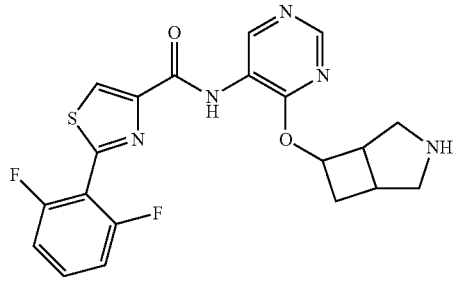 [SMILES: O=C(Nc1cncnc1OC1CC2CNCC21)c1csc(-c2c(F)cccc2F)n1] | ¹H NMR (400 MHz, DMSO-d6) δ 1.73-1.79 (m, 1H), 2.45-2.48 (m, 2H), 2.55-2.66 (m, 3H), 2.71-2.73 (m, 1H), 3.12-3.14 (m, 1H), 3.17-3.19 (m, 1H), 5.21-5.27 (m, 1H), 7.37-7.42 (m, 2H), 7.64-8.73 (m, 1H), 8.54 (s, 1H), 8.82 (s, 1H), 9.25 (s, 1H), 9.80 (s, 1H) | M + 1: 430 |

| | Structure | ¹HNMR | MS |
|---|---|---|---|
| 18 | 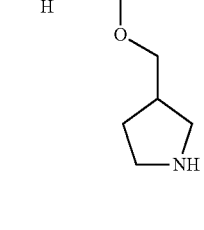 | ¹H NMR (400 MHz, CD₃OD) δ 1.67-1.74 (m, 1H), 2.08-2.17 (m, 1H), 2.71-2.78 (m, 1H), 2.83-2.97 (m, 2H), 3.02-3.08 (m, 1H), 3.16-3.21 (m, 1H), 4.42-4.47 (m, 1H), 4.54-4.58 (m, 1H), 7.24-7.28 (m, 2H), 7.58-7.65 (s, 1H), 8.51 (s, 1H), 8.61 (s, 1H), 9.48 (s, 1H) | M + 1: 418 |
| 19 | 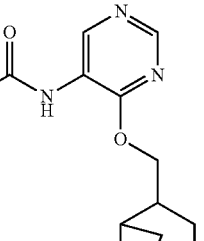 | ¹H NMR (400 MHz, CD₃OD) δ 1.51 (m, 1H), 1.69 (m, 1H), 1.82 (m, 1H), 2.09 (m, 1H), 2.39-2.43, (m, 1H), 2.56-2.60 (m, 1H), 2.85-2.89 (m, 4H), 3.14-3.21 (m, 2H), 4.24-4.26 (m, 2H), 7.39 (t, J = 8.8 Hz, 2H), 7.72-7.65 (m, 1H), 8.81 (s, 1H), 9.31 (s, 1H), 9.77 (s, 1H), | M + 1: 458 |
| 20 | 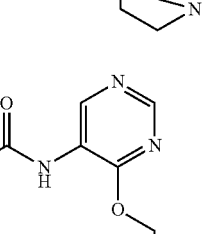 | ¹H NMR (400 MHz, CD₃OD) δ 1.37 (s, 3H), 4.39 (d, J = 7.8 Hz, 2H), 4.53 (d, J = 7.6 Hz, 2H), 4.56 (s, 2H), 7.10-7.24 (m, 5H), 7.33-7.38 (m, 1H), 7.49-7.56 (m, 2H), 8.17-8.19 (d, J = 5.6 Hz, 1H), 9.51 (s., 1H), 10.57 (s, 1H) | M + 1: 428 |
| 21 | 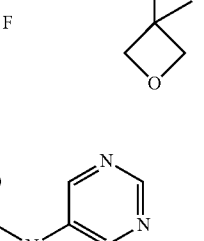 | ¹H NMR (400 MHz, DMSO-d6) δ 4.12-4.19 (m, 2H), 4.43-4.51 (m, 2H), 5.53-5.59 (m, 1H), 7.41 (t, J = 8.8 Hz, 2H), 7.68-7.75- (m, 1H), 8.62 (s, 1H), 8.84 (s, 1H), 9.29 (s, 1H), 9.84 (s, 1H) | M + 1: 390 |
| 22 | 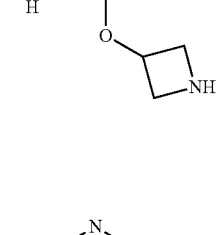 | ¹H NMR (400 MHz, DMSO-d6) δ 1.39-1.50 (m, 1H), 1.66-1.81 (m, 2H), 2.03-2.08 (m, 1H), 2.21-2.28 (m, 1H), 2.54-2.60 (m, 1H), 2.70-2.76 (m, 2H), 3.06-3.10 (m, 1H), 5.07-5.13 (m, 1H), 7.39 (t, J = 8.8 Hz, 2H), 7.65-7.72 (m, 1H), 8.56 (s, 1H), 8.81 (s, 1H), 9.31 (s, 1H), 9.77 (s, 1H), | M + 1: 418 |

-continued

| | Structure | ¹HNMR | MS |
|---|---|---|---|
| 23 | 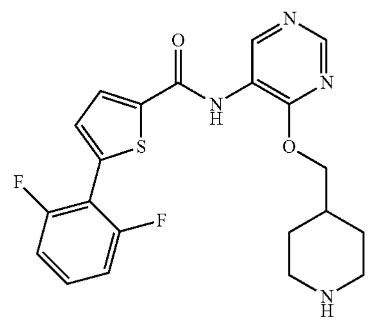 [SMILES: O=C(Nc1cncnc1OCC1CCNCC1)c1ccc(-c2c(F)cccc2F)s1] | ¹H NMR (400 MHz, CD₃OD) δ 1.53-1.63 (m, 2H), 2.09-2.12 (m, 2H), 2.20-2.26 (m, 1H), 3.00-3.06 (m, 2H), 3.42-3.45 (m, 2H), 4.47-4.49 (d, 2H), 7.13-7.16 (m, 2H), 7.43-7.47 (m, 1H), 7.61-7.64 (m, 1H), 7.91-7.92 (m, 1H), 8.63 (s, 1H), 8.87 (s, 1H), | M + 1: 431 |
| 24 | 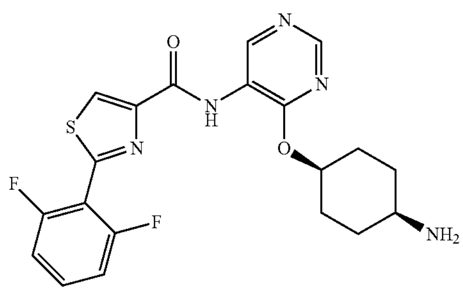 [SMILES: N[C@H]1CC[C@@H](Oc2ncncc2NC(=O)c2csc(-c3c(F)cccc3F)n2)CC1] | ¹H NMR (400 MHz, CDCl₃) δ 1.58-1.65 (m, 4H), 1.65-1.87 (m, 4H), 2.06-2.30 (m, 2H), 2.71-2.85 (m, 1H), 5.40-5.53 (m, 1H), 7.00-7.18 (m, 2H), 7.37-7.52 (m, 1H), 8.44 (s, 1H), 8.53 (s, 1H), 9.66 (s, 1H), 9.73 (bs, 1 H) | M + 1: 432 |
| 25 | 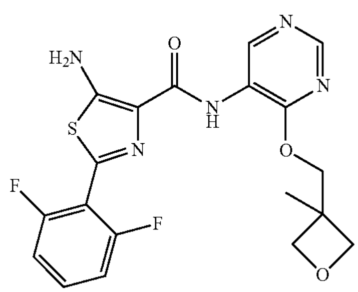 | ¹H NMR (400 MHz, CD₃OD) δ 1.37 (s, 3H), 4.39 (d, J = 5.6 Hz, 2H), 4.53 (d, J = 5.6 Hz, 2H), 4.56 (s, 2H), 7.01-7.05 (m, 2H), 7.32-7.39 (m, 1H), 8.35 (s, 1H), 9.41 (s, 1H), | M + 1: 419 |
| 26 | 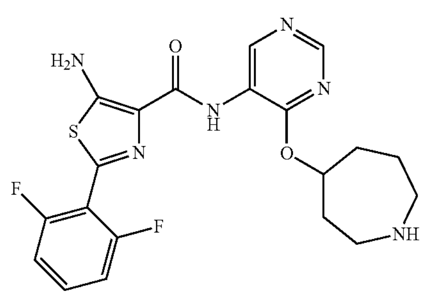 [SMILES: Nc1sc(-c2c(F)cccc2F)nc1C(=O)Nc1cncnc1OC1CCCNCC1] | ¹H NMR (400 MHz, CD₃OD) δ 1.55-1.65 (m, 1H), 1.83-1.96 (m, 1H), 2.03-2.13 (m, 4H), 2.76-2.79 (m, 1H), 2.81-2.85 (m, 2H), 2.90-2.96 (m, 1H), 5.44-5.50 (m, 1H), 7.02-7.06 (m, 2H), 7.31-7.38 (m, 1H), 8.31 (s, 1H), 9.36 (s, 1H), | M + 1: 447 |
| 27 | 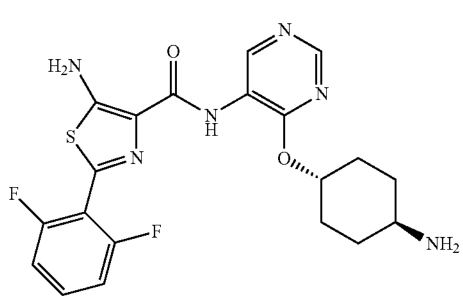 [SMILES: Nc1sc(-c2c(F)cccc2F)nc1C(=O)Nc1cncnc1O[C@H]1CC[C@H](N)CC1] | ¹H NMR (400 MHz, CD₃OD) δ 1.20-1.51 (m, 2H), 1.64-1.69 (m, 2H), 1.98-2.02 (m, 2H), 2.20-2.23 (m, 2H), 2.84-2.90 (m, 1H), 4.35-4.41 (m, 1H), 7.02-7.06 (m, 2H), 7.31 7.38 (m, 1H), 8.31 (s, 1H), 9.36 (s, 1H) | M + 1: 447 |

| | Structure | ¹HNMR | MS |
|---|---|---|---|
| 28 | 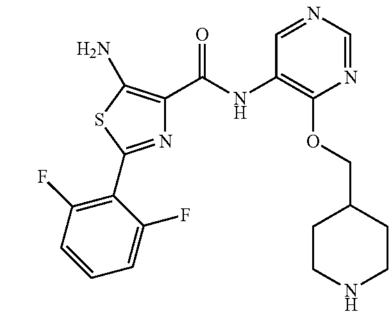 [SMILES: Nc1sc(-c2c(F)cccc2F)nc1C(=O)Nc1cncnc1OCC1CCNCC1] | ¹H NMR (400 MHz, CD$_3$OD) δ 1.26-1.29 (m, 2H), 1.91-1.94 (m, 2H), 2.04-2.12 (m, 1H), 2.66-2.69 (m, 2H), 3.10-3.13 (m, 2H), 3.90-3.98 (m, 2H), 6.99-7.02 (m, 2H), 7.31-7.41 (m, 1H), 8.33 (s, 1H), 9.40 (s, 1H) | M + 1: 447 |
| 29 | 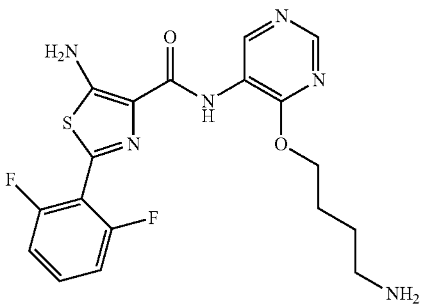 [SMILES: NCCCCOc1ncncc1NC(=O)c1nc(-c2c(F)cccc2F)sc1N] | ¹H NMR (400 MHz, CD$_3$OD) δ 1.48-1.61 (m, 2H), 1.75-1.82 (m, 2H), 2.79-2.82 (m, 2H), 4.26 (t, J = 5.96 Hz, 2H), 7.00-7.04 (m, 2H), 7.29-7.41 (m, 1H), 8.36 (s, 1H), 9.42 (s, 1H) | M + 1: 421 |
| 30 | 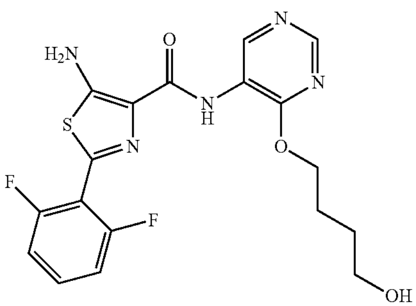 [SMILES: Nc1sc(-c2c(F)cccc2F)nc1C(=O)Nc1cncnc1OCCCCO] | ¹H NMR (400 MHz, CD$_3$OD) δ 1.44-1.50 (m, 2H), 1.70-1.78 (m, 2H), 3.32-3.45 (m, 2H), 4.22 (t, J = 5.96 Hz, 2H), 7.01-7.04 (m, 2H), 7.31-7.42 (m, 1H), 8.35 (s, 1H), 9.39 (s, 1H) | M: 421 |
| 31 | 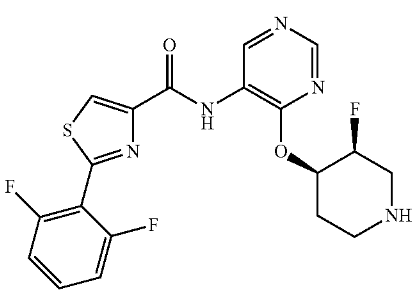 [SMILES: O=C(Nc1cncnc1O[C@@H]1CCNC[C@@H]1F)c1csc(-c2c(F)cccc2F)n1] | ¹H NMR (400 MHz, CD$_3$OD) δ 1.42-1.58 (m, 1H), 2.01-2.15 (m, 1H), 2.35 (bs, 1H), 2.54-2.70 (m, 2H), 2.82 (d, J = 9.80 Hz, 1H), 3.22 (ddd, J = 5.00, 8.04, 12.40 Hz, 1H), 4.45-4.70 (m, 1H), 7.00-7.18 (m, 2H), 7.37-7.52 (m, 1H), 8.53 (s, 1H), 9.66 (s, 1H), 9.73 (bs, 1H) | M + 1: 436 |
| 32 | 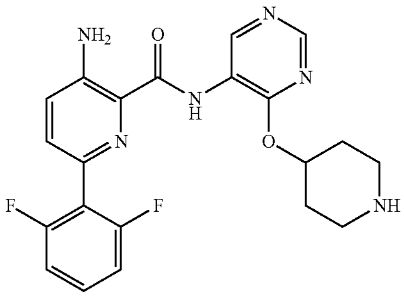 [SMILES: Nc1ccc(-c2c(F)cccc2F)nc1C(=O)Nc1cncnc1OC1CCNCC1] | ¹H NMR (400 MHz, CD$_3$OD) δ 2.20-2.33 (m, 4H), 3.34-3.37 (m, 2H), 3.42-3.49 (m, 2H), 5.57-5.61 (m, 1H), 7.09-7.24 (m, 3H), 7.33-7.38 (m, 1H), 8.17-8.19 (d, J = 5.6 Hz, 1H), 9.51 (s., 1H), 10.57 (s, 1H), | M + 1: 427 |

-continued

| | Structure | ¹HNMR | MS |
|---|---|---|---|
| 33 | 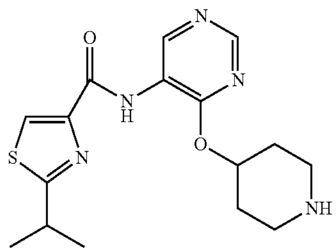 [SMILES: CC(C)c1nc(C(=O)Nc2cncnc2OC2CCNCC2)cs1] | ¹H NMR (400 MHz, CD₃OD) δ 1.45-1.46 (d, J = 6.80 Hz, 6H), 2.22-2.31 (m, 5H), 3.34-3.35 (m, 2H), 3.46-3.49 (m, 2H), 5.60-5.61 (m, 1H), 8.49 (s, 1H), 9.47 (s, 1H), 9.65 (s, 1H) | M + 1: 348 |
| 34 | 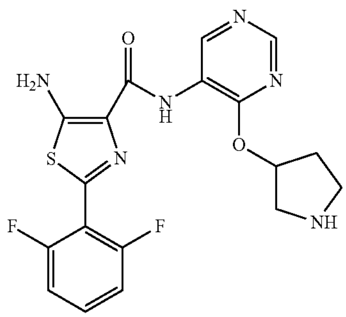 [SMILES: Nc1sc(-c2c(F)cccc2F)nc1C(=O)Nc1cncnc1OC1CCNC1] | ¹H NMR (400 MHz, CD₃OD) δ 2.09-20 (m, 1H), 2.30-2.32 (m, 1H), 2.99-3.02 (m, 1H), 3.30-3.32 (m, 1H), 3.32-3.34 (m, 2H), 5.69-5.71 (m, 1H), 7.13-7.19 (m, 2H), 7.39-7.50 (m, 1H), 8.52 (s, 1H), 9.53 (s, 1H) | M + 1: 419 |
| 35 | 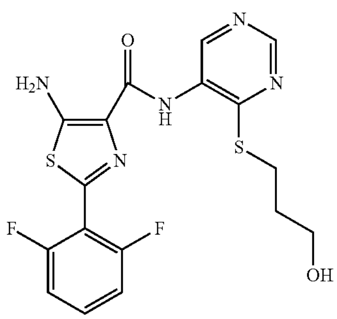 [SMILES: Nc1sc(-c2c(F)cccc2F)nc1C(=O)Nc1cncnc1SCCCO] | ¹H NMR (400 MHz, CD₃OD) δ 1.65-1.81 (m, 2H), 3.01 (t, J = 6.92 Hz, 2H), 3.51 (t, J = 6.00 Hz, 2H), 6.95-7.00 (m, 2H), 7.29-7.38 (m, 1H), 8.29 (s, 1H), 9.37 (s, 1H) | M: 423 |
| 36 | 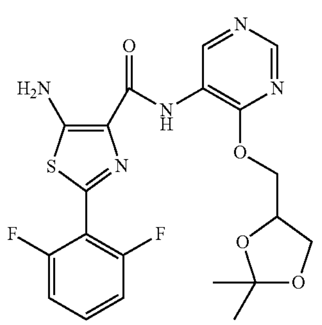 [SMILES: CC1(C)OCC(COc2ncncc2NC(=O)c2nc(-c3c(F)cccc3F)sc2N)O1] | ¹H NMR (400 MHz, CD₃OD) δ 1.40 (s, 6H), 4.00 (t, J = 4.68 Hz, 1H), 4.05 (t, J = 4.20 Hz, 1H), 4.19-4.24 (m, 2H), 4.50-4.65 (m, 1H), 7.18-7.21 (m, 2H), 7.41-7.48 (m, 1H), 8.50 (s, 1H), 9.55 (s, 1H) | M: 463 |
| 37 | 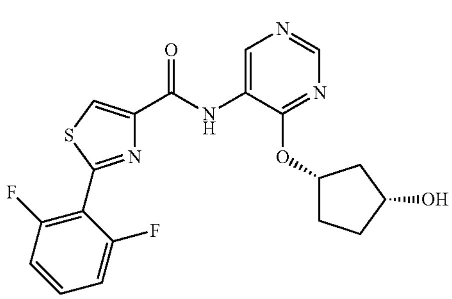 [SMILES: O=C(Nc1cncnc1O[C@H]1CC[C@@H](O)C1)c1csc(-c2c(F)cccc2F)n1] | ¹H NMR (400 MHz, CD₃OD) δ 1.68-1.79 (m, 1H), 1.98-2.09 (m, 1H), 2.12-2.24 (m, 2H), 2.25-2.43 (m, 2H), 4.55-4.64 (m, 1H), 4.98-5.07 (m, 1H), 7.00-7.20 (m, 2H), 7.41-7.50 (m, 1H), 8.55 (s, 1H), 9.66 (s, 1H), 9.73 (s, 1H) | M: 418 |

-continued

| | Structure | ¹HNMR | MS |
|---|---|---|---|
| 38 | 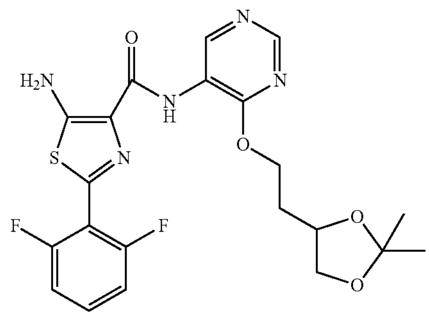 [SMILES: CC1(C)OCC(CCOc2ncncc2NC(=O)c2nc(-c3c(F)cccc3F)sc2N)O1] | ¹H NMR (400 MHz, CD₃OD) δ 1.27 (s, 6H), 2.05-2.19 (m, 2H), 4.00-4.13 (m, 2H), 4.19-4.31 (m, 1H), 4.32-4.42 (m, 2H), 7.14-7.19 (m, 2H), 7.48-7.50 (m, 1H), 8.50 (s, 1H), 9.49 (s, 1H) | M: 477 |
| 39 | 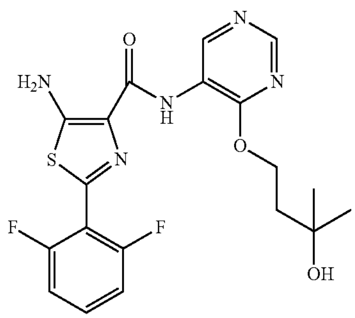 [SMILES: CC(C)(O)CCOc1ncncc1NC(=O)c1nc(-c2c(F)cccc2F)sc1N] | ¹H NMR (400 MHz, CD₃OD) δ 1.09 (s, 6H), 1.88-1.96 (m, 2H), 4.30 (t, J = 6.80 Hz, 2H), 7.18-7.21 (m, 2H), 7.51-7.53 (m, 1H), 8.53 (s, 1H), 9.57 (s, 1H) | M: 435 |
| 40 | 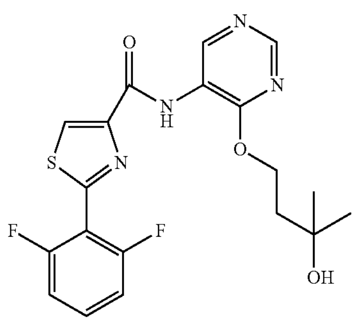 [SMILES: CC(C)(O)CCOc1ncncc1NC(=O)c1csc(-c2c(F)cccc2F)n1] | ¹H NMR (400 MHz, CD₃OD) δ 1.10 (s, 6H), 1.89-2.01 (m, 2H), 4.29 (t, J = 6.80 Hz, 2H), 7.15-7.18 (m, 2H), 7.44-7.52 (m, 1H), 8.50 (s, 1H), 9.62 (s, 1H), 9.79 (s, 1H) | M: 420 |
| 41 | 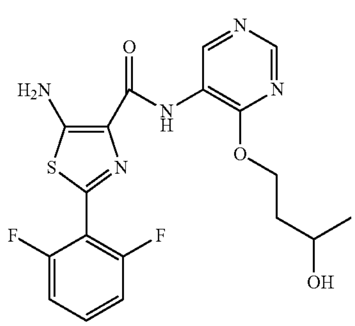 [SMILES: CC(O)CCOc1ncncc1NC(=O)c1nc(-c2c(F)cccc2F)sc1N] | ¹H NMR (400 MHz, CD₃OD) δ 1.07 (s, 3H), 1.70-1.87 (m, 2H), 3.41-3.53 (m, 1H), 4.20-4.26 (m, 2H), 7.12-7.21 (m, 2H), 7.38-7.44 (m, 1H), 8.45 (s, 1H), 9.48 (s, 1H) | M: 421 |
| 42 | 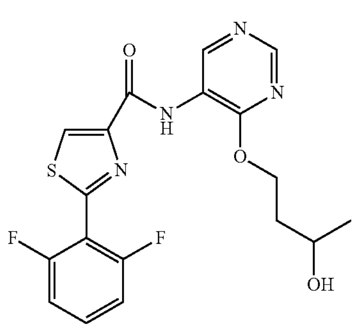 [SMILES: CC(O)CCOc1ncncc1NC(=O)c1csc(-c2c(F)cccc2F)n1] | ¹H NMR (400 MHz, CD₃OD) δ 1.02 (s, 3H), 1.77-1.87 (m, 2H), 3.52-3.56 (m, 1H), 4.12-4.20 (m, 2H), 7.04-7.20 (m, 2H), 7.37-7.52 (m, 1H), 8.57 (s, 1H), 9.71 (s, 1H), 9.80 (s, 1 H) | M: 406 |

-continued
| | Structure | ¹HNMR | MS |
|---|---|---|---|
| 43 | 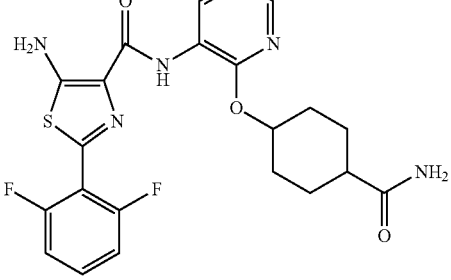 | ¹H NMR (400 MHz, CD₃OD) δ 1.28-1.60 (m, 4H), 1.82-1.92 (m, 2H), 2.08-2.27 (m, 3H), 3.46 (m, 1H), 7.16-7.19 (m, 2H), 7.41-7.48 (m, 1H), 8.39 (s, 1H), 9.47 (s, 1H) | M: 474 |
| 44 | 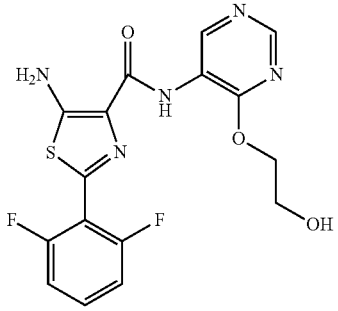 [SMILES: Nc1sc(-c2c(F)cccc2F)nc1C(=O)Nc1cncnc1OCCO] | ¹H NMR (400 MHz, CD₃OD) δ 3.81-3.87 (m, 2H), 4.24 (t, J = 4.64 Hz, 2H), 7.15-7.21 (m, 2H), 7.42-7.50 (m, 1H), 8.50 (s, 1H), 9.50 (s, 1H) | M: 393 |
| 45 | 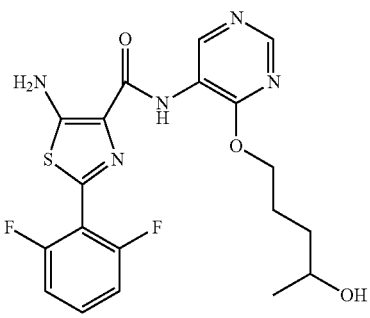 [SMILES: CC(O)CCCOc1ncncc1NC(=O)c1nc(-c2c(F)cccc2F)sc1N] | ¹H NMR (400 MHz, CD₃OD) δ 1.11 (s, 3H), 1.37-1.42 (m, 2H), 1.80-1.84 (m, 2H), 3.40-3.46 (m, 1H), 4.30 (t, J = 6.84 Hz, 2H), 7.07-7.17 (m, 2H), 7.39-7.46 (m, 1H), 8.39 (s, 1H), 9.46 (s, 1H) | M: 435 |
| 46 | 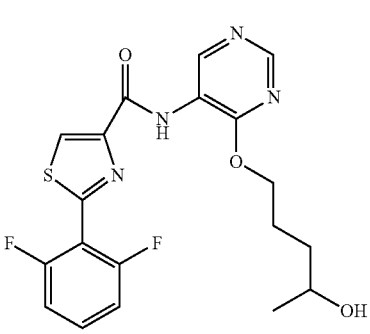 [SMILES: CC(O)CCCOc1ncncc1NC(=O)c1csc(-c2c(F)cccc2F)n1] | ¹H NMR (400 MHz, CD₃OD) δ 1.07 (s, 3H), 1.40-1.45 (m, 2H), 1.77-1.81 (m, 2H), 3.36-3.42 (m, 1H), 4.29 (t, J = 6.80 Hz, 2H), 7.05-7.14 (m, 2H), 7.44-7.52 (m, 1H), 8.55 (s, 1H), 9.60 (s, 1H), 9.69 (s, 1H) | M: 420 |
| 47 | 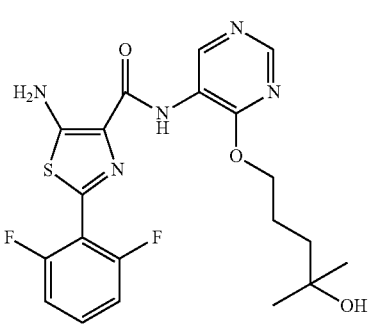 [SMILES: CC(C)(O)CCCOc1ncncc1NC(=O)c1nc(-c2c(F)cccc2F)sc1N] | ¹H NMR (400 MHz, CD₃OD) δ 1.11 (s, 6H), 1.42-1.48 (m, 2H), 1.72-1.80 (m, 2H), 4.21 (t, J = 6.84 Hz, 2H), 7.16-7.21 (m, 2H), 7.46-7.50 (m, 1H), 8.52 (s, 1H), 9.53 (s, 1H) | M: 449 |

-continued

| | Structure | ¹HNMR | MS |
|---|---|---|---|
| 48 | 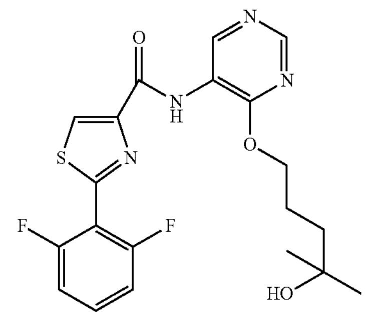 [SMILES: CC(C)(O)CCCOc1ncncc1NC(=O)c1csc(-c2c(F)cccc2F)n1] | ¹H NMR (400 MHz, CD₃OD) δ 1.09 (s, 6H), 1.36-1.44 (m, 2H), 1.68-1.80 (m, 2H), 4.18 (t, J = 6.80 Hz, 2H), 7.01-7.22 (m, 2H), 7.40-7.50 (m, 1H), 8.52 (s, 1H), 9.66 (s, 1H), 9.72 (bs, 1H) | M: 434 |
| 49 | 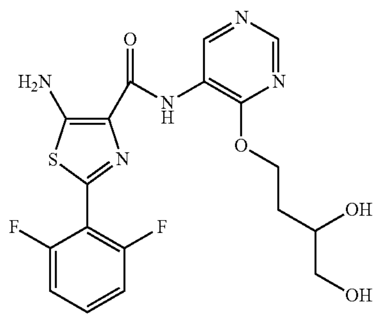 [SMILES: Nc1sc(-c2c(F)cccc2F)nc1C(=O)Nc1cncnc1OCCC(O)CO] | ¹H NMR (400 MHz, CD₃OD) δ 1.79-1.96 (m, 2H), 3.20 (bs, 2H), 3.68-3.70 (m, 1H), 4.16-4.33 (m, 2H), 7.19-7.23 (m, 2H), 7.51-7.53 (m, 1H), 8.50 (s, 1H), 9.50 (s, 1H) | M: 437 |
| 50 | 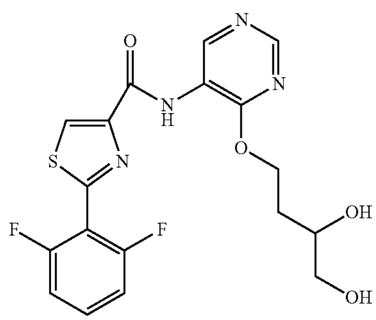 [SMILES: O=C(Nc1cncnc1OCCC(O)CO)c1csc(-c2c(F)cccc2F)n1] | ¹H NMR (400 MHz, CD₃OD) δ 1.90-2.80 (m, 2H), 3.22 (bs, 2H), 3.70-3.77 (m, 1H), 4.10-4.30 (m, 2H), 6.99-7.19 (m, 2H), 7.40-7.52 (m, 1H), 8.46 (s, 1H), 9.60 (s, 1H), 9.71 (s, 1H) | M: 422 |
| 51 | 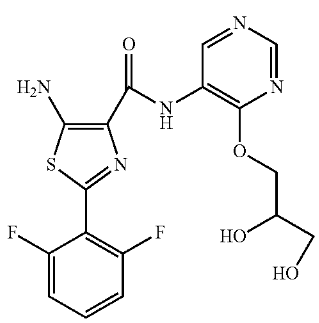 [SMILES: Nc1sc(-c2c(F)cccc2F)nc1C(=O)Nc1cncnc1OCC(O)CO] | ¹H NMR (400 MHz, CD₃OD) δ 3.50 (bs, 2H), 3.98-4.15 (m, 1H), 4.15-4.22 (m, 2H), 7.15-7.22 (m, 2H), 7.44-7.52 (m, 1H), 8.53 (s, 1H), 9.50 (s, 1H) | M: 423 |
| 52 | 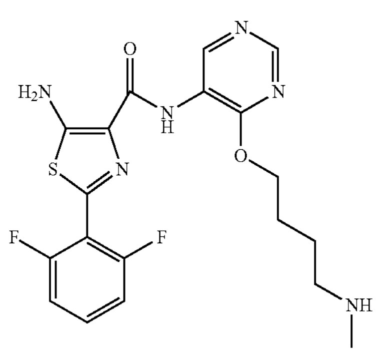 [SMILES: CNCCCCOc1ncncc1NC(=O)c1nc(-c2c(F)cccc2F)sc1N] | ¹H NMR (400 MHz, CD₃OD) δ 1.51-1.59 (m, 2H), 1.80-1.84 (m, 2H), 2.81-2.85 (m, 2H), 2.92 (s, 3H), 4.27 (t, J = 6.00 Hz, 2H), 7.16-7.19 (m, 2H), 7.42-7.48 (m, 1H), 8.47 (s, 1H), 9.49 (s, 1H) | M + 1: 435 |

-continued

| | Structure | ¹HNMR | MS |
|---|---|---|---|
| 53 | 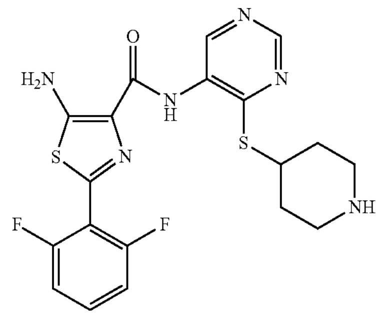 [SMILES: Nc1sc(-c2c(F)cccc2F)nc1C(=O)Nc1cncnc1SC1CCNCC1] | ¹H NMR (400 MHz, CD₃OD) δ 0.84-0.86 (m, 2H), 1.21-1.24 (m, 2H), 1.83-1.87 (m, 2H), 2.82-2.90 (m, 2H), 2.90-2.93 (m, 1H), 7.20-7.23 (m, 2H), 7.45-7.50 (m, 1H), 8.50 (s, 1H), 9.50 (s, 1H) | M + 1: 449 |
| 54 | 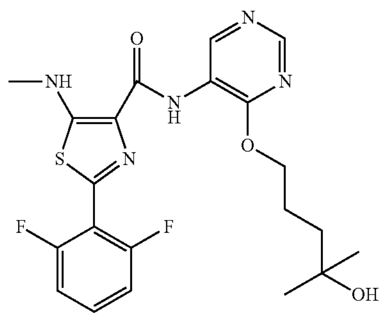 [SMILES: CNc1sc(-c2c(F)cccc2F)nc1C(=O)Nc1cncnc1OCCCC(C)(C)O] | ¹H NMR (400 MHz, CD₃OD) δ 1.14 (s, 6H), 1.40-1.50 (m, 2H), 1.70-1.80 (m, 2H), 3.20 (s, 3H), 4.21 (t, J = 6.84 Hz, 2H), 7.11-7.21 (m, 2H), 7.44-7.51 (m, 1H), 8.51 (s, 1H), 9.54 (s, 1H) | M: 463 |
| 55 | 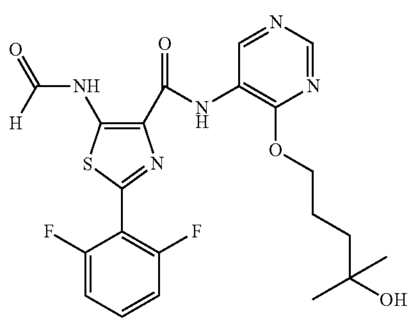 [SMILES: CC(C)(O)CCCOc1ncncc1NC(=O)c1nc(-c2c(F)cccc2F)sc1NC=O] | ¹H NMR (400 MHz, CD₃OD) δ 1.11 (s, 6H), 1.39-1.49 (m, 2H), 1.72-1.79 (m, 2H), 4.20 (t, J = 6.80 Hz, 2H), 7.15-7.21 (m, 2H), 7.42-7.53 (m, 1H), 8.50 (s, 1H), 9.55 (s, 1H), 12.01 (s, 1H) | M: 477 |
| 56 | 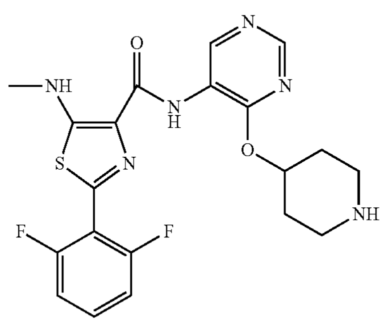 [SMILES: CNc1sc(-c2c(F)cccc2F)nc1C(=O)Nc1cncnc1OC1CCNCC1] | ¹H NMR (400 MHz, CD₃OD) δ 2.20-2.30 (m, 4H), 3.22 (s, 3H), 3.33-3.35 (m, 2H), 3.48-3.51 (m, 2H), 5.57-5.60 (m, 1H), 7.14-7.20 (m, 2H), 7.41-7.47 (m, 1H), 8.50 (s, 1H), 9.52 (s, 1H) | M + 1: 447 |

| | Structure | ¹HNMR | MS |
|---|---|---|---|
| 57 | 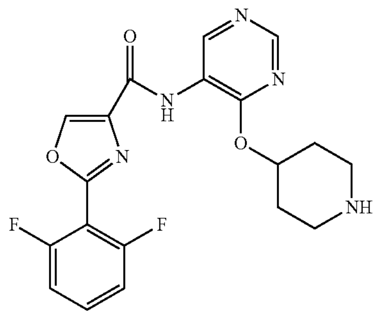 [SMILES: O=C(Nc1cncnc1OC1CCNCC1)c1coc(-c2c(F)cccc2F)n1] | ¹H NMR (400 MHz, CD₃OD) δ 2.17-2.29 (m, 4H), 3.29-3.34 (m, 2H), 3.50-3.52 (m, 2H), 5.54-5.59 (m, 1H), 7.22-7.26 (m, 2H), 7.64-7.69 (m, 1H), 8.83 (s, 1H), 9.60 (s, 1H), 9.71 (s, 1H) | M + 1: 402 |
| 58 | 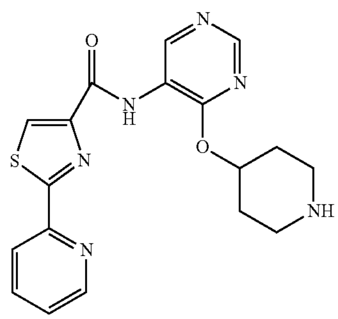 [SMILES: O=C(Nc1cncnc1OC1CCNCC1)c1csc(-c2ccccn2)n1] | ¹H NMR (400 MHz, CD₃OD) δ 2.23-2.31 (m, 4H), 3.34-3.35 (m, 2H), 3.46-3.49 (m, 2H), 5.60-5.61 (m, 1H), 7.00-7.09 (m, 1H), 7.36-7.46 (m, 1H), 7.79-7.95 (m, 1H), 8.13-8.20 (m, 1H), 8.60-8.76 (m, 1H), 9.61 (s, 1H), 9.70 (s, 1H) | M + 1: 383 |
| 59 | 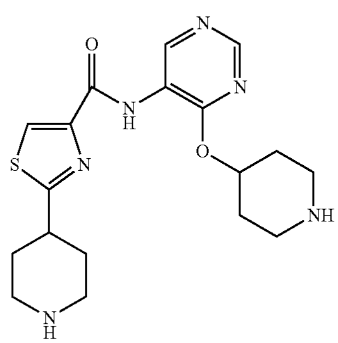 [SMILES: O=C(Nc1cncnc1OC1CCNCC1)c1csc(C2CCNCC2)n1] | ¹H NMR (400 MHz, CD₃OD) δ 1.91-1.93 (m, 2H), 2.20-2.26 (m, 3H), 2.26-2.31 (m, 4H), 3.13-3.15 (m, 4H), 3.34-3.35 (m, 2H), 3.46-3.49 (m, 2H), 5.60-5.61 (m, 1H), 8.17 (s, 1H), 9.59 (s, 1H), 9.68 (s, 1H) | M + 1: 389 |
| 60 | 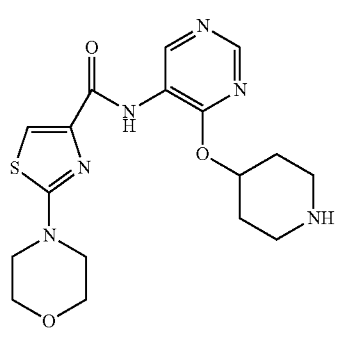 [SMILES: O=C(Nc1cncnc1OC1CCNCC1)c1csc(N2CCOCC2)n1] | ¹H NMR (400 MHz, CD₃OD) δ 2.10-2.28 (m, 4H), 3.10-3.15 (m, 4H), 3.51-3.61 (m, 4H), 3.85-3.87 (m, 4H), 5.54-5.57 (m, 1H), 8.19 (s, 1H), 9.50 (s, 1H), 9.70 (s, 1H) | M + 1: 391 |

| | Structure | ¹HNMR | MS |
|---|---|---|---|
| 61 | 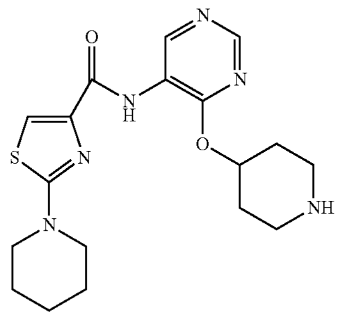 [SMILES: O=C(Nc1cncnc1OC1CCNCC1)c1csc(N2CCCCC2)n1] | ¹H NMR (400 MHz, CD₃OD) δ 1.61-1.79 (m, 6H), 3.26-3.38 (m, 4H), 3.49-3.60 (m, 4H), 3.85-3.87 (m, 4H), 5.54-5.57 (m, 1H), 8.39 (s, 1H), 9.40 (s, 1H), 9.60 (s, 1H) | M + 1: 389 |
| 62 | 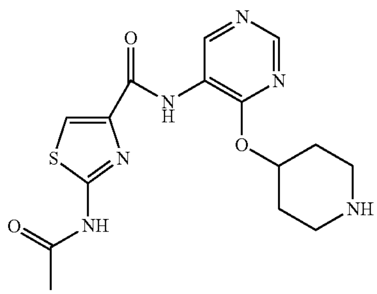 [SMILES: CC(=O)Nc1nc(C(=O)Nc2cncnc2OC2CCNCC2)cs1] | ¹H NMR (400 MHz, CD₃OD) δ 2.18-2.29 (m, 4H), 2.34 (s, 3H), 3.34-3.35 (m, 2H), 3.46-3.49 (m, 2H), 5.60-5.61 (m, 1H), 8.49 (s, 1H), 9.47 (s, 1H), 9.65 (s, 1H) | M + 1: 363 |
| 63 | 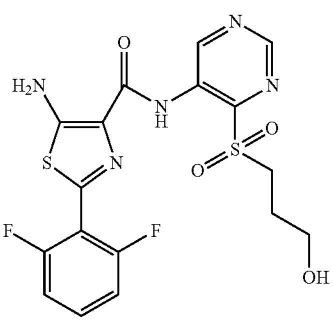 [SMILES: Nc1sc(-c2c(F)cccc2F)nc1C(=O)Nc1cncnc1S(=O)(=O)CCCO] | ¹H NMR (400 MHz, CD₃OD) δ 1.70 (m, 2H), 3.39 (m, 2H), 3.48 (m, 2H), 7.03-7.21 (m, 2H), 7.40-7.52 (m, 1H), 8.59 (s, 1H), 9.71 (s, 1H), 9.86 (s, 1H) | M + 1: 456 |

Example 64

The biochemical assays used to test the activities of the compounds of the present invention and their results.

In the present invention, the PIM activities of the compounds were tested by BioDuro (Building E, No. 29 Life Science Park Road, Changping District, Beijing, 102206, P.R. China). The method used for testing is PIM Kinase Activity Assay-IMAP Fluorescence Polarization Assay PIM Kinase Activity Assay-IMAP Fluorescence Polarization Assay 1. Principle PIM Is a serine/threonine protein kinase, they can phosphorylate 5-FAM labeled small peptide substrates. Fluorescence polarization is less for non-phosphorylated substrates since that can not bind to the binder (metal binding nanoparticles). On the other hand, fluorescence polarization is more for phosphorylated substrates since that can bind to the binder. The level of 5-FAM labeled small peptide substrates phosphorylation reflects the activities of PIM kinase. By measuring their ability of inhibiting PIM kinase of the compounds of the present invention, their activities of inhibiting PIM kinases can be determined.

2. Instrument

EnVision (PerkinElmer, Waltham, Mass.)

3. Reagents and 384 well plates

PIM1 (Millipore Cat. #14-573) (Millipore Corporation, Billerica, Mass.)

PIM2 (Millipore Cat. #14-607) (Millipore Corporation, Billerica, Mass.)

5-FAM labeled peptide (5-FAM-RSRHSSYPAGT, AnaSpec Cat.#63801) (AnaSpec Inc., Fremont, Calif.)

IMAP FP Screening Express kit (IMAP FP Screening kit) (Molecular Devices Cat.# R8127) (Molecular Devices, Sunnyvale, Calif.)

IMAP Progressive binding reagent

IMAP Progressive binding buffer A (5×)

IMAP Progressive binding buffer B (5×)

384-well black plate (Corning Cat.#3573) (Corning, Midland Mich.)

4. Assay Buffer

Tris-HCl (pH 7.2): 10 mM

MgCl₂: 10 mM

Triton X-100: 0.01%

DTT: 2 mM

5. Procedure a) 10 mM compound stock solution is diluted to appropriate concentration with 100% DMSO, then diluted 10 fold to targeted concentration with test butter to keep DMSO concentration at 10% b) Assay volume 10 ul:
1 ul of compound solution and 4 ul of enzyme (PIM-1 final concentration 0.025 nM, PIM-2 concentration 3 nM) is incubated at 23° C. for 15 min, 2.5 ul ATP (for PIM-1 and PIM-2, the final ATP concentrations are 30 uM and 5 uM respectively) 2.5 ul 5-FAM labeled peptide (final concentration 100 nM) was added to start the reaction. The reaction is run at 23° C. for 60 min. DMSO is used in place of compound stock solution as maximum reference and assay buffer is used in place of enzyme as minimum reference.
c) add 30 ul IMAP binding reagent (containing 75% IMAP Buffer A, 25% IMAP Buffer B, 1/600 dilution of beads) to stop the reaction, incubated at room temperature for 60 min
d) Measure fluorescence polarization, excitation wavelength: 485 nm, emission wavelength 530 nm.

6. Data Process $IC_{50}$ values were calculated using Graphpad Prism®.
PIM kinase assays showed that all 63 compounds in Example 1 through 63 can significantly inhibit PIM kinase activities. At 3 μM concentration, almost all compounds except the compounds listed below showed greater than 50% inhibition against PIM-1 kinase activity, some showed 100% inhibition. These compounds can also inhibit the PIM-2 and PIM-3 activities and some can inhibit 100% of the activities at 3 μM concentration.

The following compounds showed 20-50% inhibition of PIM-1 activity 3 μM concentration: 2-isopropyl-N-(4-(piperidin-4-yloxy)pyrimidin-5-yl)thiazole-4-carboxamide (33) 2-(2,6-difluorophenyl)-N-(4-(piperidin-4-yloxy)pyrimidin-5-yl)oxazole-4-carboxamide (57) 2-(piperidin-4-yl)-N-(4-(piperidin-4-yloxy)pyrimidin-5-yl)thiazole-4-carboxamide (59) 2-morpholino-N-(4-(piperidin-4-yloxy)pyrimidin-5-yl)thiazole-4-carboxamide (60) 2-(piperidin-1-yl)-N-(4-(piperidin-4-yloxy)pyrimidin-5-yl)thiazole-4-carboxamide (61) 2-acetamido-N-(4-(piperidin-4-yloxy)pyrimidin-5-yl)thiazole-4-carboxamide (62) 5-amino-2-(2,6-difluorophenyl)-N-(4-((3-hydroxypropyl)sulfonyl)pyrimidin-5-yl)thiazole-4-carboxamide (63)

I claim:
1. A compound having a structure of Formula I:

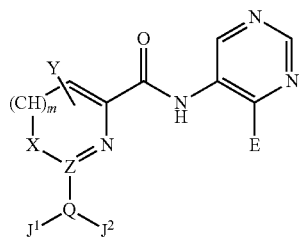

I

Wherein,
m is 0 or 1; when m is 0, X is S or O; when m is 1, X is CH or N;
Z is C or N;
Y is H, $N(R^1R^2)$, or $N(R^1C(=O)R^2)$, and $R^1$, $R^2$ are each independently selected from H, an optionally substituted $C_1$-$C_8$ aliphatic group, or an optionally substituted $C_1$-$C_8$ hydrocarbon group;
E is $OR^{22}$, $SR^{22}$, or $SO_2R^{22}$, and $R^{22}$ is an optionally substituted $C_1$-$C_8$ hydrocarbon group or a group having a formula

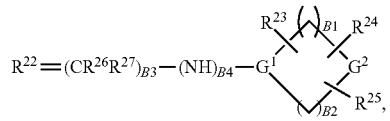

wherein
$R^{23}$, $R^{24}$, $R^{25}$ are each independently selected from H, halogen, $OR^{15}$, $NR^{16}R^{17}$, $C(=O)NR^{18}R^{19}$, or an optionally substituted $C_1$-$C_8$ hydrocarbon group, or $R^{23}$, $R^{24}$ and $R^{25}$, together with atoms to which $R^{23}$, $R^{24}$ and $R^{25}$ are attached are joined together to form a chain so that the ring to which $R^{23}$, $R^{24}$ and $R^{25}$ are attached is a substituted $C_6$-$C_{14}$ membered spiral ring, bicyclic ring, or fused ring group;
$G^1$ is CH or N;
$G^2$ is $NR^{28}$, $CHR^{29}$, or O; $R^{28}$ is H, an optionally substituted hydrocarbon group, an optionally substituted cyclic hydrocarbon group, an optionally substituted heterocyclic hydrocarbon group, $C(=O)R^{30}$, $C(=O)OR^{30}$, or $C(=O)NHR^{30}$; $R^{29}$ is OH, $NHR^{30}$, $C(=O)OR^{30}$, or $C(=O)NHR^{30}$; $R^{30}$ is H or optionally substituted $C_1$-$C_8$ hydrocarbon group;
B1 and B2 each independently represent 0, 1, 2, or 3;
B3 is 0, 1 or 2;
B4 is 1;
$R^{26}$ and $R^{27}$ are each independently selected from H or an optionally substituted $C_1$-$C_8$ hydrocarbon group;
Q is C, CH, or N;
$J^1$ and $J^2$ are each independently selected from H, an optionally substituted $C_1$-$C_8$ hydrocarbon group, $OR^{31}$, $NHR^{31}$, or $C(=O)R^{31}$; $R^{31}$ is H or optionally substituted $C_1$-$C_8$ hydrocarbon group;
or $J^1$ and $J^2$ both being attached to a CH join together to form a $C_3$-$C_8$ membered cycloalkyl, or $J^1$, $J^2$, atoms to which $J^1$ and $J^2$ are attached, and at least one hetero atom are joined together to form a $C_4$-$C_7$ membered heterocycloalkyl; on the $C_3$-$C_8$ membered cycloalkyl and the $C_4$-$C_7$ membered heterocycloalkyl, one or more positions are optionally substituted with a halogen, $OR^{32}$, $NHR^{33}$, an optionally substituted $C_1$-$C_8$ hydrocarbon group, or a substituted $C_1$-$C_8$ hydrocarbon group having the substituents joined together to form a chain so that the ring to which the substitutents are attached is a substituted $C_6$-$C_{14}$ membered spiral ring, bicyclic ring, or fused ring group; $R^{32}$ and $R^{33}$ are each independently selected from H, an optionally substituted $C_1$-$C_8$ hydrocarbon group, an optionally substituted $C_3$-$C_8$ cyclic hydrocarbon group, an optionally substituted $C_4$-$C_7$ membered heterocyclic hydrocarbon group, $C(=O)R^{34}$, $C(=O)OR^{34}$, or $C(=O)NHR^{34}$; and $R^{34}$ is H or an optionally substituted $C_1$-$C_8$ hydrocarbon group;
or $J^1$ and $J^2$, both being attached to C join together to form an aromatic ring, or $J^1$ and $J^2$, both being attached to C, and at least one heteroatom are joined with $J^1$, $J^2$, and C to form a $C_5$-$C_6$ membered aromatic heterocycle ring, and on the aromatic ring and the $C_5$-$C_6$ membered aromatic heterocycle ring, one or more positions are optionally substituted with a halogen, CN, $OR^{32}$, $NHR^{33}$, an optionally substituted $C_1$-$C_8$ hydrocarbon group, or a substituted $C_1$-$C_8$ hydrocarbon group having the substituents joined together to form a chain so that the ring to which the substituents are attached is an optionally substituted $C_6$-$C_{14}$ membered aromatic spiral ring, bicyclic ring, or fused ring group;
or $J^1$ and $J^2$, both being attached to N join together to form a $C_4$-$C_7$ membered heterocycloalkyl group, or $J^1$ and $J^2$, both being attached to N, and at least one hetero atom are joined with $J^1$, $J^2$, and N to form a $C_4$-$C_7$ membered heterocycloalkyl group; on the $C_4$-$C_7$ membered heterocycloalkyl group, one or more positions are optionally substituted with a halogen, CN, $OR^{32}$, $NHR^{33}$, an optionally substituted $C_1$-$C_8$ hydrocarbon group, or a substituted $C_1$-$C_8$ hydrocarbon group having the substituents joined together to form a chain so that the ring to which the substituents are attached is an optionally substituted $C_6$-$C_{14}$ membered aromatic spiral ring, bicyclic ring, or fused ring group.

2. The compound according to claim 1, wherein $J^1$, $J^2$, and the C to which $J^1$ and $J^2$ are attached join together to form a benzene ring or a naphthlene ring; or $J^1$, $J^2$, the carbon atom to which $J^1$ and $J^2$ are attached, and at least one heteroatom join together to form the $C_5$-$C_6$ membered aromatic heterocycle that is a pyridine, pyrimidine, pyrazine, imidazole, thiazole, isoxazole, oxazole, or pyrrole, on the aromatic ring or the aromatic heterocycle.

3. The compound according to claim 1, wherein the compound is as represented by Formular I or a diastereomer, enantiomer, tautomer, or a pharmaceutically acceptable salt of the compound as represented by Formula 1.

4. The compound according to claim 1, wherein the compound is 2-(2,6-difluorophenyl)-N-(4-(pyrrolidin-3-yloxy)pyrimidin-5-yl)thiazole-4-carboxamide (1); N-(4-(azepan-4-yloxy)pyrimidin-5-yl)-2-(2,6-difluorophenyl)thiazole-4-carboxamide (2); 2-(2,6-difluorophenyl)-N-(4-(piperidin-4-yloxy)pyrimidin-5-yl)thiazole-4-carboxamide (3); 5-amino-2-(2,6-difluorophenyl)-N-(4-(piperidin-4-yloxy)pyrimidin-5-yl)thiazole-4-carboxamide (4); 2-(2,6-difluorophenyl)-N-(4-((4-hydroxycyclohexyl)oxy)pyrimidin-5-yl)thiazole-4-carboxamide (5); 2-(2,6-difluorophenyl)-N-(4-(oxetan-3-yloxy)pyrimidin-5-yl)thiazole-4-carboxamide (6); 2-(2,6-difluorophenyl)-N-(4-((3-hydroxycyclopentyl)oxy)pyrimidin-5-yl)thiazole-4-carboxamide (7); 2-(2,6-difluorophenyl)-N-(4-((2,2,6,6-tetramethylpiperidin-4-yl)oxy)pyrimidin-5-yl)thiazole-4-carboxamide (8); 2-(2,6-difluorophenyl)-N-(4-((3-methyloxetan-3-yl)methoxy)pyrimidin-5-yl)thiazole-4-carboxamide (9); N-(4-(azetidin-3-ylmethoxy)pyrimidin-5-yl)-2-(2,6-difluorophenyl)thiazole-4-carboxamide (10); 6-(2,6-difluorophenyl)-N-(4-(piperidin-4-yloxy)pyrimidin-5-yl)picolinamide (11); 2-(2,6-difluorophenyl)-N-(4-((tetrahydrofuran-3-yl)methoxy)pyrimidin-5-yl)thiazole-4-carboxamide (12); 2-(2,6-difluorophenyl)-N-(4-((tetrahydro-2H-pyran-4-yl)methoxy)pyrimidin-5-yl)thiazole-4-carboxamide (13); N-(4-(8-azabicyclo[3.2.1]octan-3-yloxy)pyrimidin-5-yl)-2-(2,6-difluorophenyl)thiazole-4-carboxamide (14); 2-(2,6-difluorophenyl)-N-(4-(piperidin-4-ylmethoxy)pyrimidin-5-yl)thiazole-4-carboxamide (15); 2-(2,6-difluorophenyl)-N-(4-((tetrahydro-2H-pyran-4-yl)oxy)pyrimidin-5-yl)thiazole-4-carboxamide (16); N-(4-(3-azabicyclo[3.2.0]heptan-6-yloxy)pyrimidin-5-yl)-2-(2,6-difluorophenyl)thiazole-4-carboxamide (17); 2-(2,6-difluorophenyl)-N-(4-(pyrrolidin-3-ylmethoxy)pyrimidin-5-yl)thiazole-4-carboxamide (18); 2-(2,6-difluorophenyl)-N-(4-(quinuclidin-3-ylmethoxy)pyrimidin-5-yl)thiazole-4-carboxamide (19); 3-amino-6-(2,6-difluorophenyl)-N-(4-((3-methyloxetan-3-yl)methoxy)pyrimidin-5-yl)picolinamide (20); N-(4-(azetidin-3-yloxy)pyrimidin-5-yl)-2-(2,6-difluorophenyl)thiazole-4-carboxamide (21); 2-(2,6-difluorophenyl)-N-(4-(piperidin-3-yloxy)pyrimidin-5-yl)thiazole-4-carboxamide (22); N-(4-((cis-4-aminocyclohexyl)oxy)pyrimidin-5-yl)-2-(2,6-difluorophenyl)thiazole-4-carboxamide (24); 5-amino-2-(2,6-difluorophenyl)-N-(4-((3-methyloxetan-3-yl)methoxy)pyrimidin-5-yl)thiazole-4-carboxamide (25); 5-amino-N-(4-(azepan-4-yloxy)pyrimidin-5-yl)-2-(2,6-difluorophenyl)thiazole-4-carboxamide (26); 5-amino-N-(4-((trans-4-aminocyclohexyl)oxy)pyrimidin-5-yl)-2-(2,6-difluorophenyl)thiazole-4-carboxamide (27); 5-amino-2-(2,6-difluorophenyl)-N-(4-(piperidin-4-ylmethoxy)pyrimidin-5-yl)thiazole-4-carboxamide (28); 5-amino-N-(4-(4-aminobutoxy)pyrimidin-5-yl)-2-(2,6-difluorophenyl)thiazole-4-carboxamide (29); 5-amino-2-(2,6-difluorophenyl)-N-(4-(4-hydroxybutoxy)pyrimidin-5-yl)thiazole-4-carboxamide (30); 2-(2,6-difluorophenyl)-N-(4-(((3S,4R)-3-fluoropiperidin-4-yl)oxy)pyrimidin-5-yl)thiazole-4-carboxamide (31); 3-amino-6-(2,6-difluorophenyl)-N-(4-(piperidin-4-yloxy)pyrimidin-5-yl)picolinamide (32); 5-amino-2-(2,6-difluorophenyl)-N-(4-(pyrrolidin-3-yloxy)pyrimidin-5-yl)thiazole-4-carboxamide (34); 2-(2,6-difluorophenyl)-N-(4-(((1S,3R)-3-hydroxycyclopentyl)oxy)pyrimidin-5-yl)thiazole-4-carboxamide (37); 5-amino-2-(2,6-difluorophenyl)-N-(4-(3-hydroxy-3-methylbutoxy)pyrimidin-5-yl)thiazole-4-carboxamide (39); 2-(2,6-difluorophenyl)-N-(4-(3-hydroxy-3-methylbutoxy)pyrimidin-5-yl)thiazole-4-carboxamide (40); 5-amino-2-(2,6-difluorophenyl)-N-(4-(3-hydroxybutoxy)pyrimidin-5-yl)thiazole-4-carboxamide (41); 2-(2,6-difluorophenyl)-N-(4-(3-hydroxybutoxy)pyrimidin-5-yl)thiazole-4-carboxamide (42); 5-amino-N-(4-((4-carbamoylcyclohexyl)oxy)pyrimidin-5-yl)-2-(2,6-difluorophenyl)thiazole-4-carboxamide (43); 5-amino-2-(2,6-difluorophenyl)-N-(4-((4-hydroxypentyl)oxy)pyrimidin-5-yl)thiazole-4-carboxamide (45); 2-(2,6-difluorophenyl)-N-(4-((4-hydroxypentyl)oxy)pyrimidin-5-yl)thiazole-4-carboxamide (46); 5-amino-2-(2,6-difluorophenyl)-N-(4-((4-hydroxy-4-methylpentyl)oxy)pyrimidin-5-yl)thiazole-4-carboxamide(47); 2-(2,6-difluorophenyl)-N-(4-((4-hydroxy-4-methylpentyl)oxy)pyrimidin-5-yl)thiazole-4-carboxamide (48); 5-amino-2-(2,6-difluorophenyl)-N-(4-(3,4-dihydroxybutoxy)pyrimidin-5-yl)thiazole-4-carboxamide (49); 2-(2,6-difluorophenyl)-N-(4-(3,4-dihydroxybutoxy)pyrimidin-5-yl)thiazole-4-carboxamide (50); 5-amino-2-(2,6-difluorophenyl)-N-(4-(2,3-dihydroxypropoxy)pyrimidin-5-yl)thiazole-4-carboxamide (51); 5-amino-2-(2,6-difluorophenyl)-N-(4-(4-(methylamino)butoxy)pyrimidin-5-yl)thiazole-4-carboxamide (52); 5-amino-2-(2,6-difluorophenyl)-N-(4-(piperidin-4-ylthio)pyrimidin-5-yl)thiazole-4-carboxamide (53); or N-(4-(piperidin-4-yloxy)pyrimidin-5-yl)-2-(pyridin-2-yl)thiazole-4-carboxamide (58).

5. The compound according to claim 4, wherein the compound is 2-(2,6-difluorophenyl)-N-(4-(pyrrolidin-3-yloxy)pyrimidin-5-yl)thiazole-4-carboxamide (1); N-(4-(azepan-4-yloxy)pyrimidin-5-yl)-2-(2,6-difluorophenyl)thiazole-4-carboxamide (2); 2-(2,6-difluorophenyl)-N-(4-(piperidin-4-yloxy)pyrimidin-5-yl)thiazole-4-carboxamide (3); 5-amino-2-(2,6-difluorophenyl)-N-(4-(piperidin-4-yloxy)pyrimidin-5-yl)thiazole-4-carboxamide (4); 2-(2,6-difluorophenyl)-N-(4-((4-hydroxycyclohexyl)oxy)pyrimidin-5-yl)thiazole-4-carboxamide (5); 2-(2,6-difluorophenyl)-N-(4-((3-methyloxetan-3-yl)methoxy)pyrimidin-5-yl)thiazole-4-carboxamide (9); N-(4-(azetidin-3-ylmethoxy)pyrimidin-5-yl)-2-(2,6-difluorophenyl)thiazole-4-carboxamide (10); 2-(2,6-difluorophenyl)-N-(4-((tetrahydrofuran-3-yl)methoxy)pyrimidin-5-yl)thiazole-4-carboxamide (12); 2-(2,6-difluorophenyl)-N-(4-((tetrahydro-2H-pyran-4-yl)methoxy)pyrimidin-5-yl)thiazole-4-carboxamide (13); 2-(2,6-difluorophenyl)-N-(4-(piperidin-4-ylmethoxy)pyrimidin-5-yl)thiazole-4-carboxamide (15); 2-(2,6-difluorophenyl)-N-(4-((tetrahydro-2H-pyran-4-yl)oxy)pyrimidin-5-yl)thiazole-4-carboxamide (16); 2-(2,6-difluorophenyl)-N-(4-(pyrrolidin-3-ylmethoxy)pyrimidin-5-yl)thiazole-4-carboxamide (18); N-(4-(azetidin-3-yloxy)pyrimidin-5-yl)-2-(2,6-difluorophenyl)thiazole-4-carboxamide (21); 2-(2,6-difluorophenyl)-N-(4-(piperidin-3-yloxy)pyrimidin-5-yl)thiazole-4-carboxamide (22); N-(4-((cis-4-aminocyclohexyl)oxy)pyrimidin-5-yl)-2-(2,6-difluorophenyl)thiazole-4-carboxamide (24); 5-amino-2-(2,6-difluorophenyl)-N-(4-((3-methyloxetan-3-yl)methoxy)pyrimidin-5-yl)thiazole-4-carboxamide (25); 5-amino-N-(4-

(azepan-4-yloxy)pyrimidin-5-yl)-2-(2,6-difluorophenyl)
thiazole-4-carboxamide (26); 5-amino-N-(4-((trans-4-aminocyclohexyl)oxy)pyrimidin-5-yl)-2-(2,6-difluorophenyl)
thiazole-4-carboxamide (27); 5-amino-2-(2,6-difluorophenyl)-N-(4-(piperidin-4-ylmethoxy)pyrimidin-5-yl)thiazole-4-carboxamide (28); 5-amino-N-(4-(4-aminobutoxy)pyrimidin-5-yl)-2-(2,6-difluorophenyl)
thiazole-4-carboxamide (29); 5-amino-2-(2,6-difluorophenyl)-N-(4-(4-hydroxybutoxy)pyrimidin-5-yl)
thiazole-4-carboxamide (30); 3-amino-6-(2,6-difluorophenyl)-N-(4-(piperidin-4-yloxy)pyrimidin-5-yl)
picolinamide (32); 5-amino-2-(2,6-difluorophenyl)-N-(4-(pyrrolidin-3-yloxy)pyrimidin-5-yl)thiazole-4-carboxamide (34); 2-(2,6-difluorophenyl)-N-(4-((1S,3R)-3-hydroxycyclopentyl)oxy)pyrimidin-5-yl)thiazole-4-carboxamide (37);
5-amino-2-(2,6-difluorophenyl)-N-(4-(3-hydroxy-3-methylbutoxy)pyrimidin-5-yl)thiazole-4-carboxamide (39); 2-(2,6-difluorophenyl)-N-(4-(3-hydroxy-3-methylbutoxy)pyrimidin-5-yl)thiazole-4-carboxamide (40); 5-amino-2-(2,6-difluorophenyl)-N-(4-(3-hydroxybutoxy)pyrimidin-5-yl)
thiazole-4-carboxamide (41); 2-(2,6-difluorophenyl)-N-(4-(3-hydroxybutoxy)pyrimidin-5-yl)thiazole-4-carboxamide (42); 5-amino-2-(2,6-difluorophenyl)-N-(4-((4-hydroxypentyl)oxy)pyrimidin-5-yl)thiazole-4-carboxamide (45); 2-(2,6-difluorophenyl)-N-(4-((4-hydroxypentyl)oxy)pyrimidin-5-yl)thiazole-4-carboxamide (46); 5-amino-2-(2,6-difluorophenyl)-N-(4-((4-hydroxy-4-methylpentyl)oxy)pyrimidin-5-yl)thiazole-4-carboxamide(47); 2-(2,6-difluorophenyl)-N-(4-((4-hydroxy-4-methylpentyl)oxy)pyrimidin-5-yl)thiazole-4-carboxamide (48); 5-amino-2-(2,6-difluorophenyl)-N-(4-(3,4-dihydroxybutoxy)pyrimidin-5-yl)thiazole-4-carboxamide (49); 2-(2,6-difluorophenyl)-N-(4-(3,4-dihydroxybutoxy)pyrimidin-5-yl)thiazole-4-carboxamide (50); 5-amino-2-(2,6-difluorophenyl)N-(4-(4-(methylamino)butoxy)pyrimidin-5-yl)thiazole-4-carboxamide (52); or 5-amino-2-(2,6-difluorophenyl)-N-(4-(piperidin-4-ylthio)pyrimidin-5-yl)thiazole-4-carboxamide (53).

6. The process for preparing the compound of claim 1, comprising

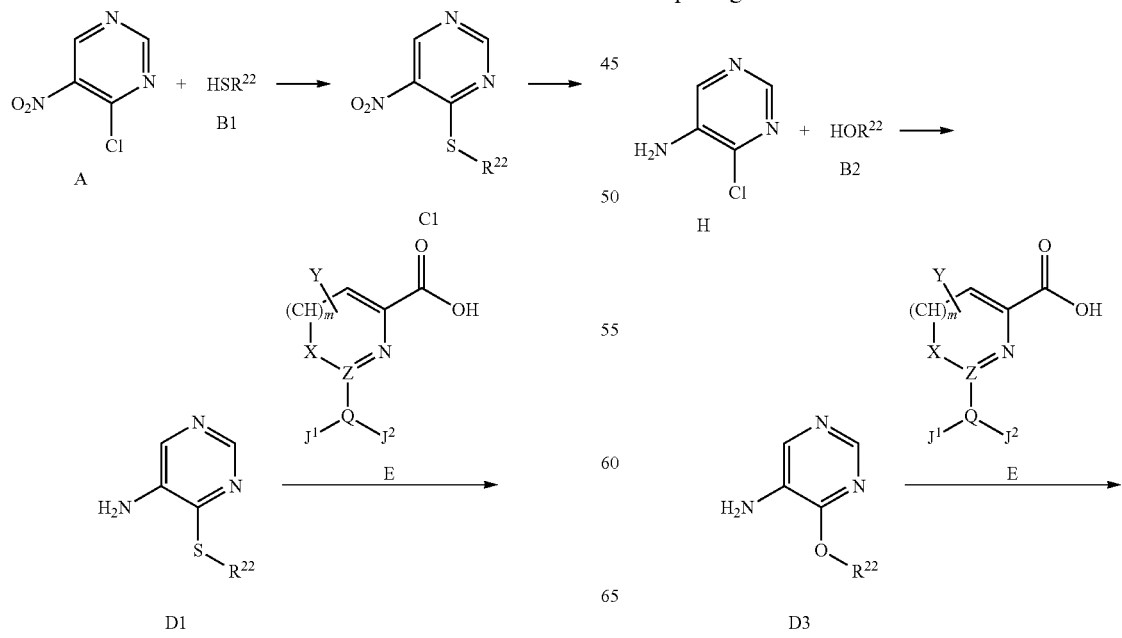

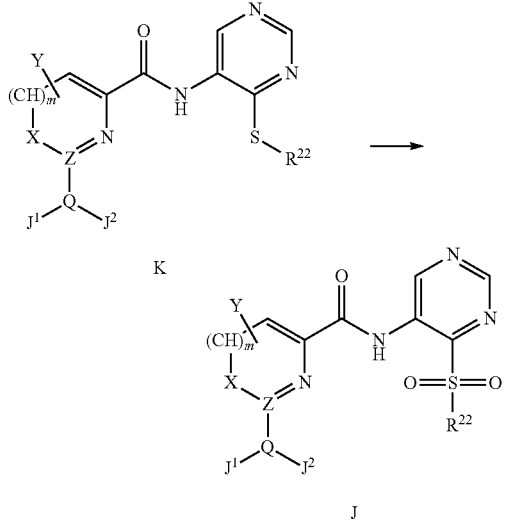

reacting protected or unprotected thiol B1 with 4-Chloro-3-nitropyrimidine A in a first solvent to form a thioether C1, reacting the thioether C1 with $Na_2S_2O_4$ in a second solvent so as to reduce the thioether C1 to aminopyrimidine D1, reacting a protected or unprotected aromatic carboxylic acid E in a third solvent at a heated condition with the aminopyrimidine D1 to form a thioether K, optionally deprotecting the protected thioether K, oxidizing the optionally deprotected thiol ether K by reacting with m-chloroperoxybenzoic acid (m-CPBA) in a fourth solvent to form sulfone product J, and optionally deprotecting the sulfone product J, wherein E is a sulfur or sulfone group; K is final thioether product of Formula I when E is a sulfur group; K is optionally protected by a protecting group; J is optionally protected by a protecting group.

7. The process for preparing the compound of claim 1, comprising

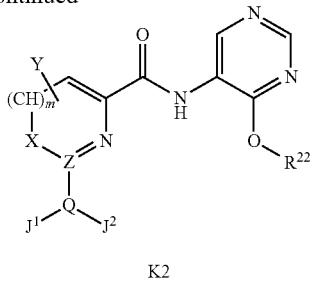

K2 reacting a protected or unprotected alcohol B2 to form a mixture, reacting the mixture with 5-amino-4-chloropyrimidine H at heated condition to form aminopyrimidine ether D3, reacting aminopyrimidine ether D3 with a protected or unprotected aromatic carboxylic acid E at heated condition to form ether K2, and optionally deprotecting ether K2, wherein E is an ether group.

8. The method for treating hematopoeitic malignancy, prostate cancer, pancreatic cancer, human chronic lymphocytic leukemia, non-Hodgkin's lymphoma leukemia, and pancreatic cancer according to claim 1, comprising administering to an object in need of the treatment a therapeutically effective amount of the compound of claim 1.

9. A pharmaceutical composition comprising the compound of claim 1 as an active pharmaceutical ingredient, and a pharmaceutically acceptable carrier or adjuvant.

10. A pharmaceutical composition comprising the compound of claim 3 as an active pharmaceutical ingredient, and a pharmaceutically acceptable carrier or adjuvant.

11. A method for inhibiting PIM kinase comprising contacting a PIM kinase with the compound as defined in claim 1.

* * * * *